US009812643B2

(12) United States Patent
Buesing et al.

(10) Patent No.: US 9,812,643 B2
(45) Date of Patent: Nov. 7, 2017

(54) MATERIALS FOR ELECTRONIC DEVICES

(71) Applicants: Merck Patent GmbH, Darmstadt (DE); Samsung Display Co., Ltd., Yongin, Gyeonggi-Do (KR)

(72) Inventors: Arne Buesing, Frankfurt am Main (DE); Holger Heil, Frankfurt am Main (DE); Philipp Stoessel, Frankfurt am Main (DE); Frank Voges, Bad Duerkheim (DE); Constanze Brocke, Gross-Gerau (DE); Yoonhyun Kwak, Yongin (KR); Hyein Jeong, Yongin (KR); Samil Khol, Yongin (KR); Sunyoung Lee, Yongin (KR)

(73) Assignees: Merck Patent GmbH, Darmstadt (DE); Samsung Display Co., Ltd., Yongin, Gyeonggi-Do (KR)

( * ) Notice: Subject to any disclaimer, the term of this patent is extended or adjusted under 35 U.S.C. 154(b) by 517 days.

(21) Appl. No.: 14/354,153

(22) PCT Filed: Oct. 9, 2012

(86) PCT No.: PCT/EP2012/004225
§ 371 (c)(1),
(2) Date: Apr. 25, 2014

(87) PCT Pub. No.: WO2013/060418
PCT Pub. Date: May 2, 2013

(65) Prior Publication Data
US 2014/0291586 A1 Oct. 2, 2014

(30) Foreign Application Priority Data

Oct. 27, 2011 (EP) ..................... 11008620

(51) Int. Cl.
*H01L 51/50* (2006.01)
*H01L 51/00* (2006.01)
*C09K 11/06* (2006.01)
*H05B 33/22* (2006.01)
*C07D 487/14* (2006.01)
*C07D 251/24* (2006.01)
*C07D 209/86* (2006.01)

(52) U.S. Cl.
CPC ........ *H01L 51/0039* (2013.01); *C07D 209/86* (2013.01); *C07D 251/24* (2013.01); *C07D 487/14* (2013.01); *C09K 11/06* (2013.01); *H01L 51/0036* (2013.01); *H01L 51/0059* (2013.01); *H01L 51/0072* (2013.01); *H05B 33/22* (2013.01); *C09K 2211/1029* (2013.01); *H01L 51/5056* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| 7,737,627 | B2 | 6/2010 | Hwang et al. | |
|---|---|---|---|---|
| 9,434,877 | B2 | 9/2016 | Pflumm et al. | |
| 2008/0024054 | A1 | 1/2008 | Itoh et al. | |
| 2009/0160323 | A1 | 6/2009 | Nomura et al. | |
| 2010/0025669 | A1* | 2/2010 | Hwang ................ | C07D 401/12 257/40 |
| 2010/0219400 | A1 | 9/2010 | Arakane et al. | |
| 2010/0308311 | A1 | 12/2010 | Mitsui et al. | |
| 2011/0215308 | A1 | 9/2011 | Im et al. | |
| 2011/0272684 | A1 | 11/2011 | Parham et al. | |
| 2012/0043531 | A1* | 2/2012 | Jung ..................... | H01L 51/006 257/40 |
| 2012/0223276 | A1 | 9/2012 | Parham et al. | |
| 2013/0001532 | A1 | 1/2013 | Hwang et al. | |
| 2013/0069049 | A1 | 3/2013 | Park et al. | |
| 2013/0207092 | A1 | 8/2013 | Huh et al. | |
| 2014/0042412 | A1 | 2/2014 | Ryu et al. | |

FOREIGN PATENT DOCUMENTS

| EP | 2 149 555 A1 | 3/2010 |
|---|---|---|
| EP | 2 365 555 A2 | 3/2011 |
| EP | 2 468 725 A1 | 6/2012 |
| JP | 2005290000 A | 10/2005 |
| JP | 2008511970 A | 4/2008 |
| JP | 2009298767 A | 12/2009 |
| JP | 2011176259 A | 9/2011 |
| JP | 2011187959 A | 9/2011 |
| JP | 2013515361 A | 5/2013 |
| KR | 20110056728 A | 5/2011 |
| KR | 20110088898 A | 8/2011 |
| KR | 20110105664 A | 9/2011 |
| WO | WO-2009099060 A1 | 8/2009 |
| WO | WO-2010041872 A2 | 4/2010 |
| WO | WO-2010/050778 A1 | 5/2010 |
| WO | WO-2010/110553 A2 | 9/2010 |
| WO | WO-2010098458 A1 | 9/2010 |
| WO | WO-2011057706 A2 | 5/2011 |
| WO | WO-2011076323 A1 | 6/2011 |
| WO | WO-2011110262 A1 | 9/2011 |
| WO | WO-2011149283 A2 | 12/2011 |
| WO | WO-2012039534 A1 | 3/2012 |
| WO | WO-2012141393 A1 | 10/2012 |
| WO | WO-2013032304 A2 | 3/2013 |

OTHER PUBLICATIONS

International Search Report dated Dec. 3, 2012 for PCT/EP2012/004225.
Japanese Office Action for Application No. 2014-537512, dated Jan. 10, 2017.
English Translation of Japanese Office Action for Application No. 2014-537512, dated Jan. 10, 2017.

* cited by examiner

*Primary Examiner* — Gregory Clark
(74) *Attorney, Agent, or Firm* — Drinker Biddle & Reath LLP

(57) ABSTRACT

The present invention relates to compounds of the formula (I), to the use of compounds of the formula (I) in electronic devices, and to electronic devices comprising one or more compounds of the formula (I). The invention furthermore relates to the preparation of the compounds of the formula (I) and to formulations comprising one or more compounds of the formula (I).

24 Claims, No Drawings

MATERIALS FOR ELECTRONIC DEVICES

CROSS-REFERENCE TO RELATED APPLICATIONS

This application is a national stage application (under 35 U.S.C. §371) of PCT/EP2012/004225, filed Oct. 9, 2012, which claims benefit of European Application No. 11008620.4, filed Oct. 27, 2011, both of which are incorporated herein by reference in their entirely.

The present invention relates to compounds of the formula (I), to the use of compounds of the formula (I) in electronic devices, and to electronic devices comprising one or more compounds of the formula (I). The invention furthermore relates to the preparation of the compounds of the formula (I) and to formulations comprising one or more compounds of the formula (I).

The compounds of the formula (I) are used in accordance with the invention in electronic devices, preferably in organic electroluminescent devices (OLEDs). The general structure of these devices is described, for example, in U.S. Pat. Nos. 4,539,507, 5,151,629, EP 0676461 and WO 98/27136.

Hole-transport and -injection materials which are known from the prior art for organic electroluminescent devices are, inter alia, arylamine compounds. Materials of this type based on an indenofluorene skeleton are disclosed, for example, in WO 2006/100896 and WO 2006/122630.

However, the hole-transporting materials known from the prior art frequently have low electron stability, which reduces the lifetime of electronic devices comprising these compounds. Overall, further improvements are desirable with respect to the efficiency of fluorescent organic electroluminescent devices and the lifetime, especially in the case of blue-fluorescent devices. There is furthermore potential for improvement in the operating voltage of the electronic devices.

There is therefore a demand for alternative compounds which can be used in organic electroluminescent devices and which preferably effect an improvement in the above-mentioned performance data of the devices.

Matrix materials which are known from the prior art for phosphorescent dopants are, inter alia, carbazole derivatives, for example bis(carbazolyl)-biphenyl. The use of ketones (WO 2004/093207), phosphine oxides and sulfones (WO 2005/003253) as matrix materials for phosphorescent dopants is furthermore known. Metal complexes, for example BAlq or bis[2-(2-benzothiazole)phenolate]zinc(II), are also used as matrix materials for phosphorescent dopants.

However, there continues to be a demand for alternative matrix materials for phosphorescent dopants, in particular those which effect an improvement in the performance data of the electronic devices.

Furthermore, the provision of alternative materials as matrix components of mixed-matrix systems is of particular interest. A mixed-matrix system in the sense of this application is taken to mean a system in which two or more different matrix compounds are used together with one (or more) dopant compounds mixed in an emitting layer. These systems are, in particular, of interest in the case of phosphorescent organic electroluminescent devices. For more detailed information, see the application WO 2010/108579.

Compounds known from the prior art which may be mentioned as matrix components in mixed-matrix systems are, inter alia, CBP (biscarbazolylbiphenyl) and TCTA (tris-carbazolyltriphenylamine) (first component). Suitable as the second component are compounds such as, for example, benzophenone derivatives, diazaphospholes (cf. WO 2010/054730) and triazines. However, there continues to be a demand for alternative compounds for use as matrix components in mixed-matrix systems. In particular, there is a demand for compounds which effect an improvement in the operating voltage and lifetime of the electronic devices.

The applications US 2005/0221124 A1 and EP 2202818 A1 disclose the use of arylamine compounds containing a carbazole unit and a fluorene unit as functional materials in organic electroluminescent devices.

However, there continues to be a demand for materials having improved properties, in particular those which facilitate an improvement in the power efficiency, the operating voltage and/or the lifetime of the organic electroluminescent devices.

It has been found as part of the present invention that compounds of the formula (I) shown below are eminently suitable for use as functional materials in organic electroluminescent devices and effect an improvement in the above-mentioned performance data.

The present invention thus relates to a compound of the formula (I)

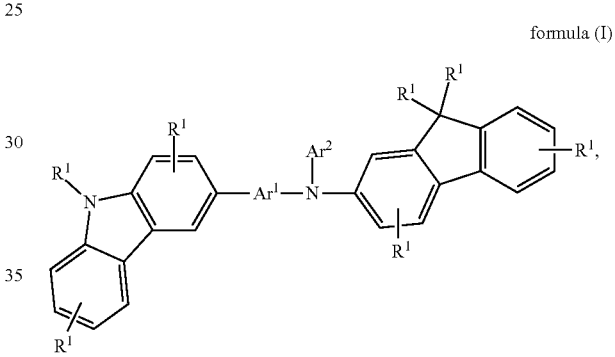

formula (I)

where the following applies to the symbols occurring:

$Ar^1$ is an aromatic ring system having 6 to 30 aromatic ring atoms or a heteroaromatic ring system having 5 to 30 aromatic ring atoms, which is substituted by at least one radical $R^4$ and which may furthermore be substituted by one or more radicals $R^1$;

$Ar^2$ is an aromatic ring system having 6 to 30 aromatic ring atoms or a heteroaromatic ring system having 5 to 30 aromatic ring atoms, which may be substituted by one or more radicals $R^1$;

$R^4$ is on each occurrence, identically or differently, F, Cl, CN, $Si(R^3)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^3$ and where one or more adjacent or non-adjacent $CH_2$ groups in the above-mentioned groups may be replaced by —$R^3C$=$CR^3$—, —C≡C—, —$Si(R^3)_2$—, C=O, C=$NR^3$, —COO—, —$CONR^3$—, —$NR^3$—, P(=O)($R^3$), —O—, —S—, SO or $SO_2$ and where one or more H atoms in the above-mentioned groups may be replaced by D, F, Cl, Br, I, CN or $NO_2$;

$R^1$ is on each occurrence, identically or differently, H, D, F, Cl, Br, I, B(OR³)₂, CHO, C(O)R³, $CR^3$=$C(R^3)_2$, CN, $COOR^3$, $CON(R^3)_2$, $Si(R^3)_3$, $N(R^3)_2$, $NO_2$, P(=O)($R^3$)₂, $OSO_2R^3$, OH, S(=O)$R^3$, S(=O)₂$R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, where the above-mentioned groups may each be substituted by one or more radicals $R^3$ and where one or more adjacent or non-adjacent $CH_2$ groups in the above-mentioned groups may be replaced by —$R^3C$═$CR^3$—, —C≡C—, $Si(R^3)_2$, $Ge(R^3)_2$, $Sn(R^3)_2$, C═O, C═S, C═Se, C═$NR^3$, —COO—, —$CONR^3$—, $NR^3$, P(═O) ($R^3$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may be substituted by one or more radicals $R^3$, or a combination of these systems, where two or more radicals $R^1$ may be linked to one another and may form an aliphatic or aromatic ring;

$R^3$ is, identically or differently on each occurrence, H, D, F or an aliphatic, aromatic and/or heteroaromatic organic radical having 1 to 20 C atoms, in which, in addition, one or more H atoms may be replaced by D or F; two or more substituents $R^3$ here may also be linked to one another and form an aliphatic or aromatic ring.

The notation

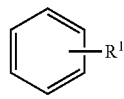

used in formula (I) and below denotes that a group $R^1$ may be bonded to any of the free positions of the aromatic ring.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals $R^1$ or $R^3$ and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore. systems in which two or more aryl or heteroaryl groups are linked to one another via one or more single bonds are also taken to be aromatic or heteroaromatic ring systems in the sense of this invention.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH$_2$ groups may be substituted by the groups mentioned above under the definition of the radical R$^1$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

In a preferred embodiment of the invention, Ar$^1$ represents a group which conforms to one of the formulae Ar$^1$-1 to Ar$^1$-20:

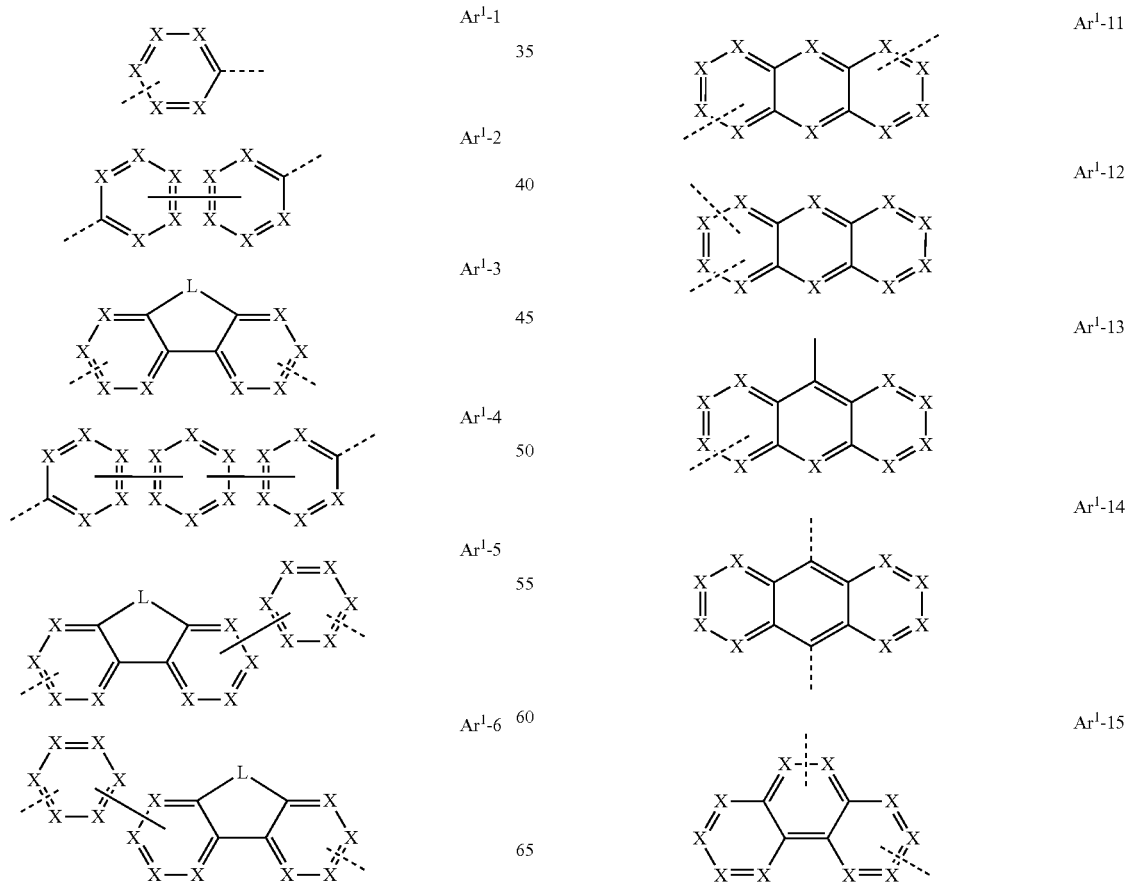

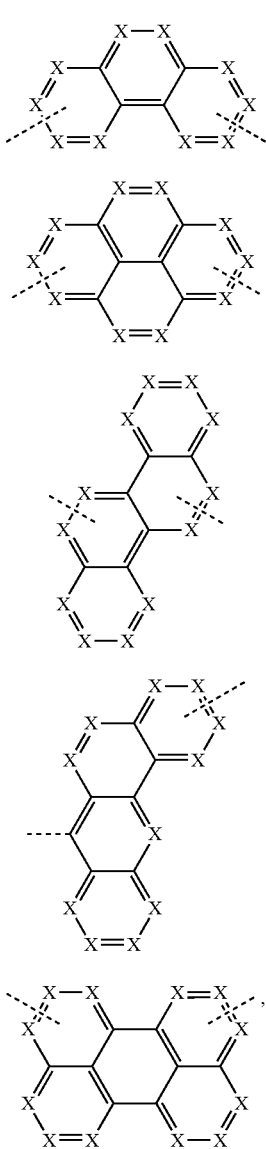

Ar¹-16

Ar¹-17

Ar¹-18

Ar¹-19

Ar¹-20 where
X is on each occurrence, identically or differently, CR$^A$, CR$^1$, C or N, where at least one group X per formula must be equal to CR$^A$ and where X is equal to C if a dashed or continuous line or a group L is bonded at the position in question;
L is on each occurrence, identically or differently, a divalent group selected from C(R$^1$)$_2$, R$^1$C=CR$^1$, Si(R$^1$)$_2$, C=O, C=NR$^1$, O, S, SO, SO$_2$, PR$^1$, POR' and NR$^1$;
where R$^A$ and R$^1$ are as defined above;
and where the two bonds to the radical of the formula (I) are reproduced by the two dashed lines, and where the dashed line on the left denotes the bond from the group Ar$^1$ to the carbazole group and the dashed line on the right denotes the bond from the group Ar$^1$ to the nitrogen atom.

In a preferred embodiment of the invention,
L is on each occurrence, identically or differently, a divalent group selected from C(R$^1$)$_2$, C=O, O, S and NR$^1$.

In a preferred embodiment of the invention, X is on each occurrence, identically or differently, CR$^A$, CR$^1$ or C, where at least one group X per formula must be equal to CR$^A$ and where X is equal to C if a dashed or continuous line or a group L is bonded at the position in question.

Particularly preferred embodiments of the group Ar$^1$ conform to one of the following formulae Ar$^1$-21 to Ar$^1$-64:

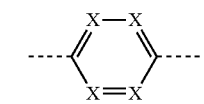

Ar¹-21

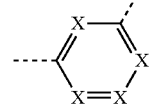

Ar¹-22

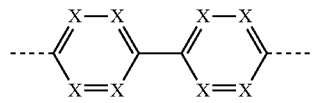

Ar¹-23

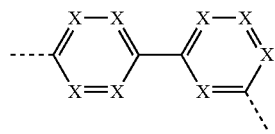

Ar¹-24

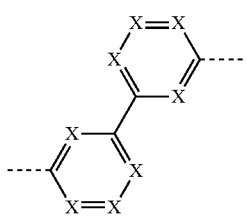

Ar¹-25

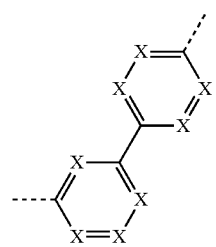

Ar¹-26

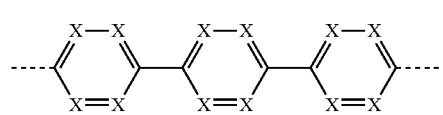

Ar¹-27

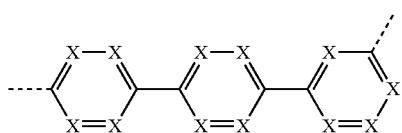

Ar¹-28

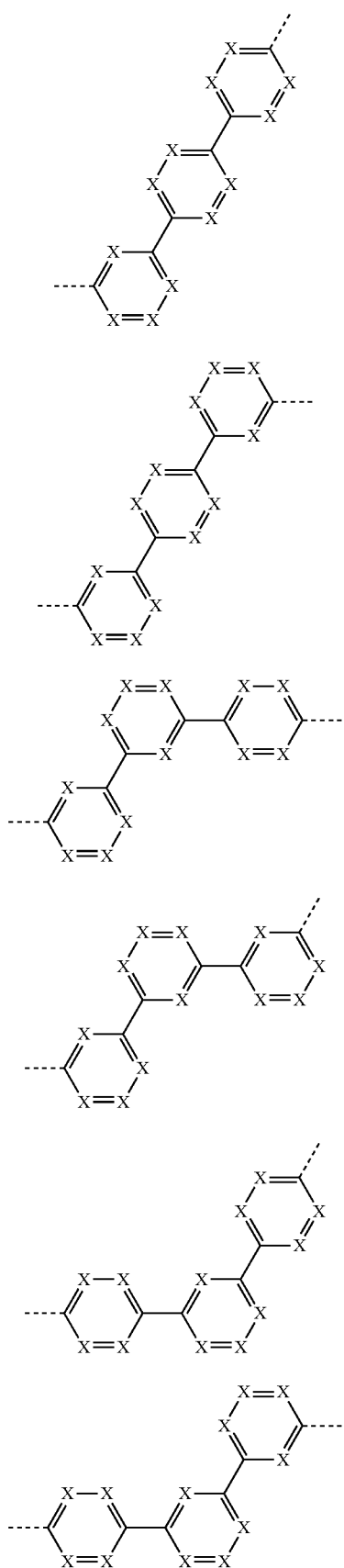
Ar¹-29
Ar¹-30
Ar¹-31
Ar¹-32
Ar¹-33
Ar¹-34
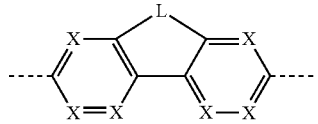 Ar¹-35
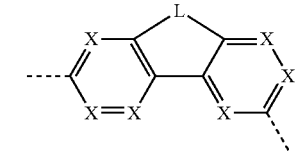 Ar¹-36
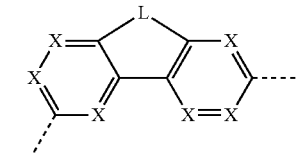 Ar¹-37
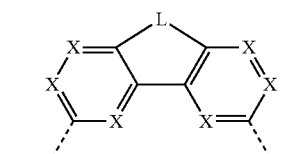 Ar¹-38
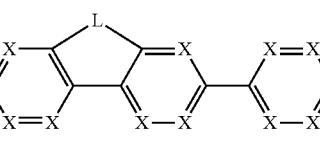 Ar¹-39
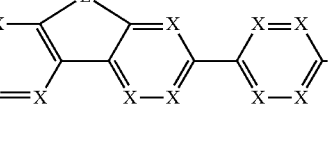 Ar¹-40
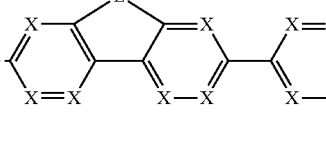 Ar¹-41
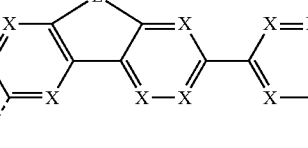 Ar¹-42
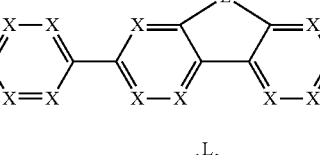 Ar¹-43
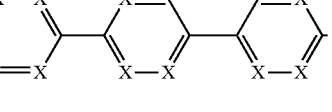 Ar¹-44

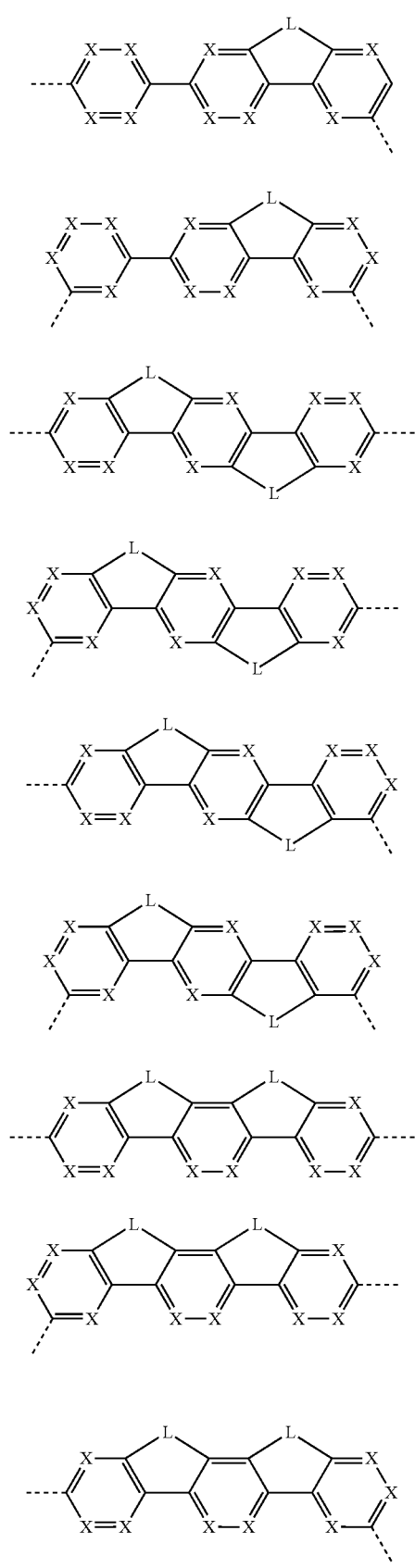
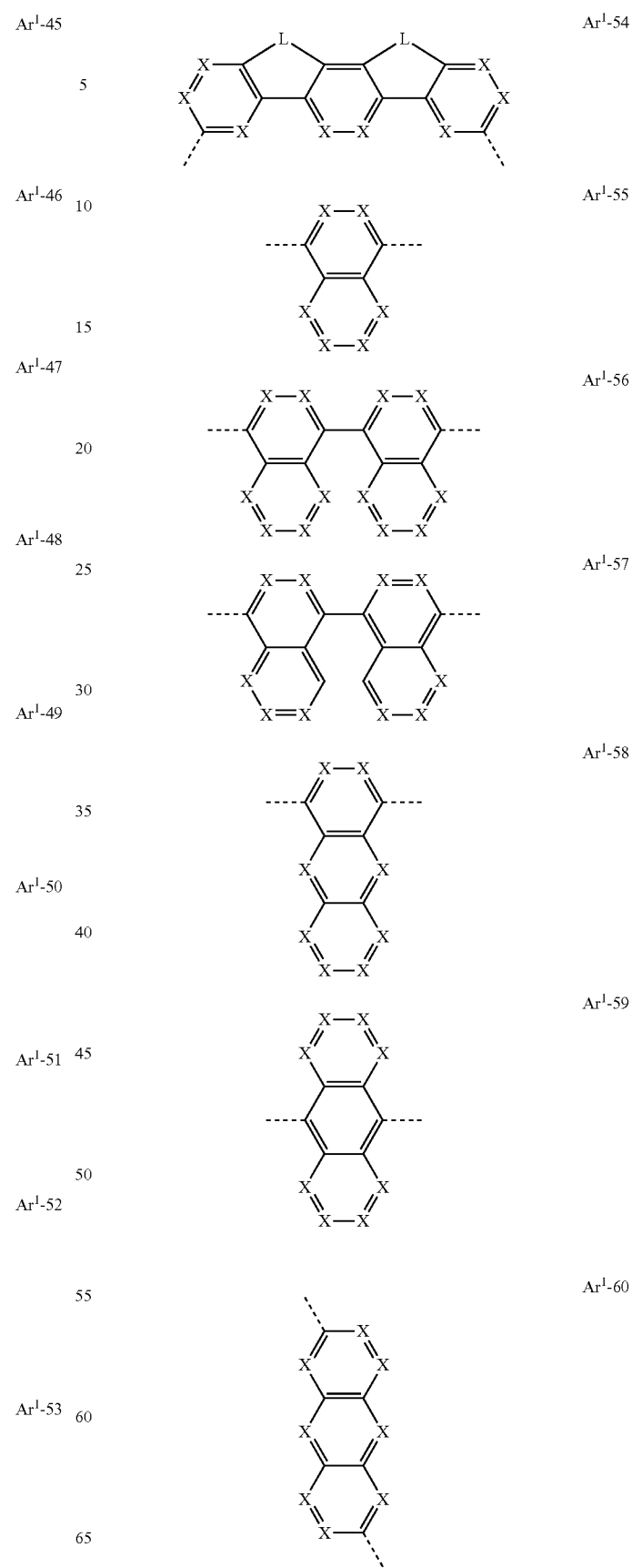

-continued

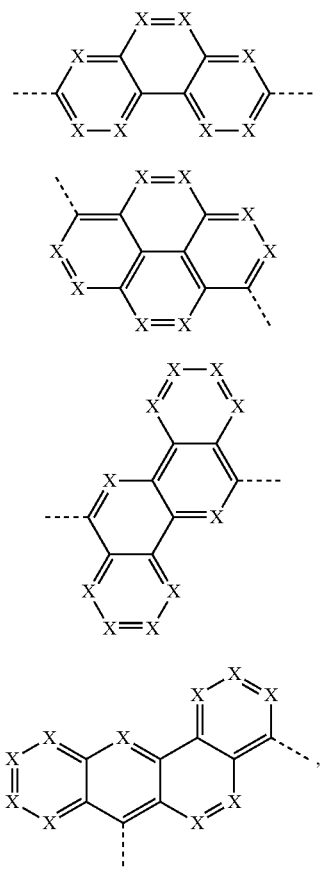

Ar¹-61

Ar¹-62

Ar¹-63

Ar¹-64 where
X is on each occurrence, identically or differently, $CR^4$, $CR^1$ or N, where at least one group X per formula must be equal to $CR^4$;
L is on each occurrence, identically or differently, $C(R^1)_2$, $R^1C=CR^1$, $Si(R^1)_2$, C=O, C=NR¹, O, S, SO, $SO_2$, $PR^1$, $POR^1$ or $NR^1$;
where the groups $R^4$ and $R^1$ are as defined above; and where the two bonds to the radical of the formula (I) are reproduced by the two dashed lines, and where the dashed line on the left denotes the bond from the group Ar¹ to the carbazole group and the dashed line on the right denotes the bond from the group Ar¹ to the nitrogen atom.

The preferred embodiments of the groups X and L mentioned above apply to the groups of the formulae Ar¹-21 to Ar¹-64.

In particular, X in the groups of the formulae Ar¹-21 to Ar¹-64 is preferably equal to $CR^4$ or $CR^1$, where at least one group X per formula must be equal to $CR^4$.

It is particularly preferred for one, two or three groups X in the groups of the formulae Ar¹-21 to Ar¹-64 to be equal to $CR^4$ and for the remaining groups X to be equal to CH. It is very particularly preferred for one or two groups X to be equal to $CR^4$ and for the remaining groups X to be equal to CH. It is even more preferred for precisely one group X to be equal to $CR^4$ and for all other groups X to be equal to CH.

Preferred embodiments of the compounds according to the invention are reproduced by the following formulae (I-1) to (I-12):

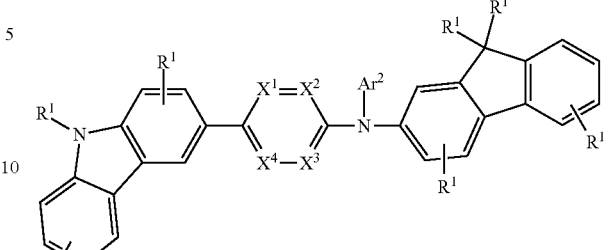

formula (I-1)

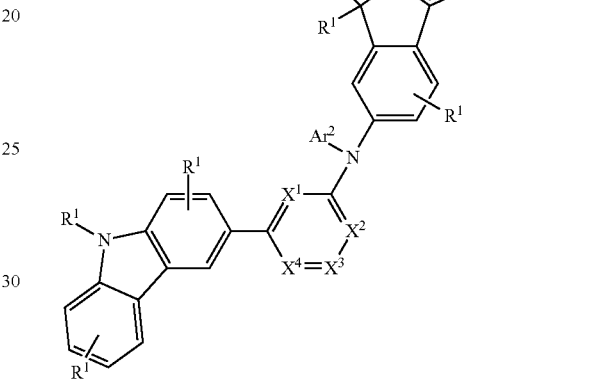

formula (I-2)

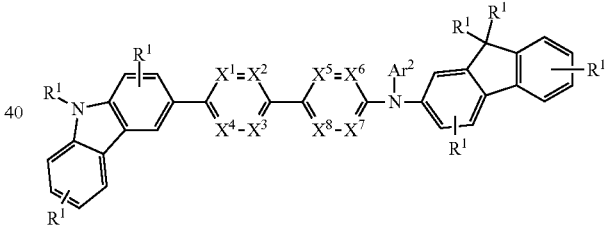

formula (I-3)

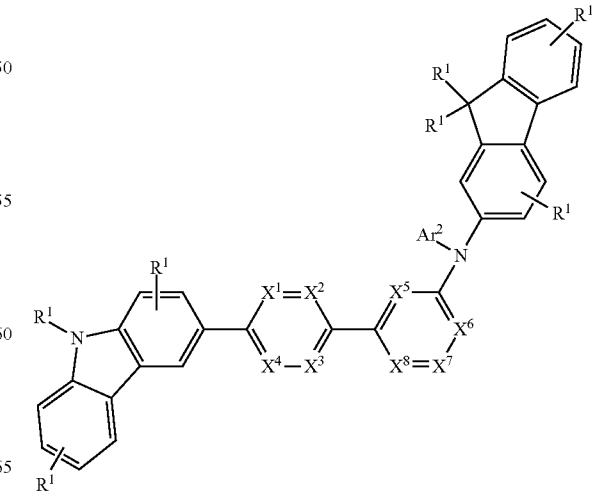

formula (I-4)

formula (I-5)
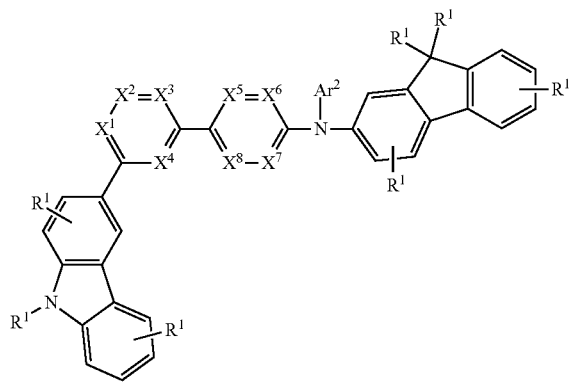
formula (I-8)
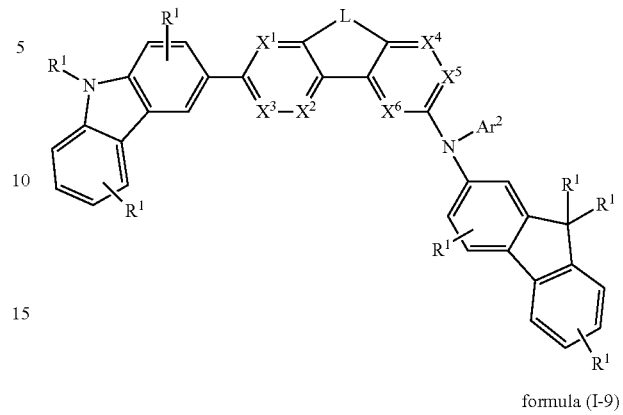
formula (I-9)
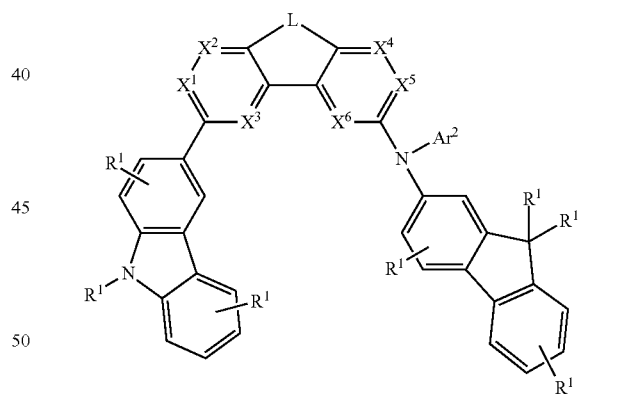
formula (I-6)
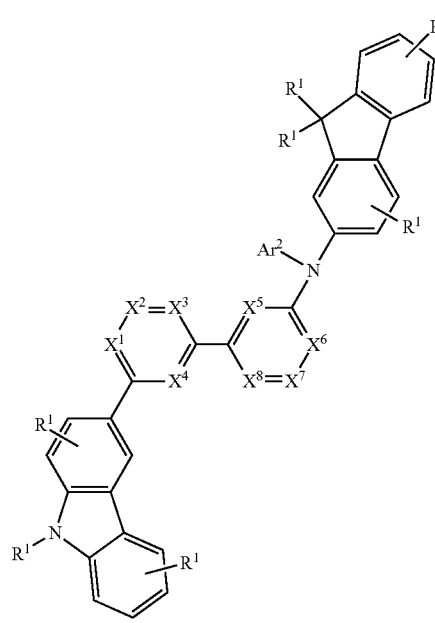
formula (I-10)
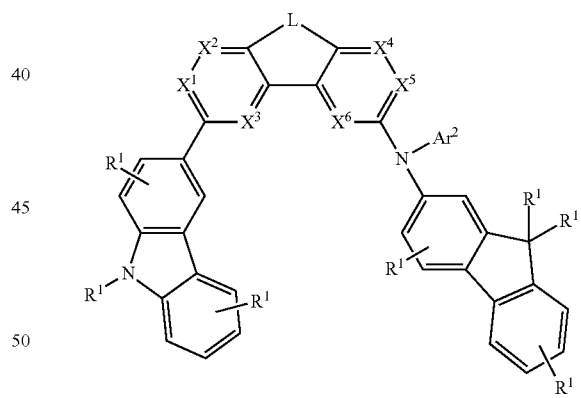
formula (I-7)
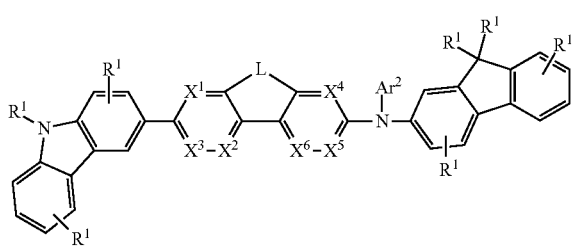
formula (I-11)
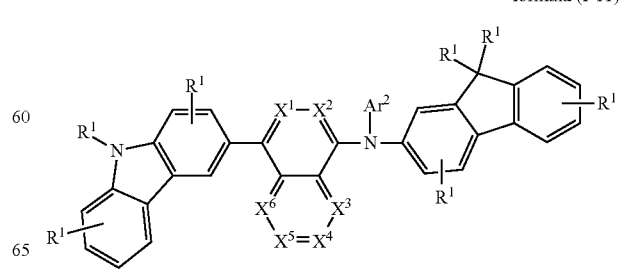

formula (I-12)

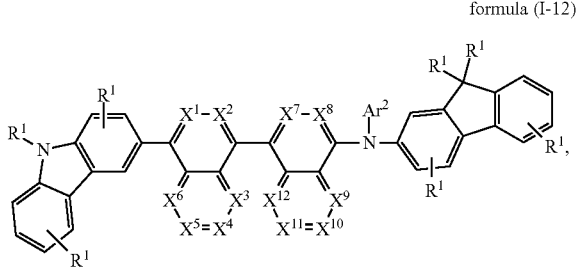

where the symbols occurring are as defined above, and furthermore $X^1$ to $X^{12}$ are selected from $CR^A$ and CH, where at least one of the groups $X^1$ to $X^{12}$ per formula (I-1) to (I-12) is equal to $CR^A$.

Particularly preferred embodiments of the compounds of the formulae (I-1) to (I-12) are reproduced by the following formulae (I-1-1) to (I-12-12), where the groups $X^1$ to $X^{12}$ and L occurring are defined as indicated in the table.

| Comp. | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | L |
|---|---|---|---|---|---|---|---|---|---|---|---|---|---|
| (I-1-1) | $R^A$ | $R^1$ | $R^1$ | $R^1$ | — | — | — | — | — | — | — | — | — |
| (I-1-2) | $R^1$ | $R^A$ | $R^1$ | $R^1$ | — | — | — | — | — | — | — | — | — |
| (I-1-3) | $R^1$ | $R^1$ | $R^A$ | $R^1$ | — | — | — | — | — | — | — | — | — |
| (I-1-4) | $R^1$ | $R^1$ | $R^1$ | $R^A$ | — | — | — | — | — | — | — | — | — |
| (I-2-1) | $R^A$ | $R^1$ | $R^1$ | $R^1$ | — | — | — | — | — | — | — | — | — |
| (I-2-2) | $R^1$ | $R^A$ | $R^1$ | $R^1$ | — | — | — | — | — | — | — | — | — |
| (I-2-3) | $R^1$ | $R^1$ | $R^A$ | $R^1$ | — | — | — | — | — | — | — | — | — |
| (I-2-4) | $R^1$ | $R^1$ | $R^1$ | $R^A$ | — | — | — | — | — | — | — | — | — |
| (I-3-1) | $R^A$ | $R^1$ | $R^1$ | $R^1$ | $R^1$ | $R^1$ | $R^1$ | $R^1$ | — | — | — | — | — |
| (I-3-2) | $R^1$ | $R^A$ | $R^1$ | $R^1$ | $R^1$ | $R^1$ | $R^1$ | $R^1$ | — | — | — | — | — |
| (I-3-3) | $R^1$ | $R^1$ | $R^A$ | $R^1$ | $R^1$ | $R^1$ | $R^1$ | $R^1$ | — | — | — | — | — |
| (I-3-4) | $R^1$ | $R^1$ | $R^1$ | $R^A$ | $R^1$ | $R^1$ | $R^1$ | $R^1$ | — | — | — | — | — |
| (I-3-5) | $R^1$ | $R^1$ | $R^1$ | $R^1$ | $R^A$ | $R^1$ | $R^1$ | $R^1$ | — | — | — | — | — |
| (I-3-6) | $R^1$ | $R^1$ | $R^1$ | $R^1$ | $R^1$ | $R^A$ | $R^1$ | $R^1$ | — | — | — | — | — |
| (I-3-7) | $R^1$ | $R^1$ | $R^1$ | $R^1$ | $R^1$ | $R^1$ | $R^A$ | $R^1$ | — | — | — | — | — |
| (I-3-8) | $R^1$ | $R^1$ | $R^1$ | $R^1$ | $R^1$ | $R^1$ | $R^1$ | $R^A$ | — | — | — | — | — |
| (I-4-1) | $R^A$ | $R^1$ | $R^1$ | $R^1$ | $R^1$ | $R^1$ | $R^1$ | $R^1$ | — | — | — | — | — |
| (I-4-2) | $R^1$ | $R^A$ | $R^1$ | $R^1$ | $R^1$ | $R^1$ | $R^1$ | $R^1$ | — | — | — | — | — |
| (I-4-3) | $R^1$ | $R^1$ | $R^A$ | $R^1$ | $R^1$ | $R^1$ | $R^1$ | $R^1$ | — | — | — | — | — |
| (I-4-4) | $R^1$ | $R^1$ | $R^1$ | $R^A$ | $R^1$ | $R^1$ | $R^1$ | $R^1$ | — | — | — | — | — |
| (I-4-5) | $R^1$ | $R^1$ | $R^1$ | $R^1$ | $R^A$ | $R^1$ | $R^1$ | $R^1$ | — | — | — | — | — |
| (I-4-6) | $R^1$ | $R^1$ | $R^1$ | $R^1$ | $R^1$ | $R^A$ | $R^1$ | $R^1$ | — | — | — | — | — |
| (I-4-7) | $R^1$ | $R^1$ | $R^1$ | $R^1$ | $R^1$ | $R^1$ | $R^A$ | $R^1$ | — | — | — | — | — |
| (I-4-8) | $R^1$ | $R^1$ | $R^1$ | $R^1$ | $R^1$ | $R^1$ | $R^1$ | $R^A$ | — | — | — | — | — |
| (I-5-1) | $R^A$ | $R^1$ | $R^1$ | $R^1$ | $R^1$ | $R^1$ | $R^1$ | $R^1$ | — | — | — | — | — |
| (I-5-2) | $R^1$ | $R^A$ | $R^1$ | $R^1$ | $R^1$ | $R^1$ | $R^1$ | $R^1$ | — | — | — | — | — |
| (I-5-3) | $R^1$ | $R^1$ | $R^A$ | $R^1$ | $R^1$ | $R^1$ | $R^1$ | $R^1$ | — | — | — | — | — |
| (I-5-4) | $R^1$ | $R^1$ | $R^1$ | $R^A$ | $R^1$ | $R^1$ | $R^1$ | $R^1$ | — | — | — | — | — |
| (I-5-5) | $R^1$ | $R^1$ | $R^1$ | $R^1$ | $R^A$ | $R^1$ | $R^1$ | $R^1$ | — | — | — | — | — |
| (I-5-6) | $R^1$ | $R^1$ | $R^1$ | $R^1$ | $R^1$ | $R^A$ | $R^1$ | $R^1$ | — | — | — | — | — |
| (I-5-7) | $R^1$ | $R^1$ | $R^1$ | $R^1$ | $R^1$ | $R^1$ | $R^A$ | $R^1$ | — | — | — | — | — |
| (I-5-8) | $R^1$ | $R^1$ | $R^1$ | $R^1$ | $R^1$ | $R^1$ | $R^1$ | $R^A$ | — | — | — | — | — |
| (I-6-1) | $R^A$ | $R^1$ | $R^1$ | $R^1$ | $R^1$ | $R^1$ | $R^1$ | $R^1$ | — | — | — | — | — |
| (I-6-2) | $R^1$ | $R^A$ | $R^1$ | $R^1$ | $R^1$ | $R^1$ | $R^1$ | $R^1$ | — | — | — | — | — |
| (I-6-3) | $R^1$ | $R^1$ | $R^A$ | $R^1$ | $R^1$ | $R^1$ | $R^1$ | $R^1$ | — | — | — | — | — |
| (I-6-4) | $R^1$ | $R^1$ | $R^1$ | $R^A$ | $R^1$ | $R^1$ | $R^1$ | $R^1$ | — | — | — | — | — |
| (I-6-5) | $R^1$ | $R^1$ | $R^1$ | $R^1$ | $R^A$ | $R^1$ | $R^1$ | $R^1$ | — | — | — | — | — |
| (I-6-6) | $R^1$ | $R^1$ | $R^1$ | $R^1$ | $R^1$ | $R^A$ | $R^1$ | $R^1$ | — | — | — | — | — |
| (I-6-7) | $R^1$ | $R^1$ | $R^1$ | $R^1$ | $R^1$ | $R^1$ | $R^A$ | $R^1$ | — | — | — | — | — |
| (I-6-8) | $R^1$ | $R^1$ | $R^1$ | $R^1$ | $R^1$ | $R^1$ | $R^1$ | $R^A$ | — | — | — | — | — |
| (I-7-1) | $R^A$ | $R^1$ | $R^1$ | $R^1$ | $R^1$ | $R^1$ | — | — | — | — | — | — | $C(R^1)_2$ |
| (I-7-2) | $R^1$ | $R^A$ | $R^1$ | $R^1$ | $R^1$ | $R^1$ | — | — | — | — | — | — | $C(R^1)_2$ |
| (I-7-3) | $R^1$ | $R^1$ | $R^A$ | $R^1$ | $R^1$ | $R^1$ | — | — | — | — | — | — | $C(R^1)_2$ |
| (I-7-4) | $R^1$ | $R^1$ | $R^1$ | $R^A$ | $R^1$ | $R^1$ | — | — | — | — | — | — | $C(R^1)_2$ |
| (I-7-5) | $R^1$ | $R^1$ | $R^1$ | $R^1$ | $R^A$ | $R^1$ | — | — | — | — | — | — | $C(R^1)_2$ |
| (I-7-6) | $R^1$ | $R^1$ | $R^1$ | $R^1$ | $R^1$ | $R^A$ | — | — | — | — | — | — | $C(R^1)_2$ |
| (I-7-7) | $R^A$ | $R^1$ | $R^1$ | $R^1$ | $R^1$ | $R^1$ | — | — | — | — | — | — | C=O |
| (I-7-8) | $R^1$ | $R^A$ | $R^1$ | $R^1$ | $R^1$ | $R^1$ | — | — | — | — | — | — | C=O |
| (I-7-9) | $R^1$ | $R^1$ | $R^A$ | $R^1$ | $R^1$ | $R^1$ | — | — | — | — | — | — | C=O |
| (I-7-10) | $R^1$ | $R^1$ | $R^1$ | $R^A$ | $R^1$ | $R^1$ | — | — | — | — | — | — | C=O |
| (I-7-11) | $R^1$ | $R^1$ | $R^1$ | $R^1$ | $R^A$ | $R^1$ | — | — | — | — | — | — | C=O |
| (I-7-12) | $R^1$ | $R^1$ | $R^1$ | $R^1$ | $R^1$ | $R^A$ | — | — | — | — | — | — | C=O |
| (I-7-13) | $R^A$ | $R^1$ | $R^1$ | $R^1$ | $R^1$ | $R^1$ | — | — | — | — | — | — | O |
| (I-7-14) | $R^1$ | $R^A$ | $R^1$ | $R^1$ | $R^1$ | $R^1$ | — | — | — | — | — | — | O |
| (I-7-15) | $R^1$ | $R^1$ | $R^A$ | $R^1$ | $R^1$ | $R^1$ | — | — | — | — | — | — | O |
| (I-7-16) | $R^1$ | $R^1$ | $R^1$ | $R^A$ | $R^1$ | $R^1$ | — | — | — | — | — | — | O |
| (I-7-17) | $R^1$ | $R^1$ | $R^1$ | $R^1$ | $R^A$ | $R^1$ | — | — | — | — | — | — | O |
| (I-7-18) | $R^1$ | $R^1$ | $R^1$ | $R^1$ | $R^1$ | $R^A$ | — | — | — | — | — | — | O |
| (I-7-19) | $R^A$ | $R^1$ | $R^1$ | $R^1$ | $R^1$ | $R^1$ | — | — | — | — | — | — | S |
| (I-7-20) | $R^1$ | $R^A$ | $R^1$ | $R^1$ | $R^1$ | $R^1$ | — | — | — | — | — | — | S |
| (I-7-21) | $R^1$ | $R^1$ | $R^A$ | $R^1$ | $R^1$ | $R^1$ | — | — | — | — | — | — | S |
| (I-7-22) | $R^1$ | $R^1$ | $R^1$ | $R^A$ | $R^1$ | $R^1$ | — | — | — | — | — | — | S |
| (I-7-23) | $R^1$ | $R^1$ | $R^1$ | $R^1$ | $R^A$ | $R^1$ | — | — | — | — | — | — | S |
| (I-7-24) | $R^1$ | $R^1$ | $R^1$ | $R^1$ | $R^1$ | $R^A$ | — | — | — | — | — | — | S |
| (I-7-25) | $R^A$ | $R^1$ | $R^1$ | $R^1$ | $R^1$ | $R^1$ | — | — | — | — | — | — | $NR^1$ |
| (I-7-26) | $R^1$ | $R^A$ | $R^1$ | $R^1$ | $R^1$ | $R^1$ | — | — | — | — | — | — | $NR^1$ |
| (I-7-27) | $R^1$ | $R^1$ | $R^A$ | $R^1$ | $R^1$ | $R^1$ | — | — | — | — | — | — | $NR^1$ |
| (I-7-28) | $R^1$ | $R^1$ | $R^1$ | $R^A$ | $R^1$ | $R^1$ | — | — | — | — | — | — | $NR^1$ |
| (I-7-29) | $R^1$ | $R^1$ | $R^1$ | $R^1$ | $R^A$ | $R^1$ | — | — | — | — | — | — | $NR^1$ |
| (I-7-30) | $R^1$ | $R^1$ | $R^1$ | $R^1$ | $R^1$ | $R^A$ | — | — | — | — | — | — | $NR^1$ |
| (I-8-1) | $R^A$ | $R^1$ | $R^1$ | $R^1$ | $R^1$ | $R^1$ | — | — | — | — | — | — | $C(R^1)_2$ |
| (I-8-2) | $R^1$ | $R^A$ | $R^1$ | $R^1$ | $R^1$ | $R^1$ | — | — | — | — | — | — | $C(R^1)_2$ |
| (I-8-3) | $R^1$ | $R^1$ | $R^A$ | $R^1$ | $R^1$ | $R^1$ | — | — | — | — | — | — | $C(R^1)_2$ |
| (I-8-4) | $R^1$ | $R^1$ | $R^1$ | $R^A$ | $R^1$ | $R^1$ | — | — | — | — | — | — | $C(R^1)_2$ |
| (I-8-5) | $R^1$ | $R^1$ | $R^1$ | $R^1$ | $R^A$ | $R^1$ | — | — | — | — | — | — | $C(R^1)_2$ |
| (I-8-6) | $R^1$ | $R^1$ | $R^1$ | $R^1$ | $R^1$ | $R^A$ | — | — | — | — | — | — | $C(R^1)_2$ |
| (I-8-7) | $R^A$ | $R^1$ | $R^1$ | $R^1$ | $R^1$ | $R^1$ | — | — | — | — | — | — | C=O |
| (I-8-8) | $R^1$ | $R^A$ | $R^1$ | $R^1$ | $R^1$ | $R^1$ | — | — | — | — | — | — | C=O |
| (I-8-9) | $R^1$ | $R^1$ | $R^A$ | $R^1$ | $R^1$ | $R^1$ | — | — | — | — | — | — | C=O |
| (I-8-10) | $R^1$ | $R^1$ | $R^1$ | $R^A$ | $R^1$ | $R^1$ | — | — | — | — | — | — | C=O |
| (I-8-11) | $R^1$ | $R^1$ | $R^1$ | $R^1$ | $R^A$ | $R^1$ | — | — | — | — | — | — | C=O |
| (I-8-12) | $R^1$ | $R^1$ | $R^1$ | $R^1$ | $R^1$ | $R^A$ | — | — | — | — | — | — | C=O |
| (I-8-13) | $R^A$ | $R^1$ | $R^1$ | $R^1$ | $R^1$ | $R^1$ | — | — | — | — | — | — | O |
| (I-8-14) | $R^1$ | $R^A$ | $R^1$ | $R^1$ | $R^1$ | $R^1$ | — | — | — | — | — | — | O |
| (I-8-15) | $R^1$ | $R^1$ | $R^A$ | $R^1$ | $R^1$ | $R^1$ | — | — | — | — | — | — | O |
| (I-8-16) | $R^1$ | $R^1$ | $R^1$ | $R^A$ | $R^1$ | $R^1$ | — | — | — | — | — | — | O |
| (I-8-17) | $R^1$ | $R^1$ | $R^1$ | $R^1$ | $R^A$ | $R^1$ | — | — | — | — | — | — | O |
| (I-7-18) | $R^1$ | $R^1$ | $R^1$ | $R^1$ | $R^1$ | $R^A$ | — | — | — | — | — | — | O |
| (I-8-19) | $R^A$ | $R^1$ | $R^1$ | $R^1$ | $R^1$ | $R^1$ | — | — | — | — | — | — | S |
| (I-8-20) | $R^1$ | $R^A$ | $R^1$ | $R^1$ | $R^1$ | $R^1$ | — | — | — | — | — | — | S |
| (I-8-21) | $R^1$ | $R^1$ | $R^A$ | $R^1$ | $R^1$ | $R^1$ | — | — | — | — | — | — | S |
| (I-8-22) | $R^1$ | $R^1$ | $R^1$ | $R^A$ | $R^1$ | $R^1$ | — | — | — | — | — | — | S |
| (I-8-23) | $R^1$ | $R^1$ | $R^1$ | $R^1$ | $R^A$ | $R^1$ | — | — | — | — | — | — | S |
| (I-8-24) | $R^1$ | $R^1$ | $R^1$ | $R^1$ | $R^1$ | $R^A$ | — | — | — | — | — | — | S |
| (I-8-25) | $R^A$ | $R^1$ | $R^1$ | $R^1$ | $R^1$ | $R^1$ | — | — | — | — | — | — | $NR^1$ |
| (I-8-26) | $R^1$ | $R^A$ | $R^1$ | $R^1$ | $R^1$ | $R^1$ | — | — | — | — | — | — | $NR^1$ |
| (I-8-27) | $R^1$ | $R^1$ | $R^A$ | $R^1$ | $R^1$ | $R^1$ | — | — | — | — | — | — | $NR^1$ |
| (I-8-28) | $R^1$ | $R^1$ | $R^1$ | $R^A$ | $R^1$ | $R^1$ | — | — | — | — | — | — | $NR^1$ |
| (I-8-29) | $R^1$ | $R^1$ | $R^1$ | $R^1$ | $R^A$ | $R^1$ | — | — | — | — | — | — | $NR^1$ |
| (I-8-30) | $R^1$ | $R^1$ | $R^1$ | $R^1$ | $R^1$ | $R^A$ | — | — | — | — | — | — | $NR^1$ |
| (I-9-1) | $R^A$ | $R^1$ | $R^1$ | $R^1$ | $R^1$ | $R^1$ | — | — | — | — | — | — | $C(R^1)_2$ |
| (I-9-2) | $R^1$ | $R^A$ | $R^1$ | $R^1$ | $R^1$ | $R^1$ | — | — | — | — | — | — | $C(R^1)_2$ |
| (I-9-3) | $R^1$ | $R^1$ | $R^A$ | $R^1$ | $R^1$ | $R^1$ | — | — | — | — | — | — | $C(R^1)_2$ |
| (I-9-4) | $R^1$ | $R^1$ | $R^1$ | $R^A$ | $R^1$ | $R^1$ | — | — | — | — | — | — | $C(R^1)_2$ |
| (I-9-5) | $R^1$ | $R^1$ | $R^1$ | $R^1$ | $R^A$ | $R^1$ | — | — | — | — | — | — | $C(R^1)_2$ |
| (I-9-6) | $R^1$ | $R^1$ | $R^1$ | $R^1$ | $R^1$ | $R^A$ | — | — | — | — | — | — | $C(R^1)_2$ |
| (I-9-7) | $R^A$ | $R^1$ | $R^1$ | $R^1$ | $R^1$ | $R^1$ | — | — | — | — | — | — | C=O |
| (I-9-8) | $R^1$ | $R^A$ | $R^1$ | $R^1$ | $R^1$ | $R^1$ | — | — | — | — | — | — | C=O |
| (I-9-9) | $R^1$ | $R^1$ | $R^A$ | $R^1$ | $R^1$ | $R^1$ | — | — | — | — | — | — | C=O |
| (I-9-10) | $R^1$ | $R^1$ | $R^1$ | $R^A$ | $R^1$ | $R^1$ | — | — | — | — | — | — | C=O |
| (I-9-11) | $R^1$ | $R^1$ | $R^1$ | $R^1$ | $R^A$ | $R^1$ | — | — | — | — | — | — | C=O |
| (I-9-12) | $R^1$ | $R^1$ | $R^1$ | $R^1$ | $R^1$ | $R^A$ | — | — | — | — | — | — | C=O |
| (I-9-13) | $R^A$ | $R^1$ | $R^1$ | $R^1$ | $R^1$ | $R^1$ | — | — | — | — | — | — | O |
| (I-9-14) | $R^1$ | $R^A$ | $R^1$ | $R^1$ | $R^1$ | $R^1$ | — | — | — | — | — | — | O |
| (I-9-15) | $R^1$ | $R^1$ | $R^A$ | $R^1$ | $R^1$ | $R^1$ | — | — | — | — | — | — | O |
| (I-9-16) | $R^1$ | $R^1$ | $R^1$ | $R^A$ | $R^1$ | $R^1$ | — | — | — | — | — | — | O |
| (I-9-17) | $R^1$ | $R^1$ | $R^1$ | $R^1$ | $R^A$ | $R^1$ | — | — | — | — | — | — | O |
| (I-9-18) | $R^1$ | $R^1$ | $R^1$ | $R^1$ | $R^1$ | $R^A$ | — | — | — | — | — | — | O |
| (I-9-19) | $R^A$ | $R^1$ | $R^1$ | $R^1$ | $R^1$ | $R^1$ | — | — | — | — | — | — | S |
| (I-9-20) | $R^1$ | $R^A$ | $R^1$ | $R^1$ | $R^1$ | $R^1$ | — | — | — | — | — | — | S |
| (I-9-21) | $R^1$ | $R^1$ | $R^A$ | $R^1$ | $R^1$ | $R^1$ | — | — | — | — | — | — | S |
| (I-9-22) | $R^1$ | $R^1$ | $R^1$ | $R^A$ | $R^1$ | $R^1$ | — | — | — | — | — | — | S |
| (I-9-23) | $R^1$ | $R^1$ | $R^1$ | $R^1$ | $R^A$ | $R^1$ | — | — | — | — | — | — | S |
| (I-9-24) | $R^1$ | $R^1$ | $R^1$ | $R^1$ | $R^1$ | $R^A$ | — | — | — | — | — | — | S |
| (I-9-25) | $R^A$ | $R^1$ | $R^1$ | $R^1$ | $R^1$ | $R^1$ | — | — | — | — | — | — | $NR^1$ |
| (I-9-26) | $R^1$ | $R^A$ | $R^1$ | $R^1$ | $R^1$ | $R^1$ | — | — | — | — | — | — | $NR^1$ |
| (I-9-27) | $R^1$ | $R^1$ | $R^A$ | $R^1$ | $R^1$ | $R^1$ | — | — | — | — | — | — | $NR^1$ |
| (I-9-28) | $R^1$ | $R^1$ | $R^1$ | $R^A$ | $R^1$ | $R^1$ | — | — | — | — | — | — | $NR^1$ |

-continued

| Comp. | X¹ | X² | X³ | X⁴ | X⁵ | X⁶ | X⁷ | X⁸ | X⁹ | X¹⁰ | X¹¹ | X¹² | L |
|---|---|---|---|---|---|---|---|---|---|---|---|---|---|
| (I-9-29) | R¹ | R¹ | R¹ | R¹ | R⁴ | R¹ | — | — | — | — | — | — | NR¹ |
| (I-9-30) | R¹ | R¹ | R¹ | R¹ | R¹ | R⁴ | — | — | — | — | — | — | NR¹ |
| (I-10-1) | R⁴ | R¹ | R¹ | R¹ | R¹ | R¹ | — | — | — | — | — | — | C(R¹)₂ |
| (I-10-2) | R¹ | R⁴ | R¹ | R¹ | R¹ | R¹ | — | — | — | — | — | — | C(R¹)₂ |
| (I-10-3) | R¹ | R¹ | R⁴ | R¹ | R¹ | R¹ | — | — | — | — | — | — | C(R¹)₂ |
| (I-10-4) | R¹ | R¹ | R¹ | R⁴ | R¹ | R¹ | — | — | — | — | — | — | C(R¹)₂ |
| (I-10-5) | R¹ | R¹ | R¹ | R¹ | R⁴ | R¹ | — | — | — | — | — | — | C(R¹)₂ |
| (I-10-6) | R¹ | R¹ | R¹ | R¹ | R¹ | R⁴ | — | — | — | — | — | — | C(R¹)₂ |
| (I-10-7) | R⁴ | R¹ | R¹ | R¹ | R¹ | R¹ | — | — | — | — | — | — | C=O |
| (I-10-8) | R¹ | R⁴ | R¹ | R¹ | R¹ | R¹ | — | — | — | — | — | — | C=O |
| (I-10-9) | R¹ | R¹ | R⁴ | R¹ | R¹ | R¹ | — | — | — | — | — | — | C=O |
| (I-10-10) | R¹ | R¹ | R¹ | R⁴ | R¹ | R¹ | — | — | — | — | — | — | C=O |
| (I-10-11) | R¹ | R¹ | R¹ | R¹ | R⁴ | R¹ | — | — | — | — | — | — | C=O |
| (I-10-12) | R¹ | R¹ | R¹ | R¹ | R¹ | R⁴ | — | — | — | — | — | — | C=O |
| (I-10-13) | R⁴ | R¹ | R¹ | R¹ | R¹ | R¹ | — | — | — | — | — | — | O |
| (I-10-14) | R¹ | R⁴ | R¹ | R¹ | R¹ | R¹ | — | — | — | — | — | — | O |
| (I-10-15) | R¹ | R¹ | R⁴ | R¹ | R¹ | R¹ | — | — | — | — | — | — | O |
| (I-10-16) | R¹ | R¹ | R¹ | R⁴ | R¹ | R¹ | — | — | — | — | — | — | O |
| (I-10-17) | R¹ | R¹ | R¹ | R¹ | R⁴ | R¹ | — | — | — | — | — | — | O |
| (I-10-18) | R¹ | R¹ | R¹ | R¹ | R¹ | R⁴ | — | — | — | — | — | — | O |
| (I-10-19) | R⁴ | R¹ | R¹ | R¹ | R¹ | R¹ | — | — | — | — | — | — | S |
| (I-10-20) | R¹ | R⁴ | R¹ | R¹ | R¹ | R¹ | — | — | — | — | — | — | S |
| (I-10-21) | R¹ | R¹ | R⁴ | R¹ | R¹ | R¹ | — | — | — | — | — | — | S |
| (I-10-22) | R¹ | R¹ | R¹ | R⁴ | R¹ | R¹ | — | — | — | — | — | — | S |
| (I-10-23) | R¹ | R¹ | R¹ | R¹ | R⁴ | R¹ | — | — | — | — | — | — | S |
| (I-10-24) | R¹ | R¹ | R¹ | R¹ | R¹ | R⁴ | — | — | — | — | — | — | S |
| (I-10-25) | R⁴ | R¹ | R¹ | R¹ | R¹ | R¹ | — | — | — | — | — | — | NR¹ |
| (I-10-26) | R¹ | R⁴ | R¹ | R¹ | R¹ | R¹ | — | — | — | — | — | — | NR¹ |
| (I-10-27) | R¹ | R¹ | R⁴ | R¹ | R¹ | R¹ | — | — | — | — | — | — | NR¹ |
| (I-10-28) | R¹ | R¹ | R¹ | R⁴ | R¹ | R¹ | — | — | — | — | — | — | NR¹ |
| (I-10-29) | R¹ | R¹ | R¹ | R¹ | R⁴ | R¹ | — | — | — | — | — | — | NR¹ |
| (I-10-30) | R¹ | R¹ | R¹ | R¹ | R¹ | R⁴ | — | — | — | — | — | — | NR¹ |
| (I-11-1) | R⁴ | R¹ | R¹ | R¹ | R¹ | R¹ | — | — | — | — | — | — | — |
| (I-11-2) | R¹ | R⁴ | R¹ | R¹ | R¹ | R¹ | — | — | — | — | — | — | — |
| (I-11-3) | R¹ | R¹ | R⁴ | R¹ | R¹ | R¹ | — | — | — | — | — | — | — |
| (I-11-4) | R¹ | R¹ | R¹ | R⁴ | R¹ | R¹ | — | — | — | — | — | — | — |
| (I-11-5) | R¹ | R¹ | R¹ | R¹ | R⁴ | R¹ | — | — | — | — | — | — | — |
| (I-11-6) | R¹ | R¹ | R¹ | R¹ | R¹ | R⁴ | — | — | — | — | — | — | — |
| (I-12-1) | R⁴ | R¹ | R¹ | R¹ | R¹ | R¹ | R¹ | R¹ | R¹ | R¹ | R¹ | R¹ | — |
| (I-12-2) | R¹ | R⁴ | R¹ | R¹ | R¹ | R¹ | R¹ | R¹ | R¹ | R¹ | R¹ | R¹ | — |
| (I-12-3) | R¹ | R¹ | R⁴ | R¹ | R¹ | R¹ | R¹ | R¹ | R¹ | R¹ | R¹ | R¹ | — |
| (I-12-4) | R¹ | R¹ | R¹ | R⁴ | R¹ | R¹ | R¹ | R¹ | R¹ | R¹ | R¹ | R¹ | — |
| (I-12-5) | R¹ | R¹ | R¹ | R¹ | R⁴ | R¹ | R¹ | R¹ | R¹ | R¹ | R¹ | R¹ | — |
| (I-12-6) | R¹ | R¹ | R¹ | R¹ | R¹ | R⁴ | R¹ | R¹ | R¹ | R¹ | R¹ | R¹ | — |
| (I-12-7) | R¹ | R¹ | R¹ | R¹ | R¹ | R¹ | R⁴ | R¹ | R¹ | R¹ | R¹ | R¹ | — |
| (I-12-8) | R¹ | R¹ | R¹ | R¹ | R¹ | R¹ | R¹ | R⁴ | R¹ | R¹ | R¹ | R¹ | — |
| (I-12-9) | R¹ | R¹ | R¹ | R¹ | R¹ | R¹ | R¹ | R¹ | R⁴ | R¹ | R¹ | R¹ | — |
| (I-12-10) | R¹ | R¹ | R¹ | R¹ | R¹ | R¹ | R¹ | R¹ | R¹ | R⁴ | R¹ | R¹ | — |
| (I-12-11) | R¹ | R¹ | R¹ | R¹ | R¹ | R¹ | R¹ | R¹ | R¹ | R¹ | R⁴ | R¹ | — |
| (I-12-12) | R¹ | R¹ | R¹ | R¹ | R¹ | R¹ | R¹ | R¹ | R¹ | R¹ | R¹ | R⁴ | — |

In general, the following preferred embodiments apply to the compounds according to the invention:

Ar¹ is preferably selected from the preferred embodiments indicated above for the groups Ar¹.

Ar¹ furthermore preferably represents an aryl group having 6 to 18 aromatic ring atoms or a heteroaryl group having 5 to 18 aromatic ring atoms, which is substituted by at least one radical R⁴ and which may furthermore be substituted by one or more radicals R¹. Ar¹ very particularly preferably represents an aryl group having 6 to 14 aromatic ring atoms, which is substituted by at least one radical R⁴ and which may furthermore be substituted by one or more radicals R¹.

Ar² is preferably an aromatic ring system having 6 to 18 aromatic ring atoms or a heteroaromatic ring system having 5 to 18 aromatic ring atoms, which may be substituted by one or more radicals R¹.

Ar² is particularly preferably an aromatic ring system having 6 to 12 aromatic ring atoms, which may be substituted by one or more radicals R¹.

R⁴ is preferably on each occurrence, identically or differently, a straight-chain alkyl or alkoxy group having 1 to 10 C atoms, which may be substituted by one or more radicals R³, or a branched alkyl or alkoxy group having 3 to 10 C atoms, which may be substituted by one or more radicals R³, where one or more adjacent or non-adjacent CH₂ groups in the above-mentioned groups may be replaced by —R³C=CR³—, —C≡C—, Si(R³)₂, C=O, —COO—, NR³, O or S and where one or more H atoms in the above-mentioned groups may be replaced by D, F or CN.

R⁴ is particularly preferably on each occurrence, identically or differently, a straight-chain alkyl group having 1 to 8 C atoms or a branched alkyl group having 3 to 8 C atoms, which may be substituted by one or more radicals R³.

R⁴ is very particularly preferably on each occurrence, identically or differently, methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl or 2,2,2-trifluoroethyl, where the groups mentioned may be substituted at free positions by one or more radicals R³.

In a further preferred embodiment of the invention, one or more radicals R⁴, if Ar¹ contains a plurality of aromatic rings, are bonded to the same aromatic ring to which the nitrogen atom is also bonded. In a particularly preferred embodiment of the invention, a radical R⁴ is bonded to the group Ar¹ in one or both of the positions ortho to the nitrogen.

R¹ is on each occurrence, identically or differently, H, D, F, CN, Si(R³)₃, N(R³)₂ or a straight-chain alkyl or alkoxy group having 1 to 20 C atoms or a branched or cyclic alkyl or alkoxy group having 3 to 20 C atoms, where the above-mentioned groups may each be substituted by one or more radicals R³ and where one or more adjacent or non-adjacent CH₂ groups in the above-mentioned groups may be replaced by —C≡C—, —R³C=CR³—, Si(R³)₂, C=O, C=NR³, —NR³—, —O—, —S—, —COO— or —CONR³—, or an aromatic or heteroaromatic ring system having 5 to 20 aromatic ring atoms, which may in each case be substituted by one or more radicals R³, where two or more radicals R¹ may be linked to one another and may form an aliphatic or aromatic ring.

In a particularly preferred embodiment of the invention, R¹ bonded to the nitrogen of the carbazole moiety of formula (1) is an aromatic ring system having 6 to 18 aromatic ring atoms, which may in each case be substituted by one or more radicals R³, or a heteroaromatic ring system having 5 to 18 aromatic ring atoms, which may in each case be substituted by one or more radicals R³. Very particularly preferably, R¹ bonded to the nitrogen of the carbazole moiety of formula (1) is an aromatic ring system having 6 to 12 aromatic ring atoms, which may be substituted by one or more radicals R³.

It is preferred in accordance with the invention for the said preferred embodiments of the groups Ar², R⁴, and R¹ to occur in combination with the preferred embodiments of the formulae (I-1-1) to (I-12-12).

Furthermore, however, the present invention also relates to all other combinations of the above-mentioned preferred and general embodiments of chemical groups and formulae.

Examples of compounds according to the invention are given in the following table.

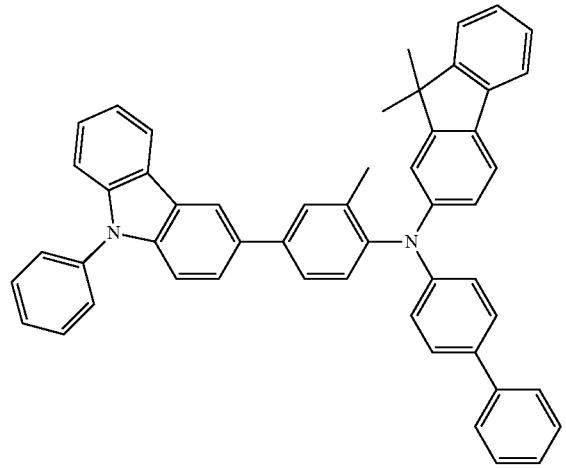 [SMILES: Cc1cc(-c2ccc3c(c2)c2ccccc2n3-c2ccccc2)ccc1N(c1ccc(-c2ccccc2)cc1)c1ccc2c(c1)C(C)(C)c1ccccc1-2]

1

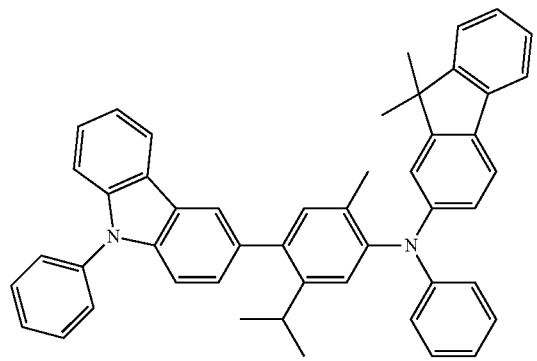 [SMILES: Cc1cc(-c2ccc3c(c2)c2ccccc2n3-c2ccccc2)c(C(C)C)cc1N(c1ccccc1)c1ccc2c(c1)C(C)(C)c1ccccc1-2]

2

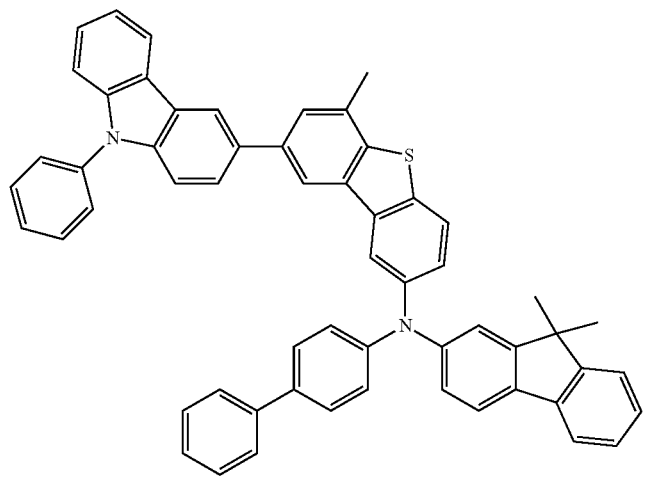 [SMILES: Cc1cc(-c2ccc3c(c2)c2ccccc2n3-c2ccccc2)cc2c1sc1ccc(N(c3ccc(-c4ccccc4)cc3)c3ccc4c(c3)C(C)(C)c3ccccc3-4)cc12]

3

-continued
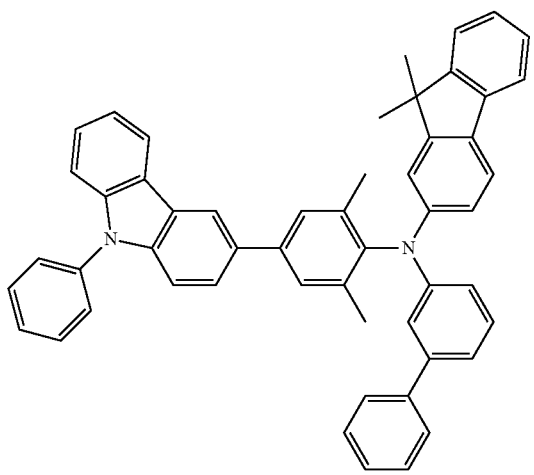 [SMILES: Cc1cc(-c2ccc3c(c2)c2ccccc2n3-c2ccccc2)cc(C)c1N(c1cccc(-c2ccccc2)c1)c1ccc2c(c1)C(C)(C)c1ccccc1-2]
4
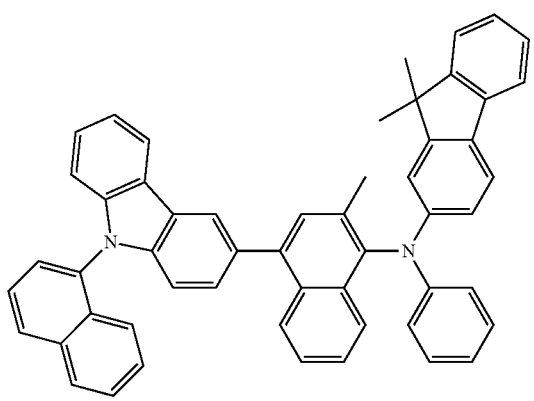 [SMILES: Cc1cc(-c2ccc3c(c2)c2ccccc2n3-c2cccc3ccccc23)c2ccccc2c1N(c1ccccc1)c1ccc2c(c1)C(C)(C)c1ccccc1-2]
5
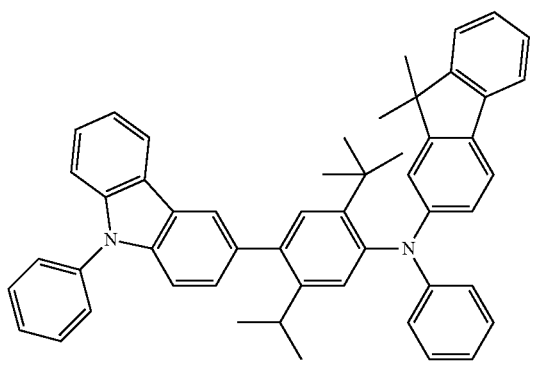 [SMILES: CC(C)c1cc(N(c2ccccc2)c2ccc3c(c2)C(C)(C)c2ccccc2-3)c(C(C)(C)C)cc1-c1ccc2c(c1)c1ccccc1n2-c1ccccc1]
6
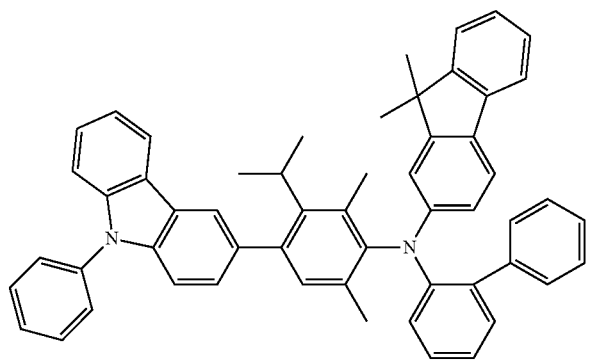 [SMILES: Cc1cc(-c2ccc3c(c2)c2ccccc2n3-c2ccccc2)c(C(C)C)c(C)c1N(c1ccc2c(c1)C(C)(C)c1ccccc1-2)c1ccccc1-c1ccccc1]
7

The compounds of the formula (I) according to the invention can be prepared by known organochemical synthetic processes. These include, for example, bromination, Suzuki coupling and Hartwig-Buchwald coupling, inter alia.

The person skilled in the art in the area of organic synthesis and in the area of functional materials for organic electroluminescent devices will be able to deviate from the illustrative synthetic routes shown below and/or modify individual steps in a suitable manner if such action is advantageous.

Compounds of the formula (I) according to the invention can be prepared, for example, as shown in Scheme 1 below.

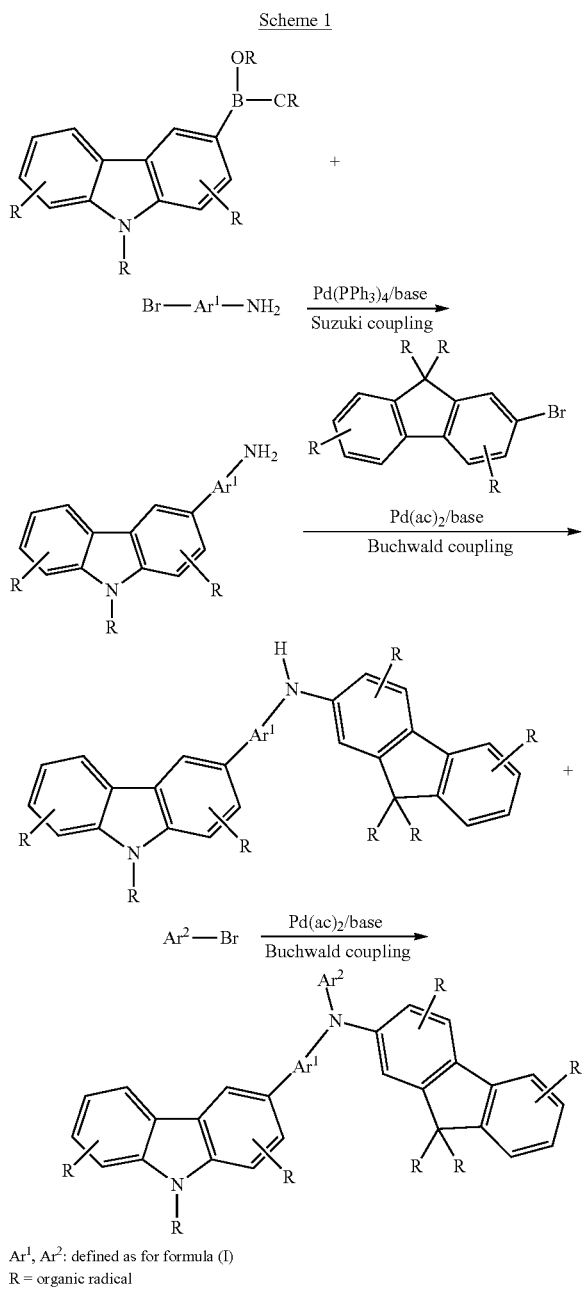

Ar¹, Ar²: defined as for formula (I)
R = organic radical

To this end, firstly a carbazolylboronic acid derivative is reacted with the unit Ar¹ in a Suzuki coupling. A Buchwald coupling to the amine function of the group Ar¹ is subsequently carried out, with introduction of the fluorene derivative. Finally, the bridging secondary amine group is arylated in a further Buchwald coupling, giving a compound of the formula (I). The said reactions may be followed by further functionalisation and derivatisation steps.

The invention thus furthermore relates to a process for the preparation of a compound of the formula (I), characterised in that the group Ar¹ is reacted with a carbazole derivative and with a fluorene derivative by one or more organometallic coupling reactions.

According to a preferred embodiment, the group Ar¹ is firstly coupled to the carbazole derivative, subsequently reacted with the fluorene derivative, and the resultant intermediate is finally arylated on the nitrogen atom which is bonded to the group Ar¹, where all steps represent organometallic coupling reactions.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers containing one or more compounds of the formula (I), where the bond(s) to the polymer, oligomer or dendrimer may be localised at any desired positions substituted by $R^1$ in formula (I). Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of this invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

For the recurring units of the formula (I) in oligomers, dendrimers and polymers, the same preferences apply as described above for compounds of the formula (I).

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006,383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017, 066) or also a plurality of these units. The polymers, oligomers and dendrimers usually also contain further units, for example emitting (fluorescent or phosphorescent) units, such as, for example, vinyltriarylamines (for example in accordance with WO 07/068,325) or phosphorescent metal complexes (for example in accordance with WO 06/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N linking are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 03/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterisation of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The invention also relates to formulations comprising at least one compound of the formula (I) or at least one polymer, oligomer or dendrimer containing at least one unit of the formula (I) and at least one solvent, preferably an organic solvent.

The formulations according to the invention are used, for example, in the production of organic electroluminescent devices, which is described in greater detail in a section below.

The compounds of the formula (I) according to the invention are suitable for use in electronic devices, in particular in organic electroluminescent devices (OLEDs). Depending on the substitution, the compounds are employed in different functions and in different layers of the organic electroluminescent device.

For example, compounds of the formula (I) which contain electron-deficient groups, such as six-membered heteroaryl rings having one, preferably a number of, nitrogen atom(s) or five-membered heteroaryl rings having two or more nitrogen atoms, are particularly suitable for use as matrix material for phosphorescent dopants.

Compounds of the formula (I) which are substituted by aromatic ring systems, in particular by aromatic ring systems having 12 to 30 aromatic ring atoms, are furthermore particularly suitable, for example, for use as hole-transport materials or as fluorescent dopants.

The compounds according to the invention are preferably employed as hole-transport material in a hole-transport layer or as matrix material in an emitting layer comprising one or more phosphorescent dopants. However, they can also be employed in other layers and/or functions, in particular as fluorescent dopants in an emitting layer or as hole- or electron-blocking materials.

The invention therefore furthermore relates to the use of the compounds of the formula (I) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

Particular preference is given to organic electroluminescent devices comprising an anode, a cathode and at least one emitting layer, characterised in that at least one organic layer, which may be an emitting layer, a hole-transport layer or another layer, comprises at least one compound of the formula (I).

Apart from the cathode, the anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*), coupling-out layers and/or organic or inorganic p/n junctions. However, it should be pointed out that each of these layers does not necessarily have to be present, and the choice of the layers is always dependent on the compounds used and in particular also on whether the device is a fluorescent or phosphorescent electroluminescent device.

The organic electroluminescent device may also comprise a plurality of emitting layers. These emitting layers in this case particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where one or more of these layers may comprise a compound of the formula (I) and where the three layers exhibit blue, green and orange or red emission (for the basic structure see, for example, WO 05/011013). Emitters which have broad-band emission bands and thus exhibit white emission are likewise suitable for white emission. In the case of the present invention, the compounds according to the invention are preferably present in the hole-transport layer in the devices described above.

It is preferred in accordance with the invention for the compound of the formula (I) to be employed in an electronic device comprising one or more phosphorescent dopants. The compound here can be used in various layers, preferably in a hole-transport layer, a hole-injection layer or in the emitting layer.

However, the compound of the formula (I) can also be employed in accordance with the invention in an electronic device comprising one or more fluorescent dopants and no phosphorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or Cu.

For the purposes of the present invention, all luminescent iridium, platinum or copper complexes are regarded as being phosphorescent compounds.

Examples of the phosphorescent dopants described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes, without inventive step, in combination with the compounds of the formula (I) according to the invention in organic electroluminescent devices.

Further examples of suitable phosphorescent dopants are evident from the table following in a later section.

In a preferred embodiment of the invention, the compounds of the formula (I) are employed as hole-transport material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. The hole-transport layer may be directly adjacent to the emission layer. If the compounds of the formula (I) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I) is used as hole-transport material in combination with a hexaazatriphenylene derivative, as described in US 2007/0092755. The hexaazatriphenylene derivative is particularly preferably employed in its own layer here.

If the compound of the formula (I) is employed as hole-transport material in a hole-transport layer, the compound can be employed as pure material, i.e. in a proportion of 100% in the hole-transport layer, or it can be employed in combination with one or more further compounds in the hole-transport layer.

In a further embodiment of the present invention, the compounds of the formula (I) are employed as matrix material in combination with one or more dopants, preferably phosphorescent dopants.

A dopant is taken to mean the component whose proportion in the mixture is the smaller in a system comprising a matrix material and a dopant. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (I) are used as a component of mixed matrix systems. The mixed matrix systems preferably comprise two or three different matrix materials, particularly preferably two different matrix materials. The two different matrix materials here may be present in a ratio of 1:10 to 1:1, preferably in a ratio of 1:4 to 1:1. The mixed matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed matrix systems are preferably employed in phosphorescent organic electroluminescent devices.

Particularly suitable matrix materials, which can be employed in combination with the compounds according to the invention as matrix components of a mixed matrix system, are aromatic ketones, aromatic phosphine oxides or aromatic sulfoxides or sulfones, for example in accordance with WO 04/013080, WO 04/093207, WO 06/005627 or WO 2010/006680, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with WO 2010/015306, WO 07/063,754 or WO 08/056,746, zinc complexes, for example in accordance with EP 652273 or WO 09/062,578, diazasilole or tetraazasilole derivatives, for example in accordance with WO 2010/054729, diazaphosphole derivatives, for example in accordance with WO 2010/054730, or indenocarbazole derivatives, for example in accordance with WO 2010/136109, or bridged carbazole derivatives, for example in accordance with WO 2011/088877 and WO 2011/128017.

Preferred phosphorescent dopants for use in mixed matrix systems comprising the compounds according to the invention are the phosphorescent dopants mentioned in the following table.

In a further embodiment of the invention, the compounds of the formula (I) are employed as emitting materials in an emitting layer. In this case, the compounds according to the invention are particularly preferably used as green or blue emitters.

Preferred matrix materials for use in combination with the compounds according to the invention as fluorescent emitters are mentioned in one of the following sections.

The functional materials preferably employed in the electronic devices comprising one or more compounds according to the invention according to the invention are indicated below.

Particularly suitable phosphorescent dopants are the compounds indicated in the following table.

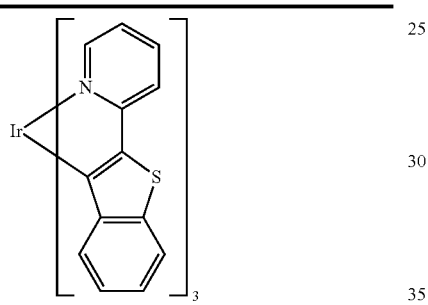

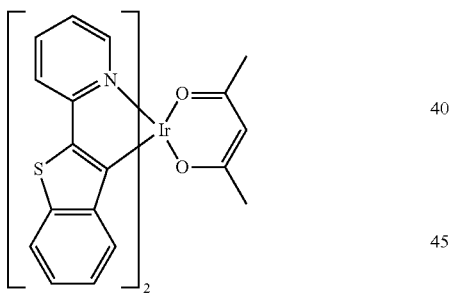

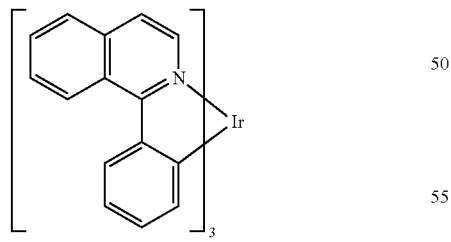

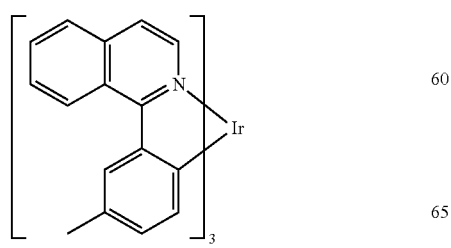

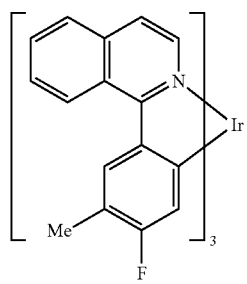

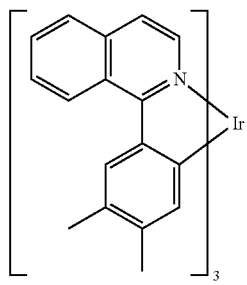

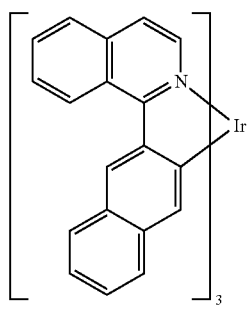

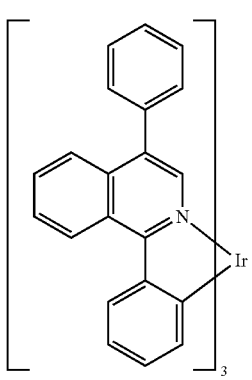

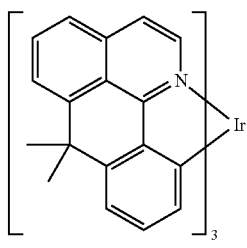

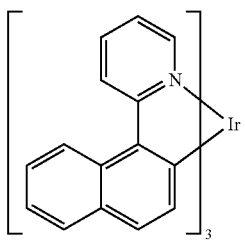
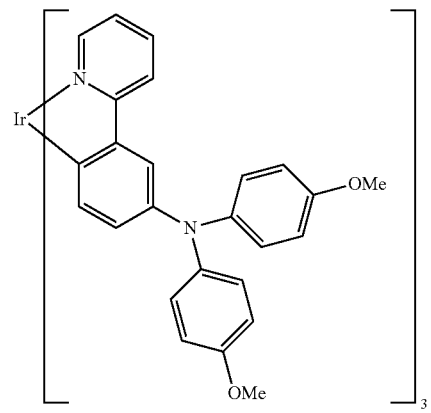
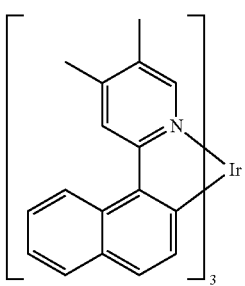
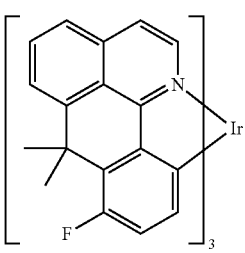
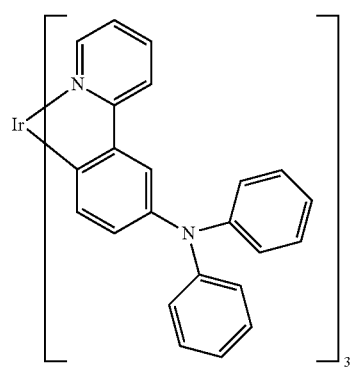
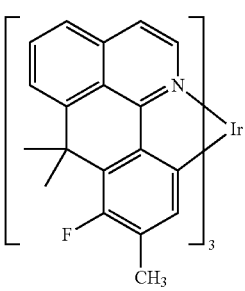
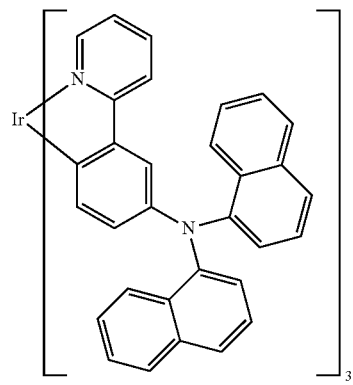
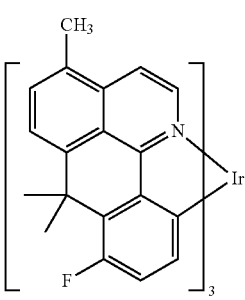
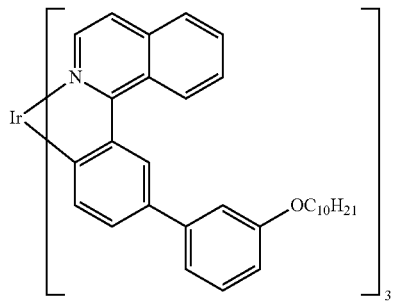

-continued
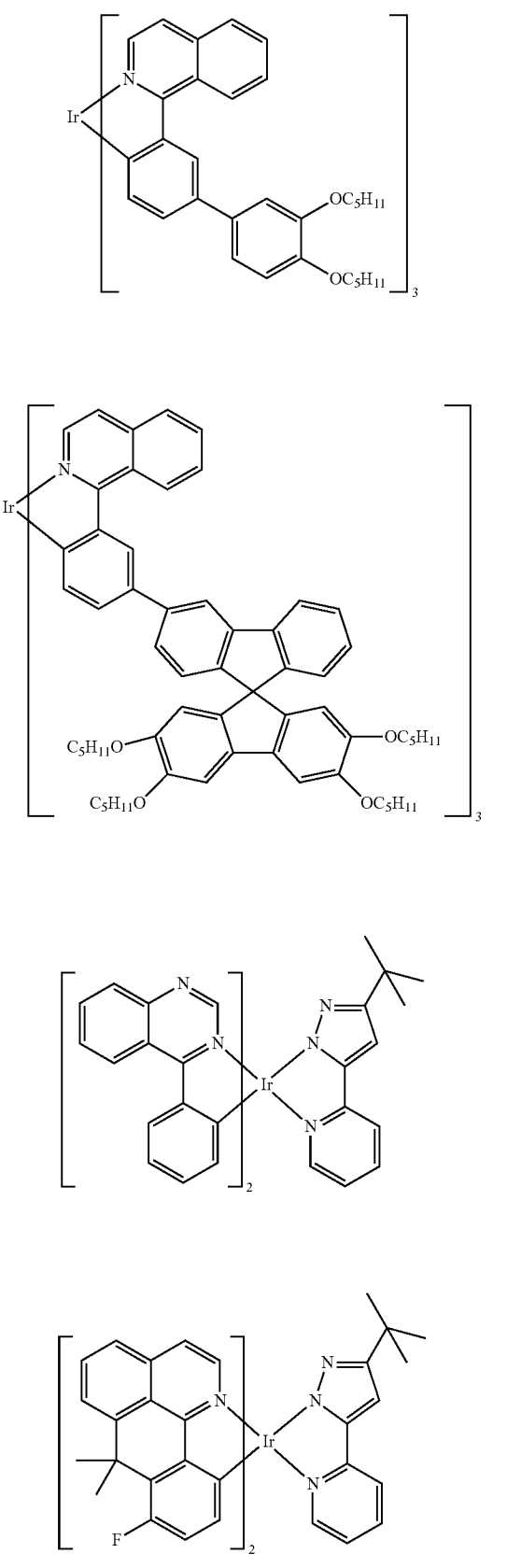
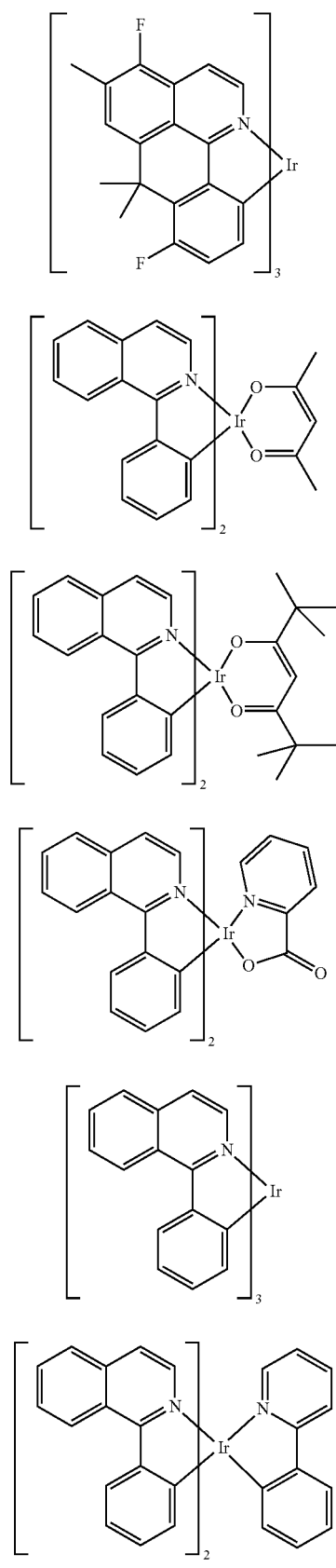

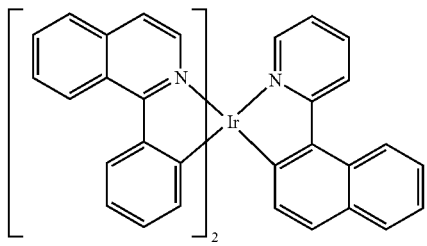
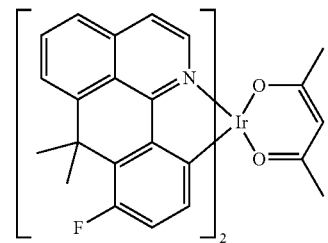
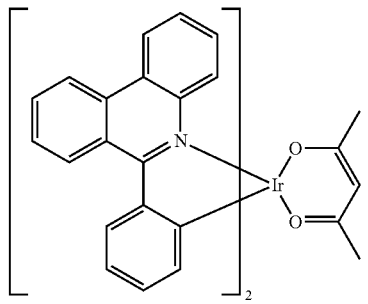
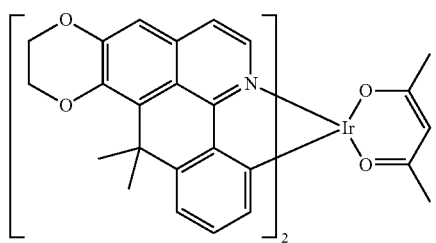
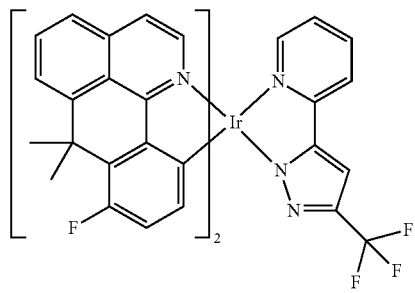
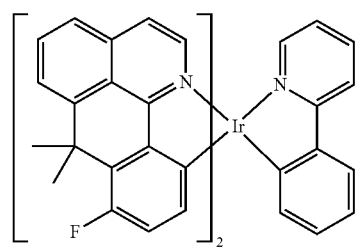
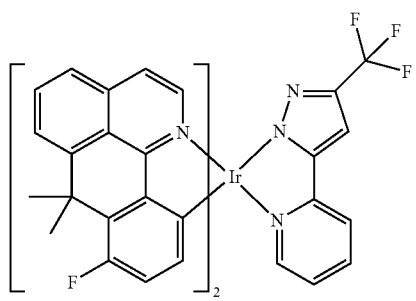
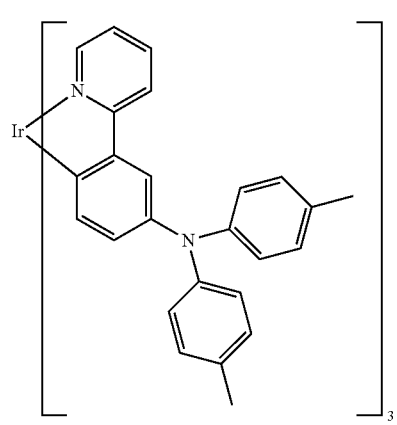
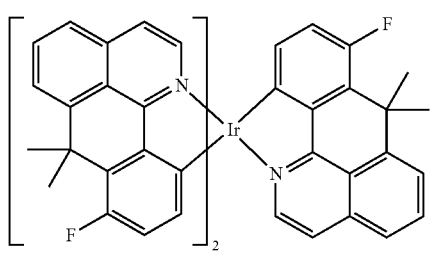
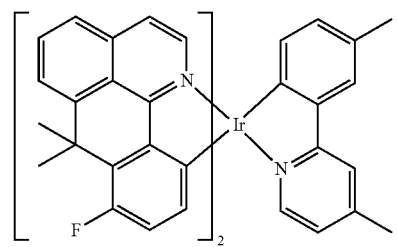
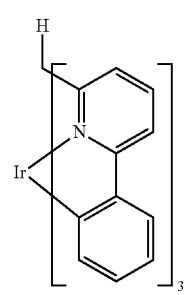

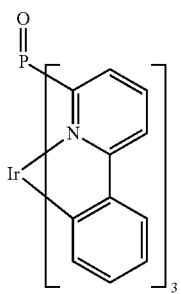
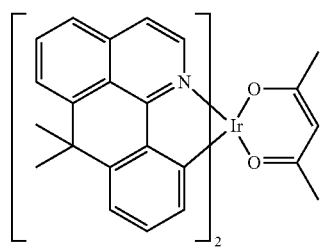
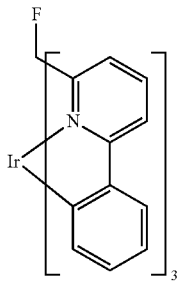
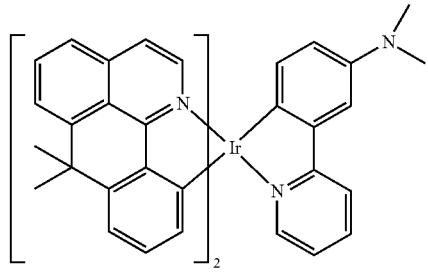
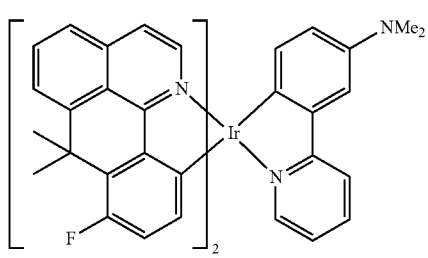
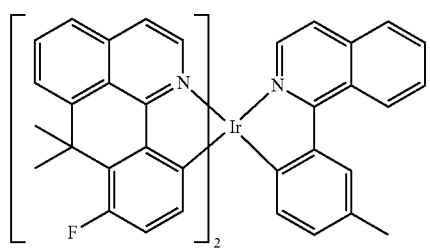
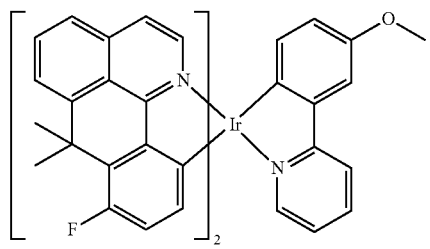
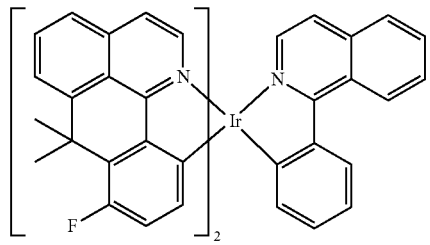
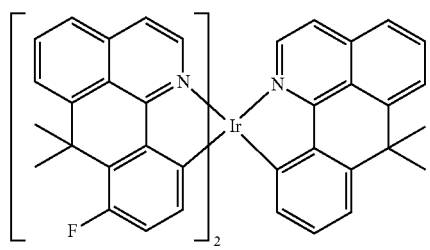
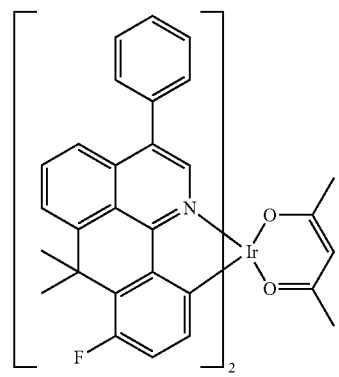

41
-continued
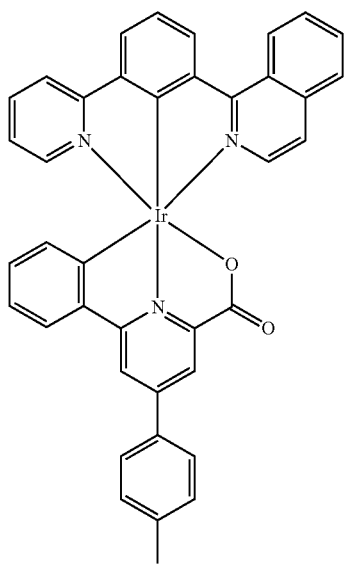
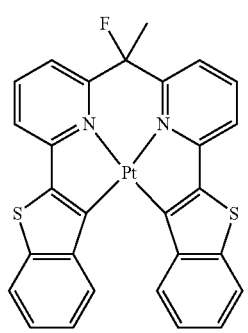
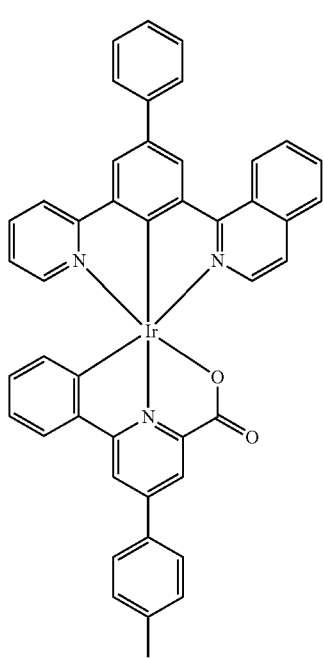
42
-continued
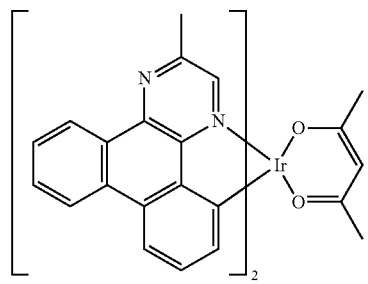
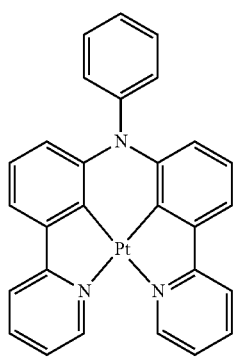
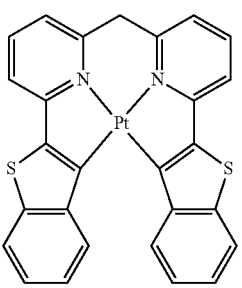
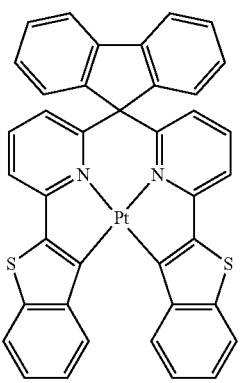
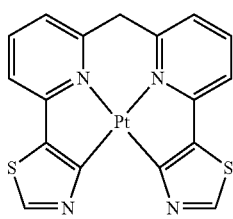

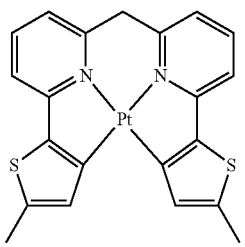
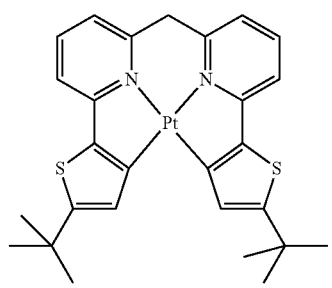
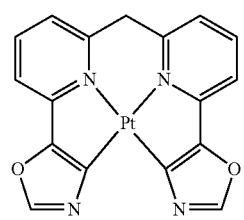
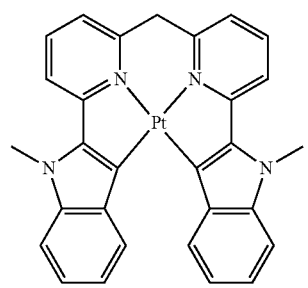
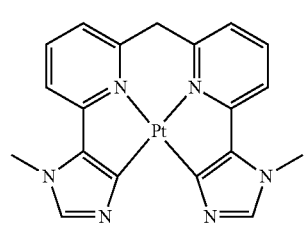
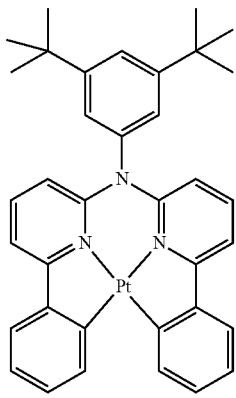
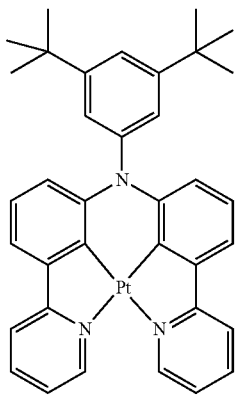
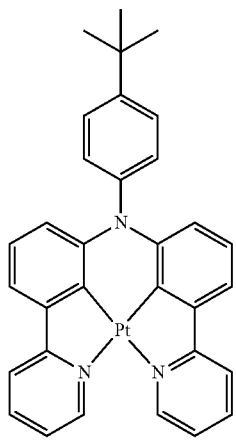
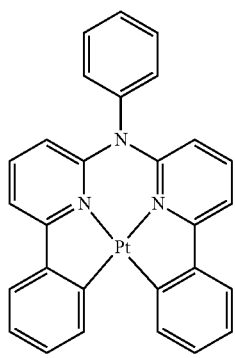

45
-continued
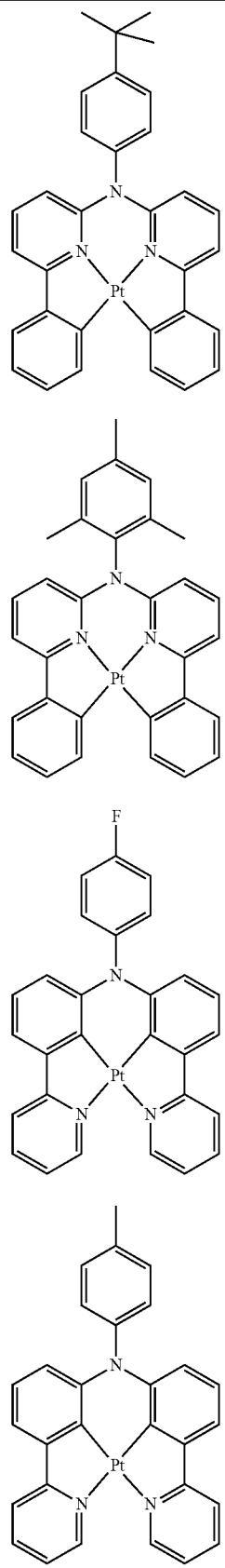
46
-continued
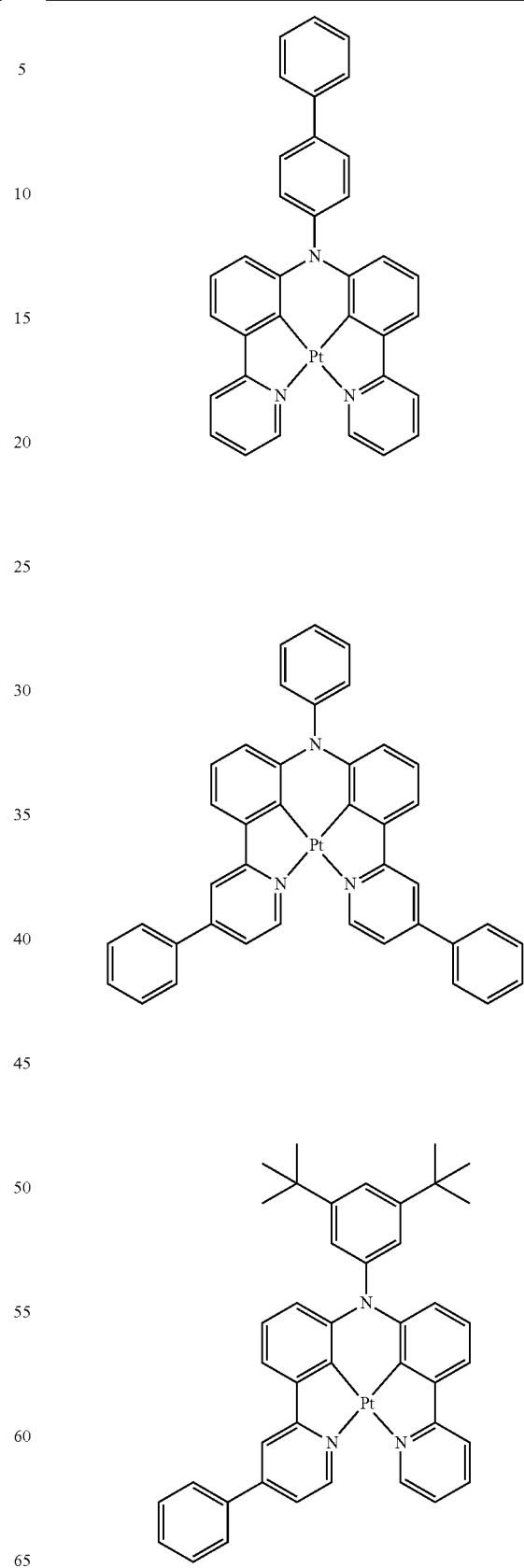

47
-continued
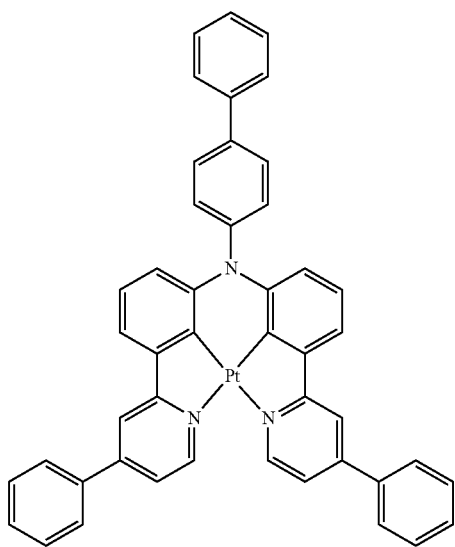
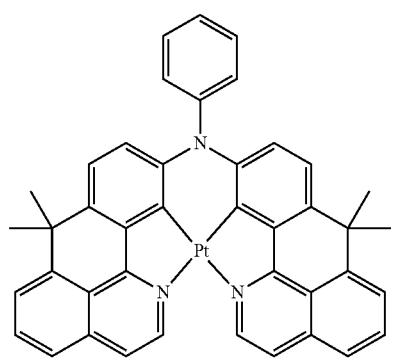
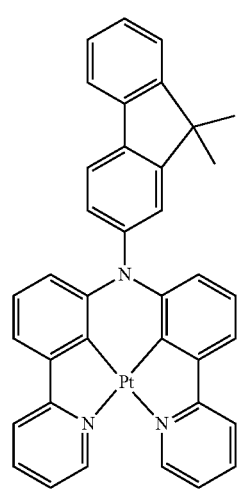
48
-continued
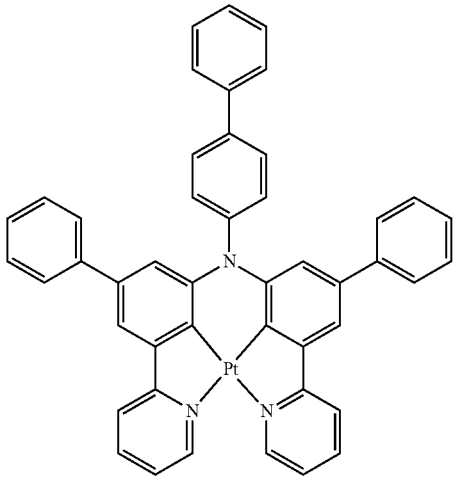
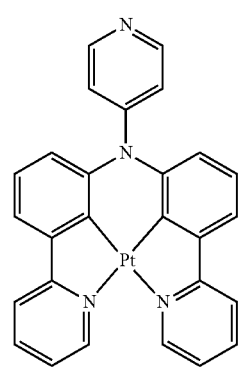
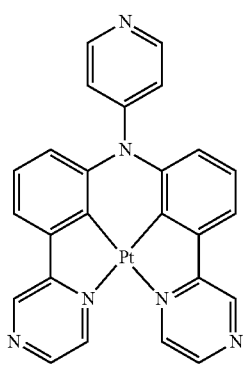
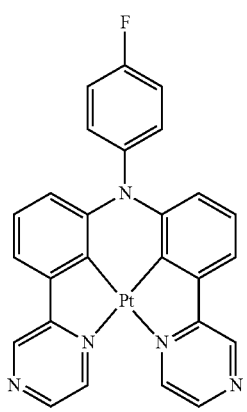

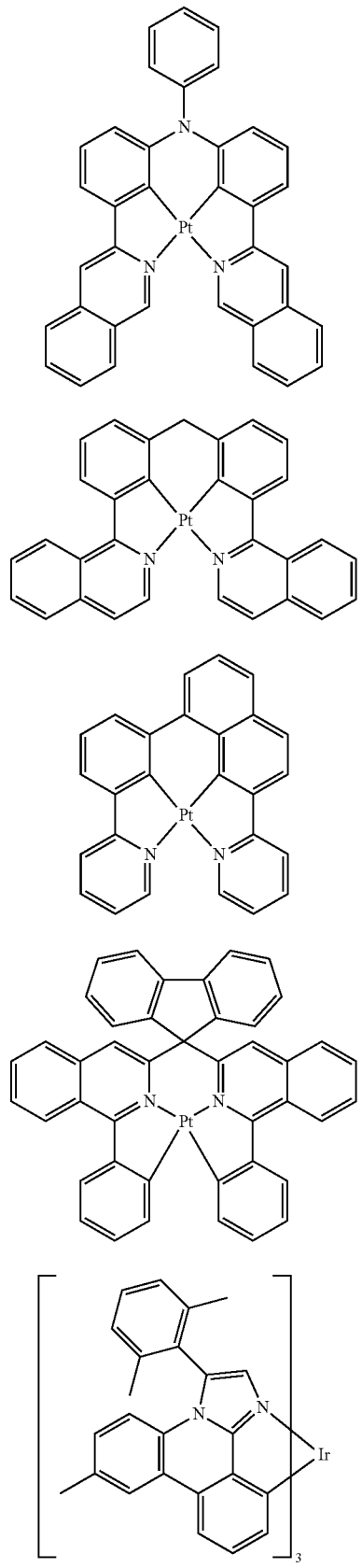
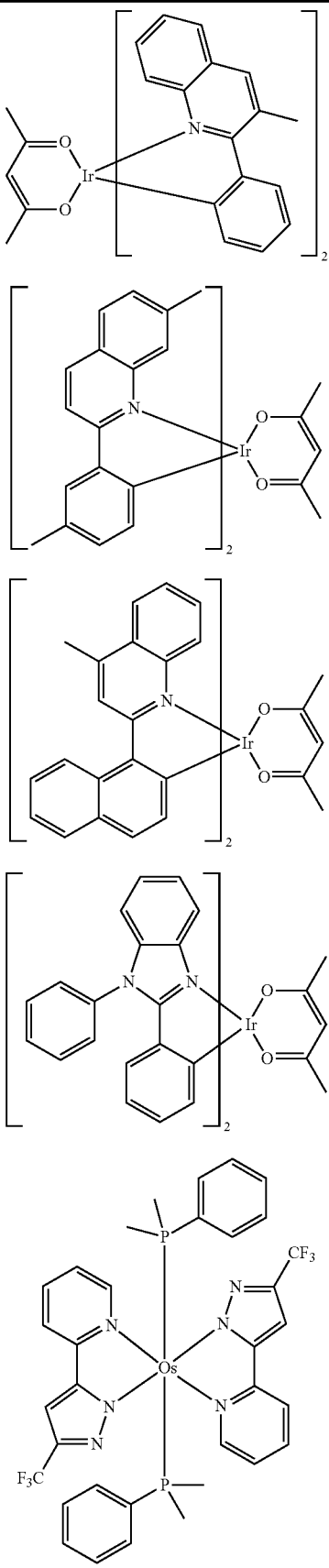

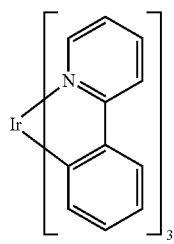
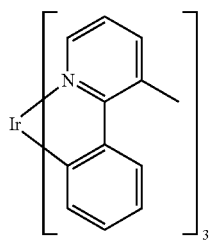
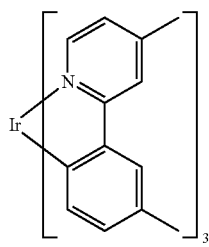
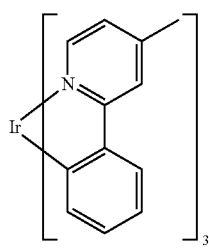
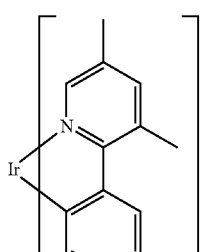
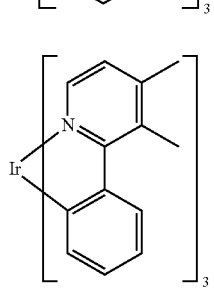
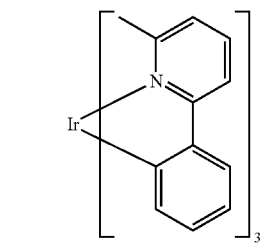
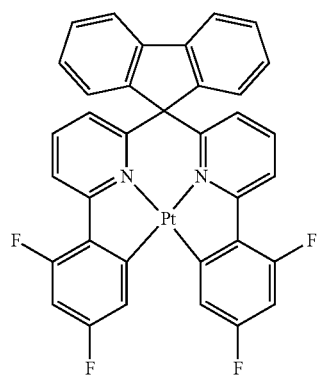
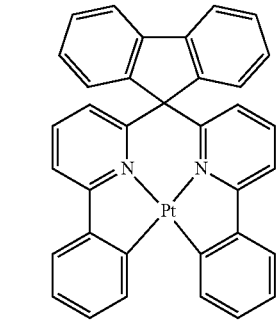
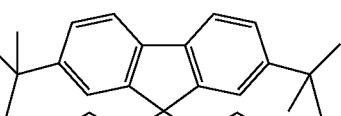
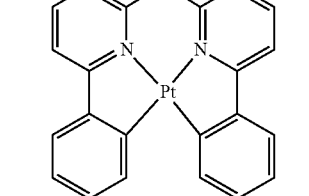

53
-continued
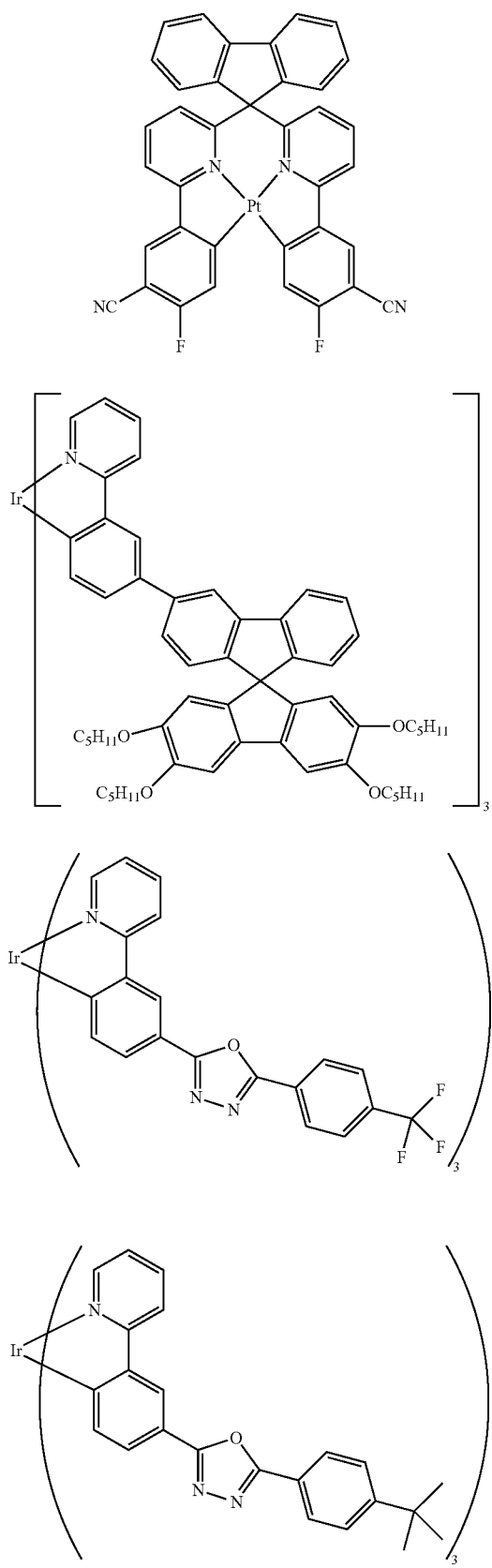
54
-continued
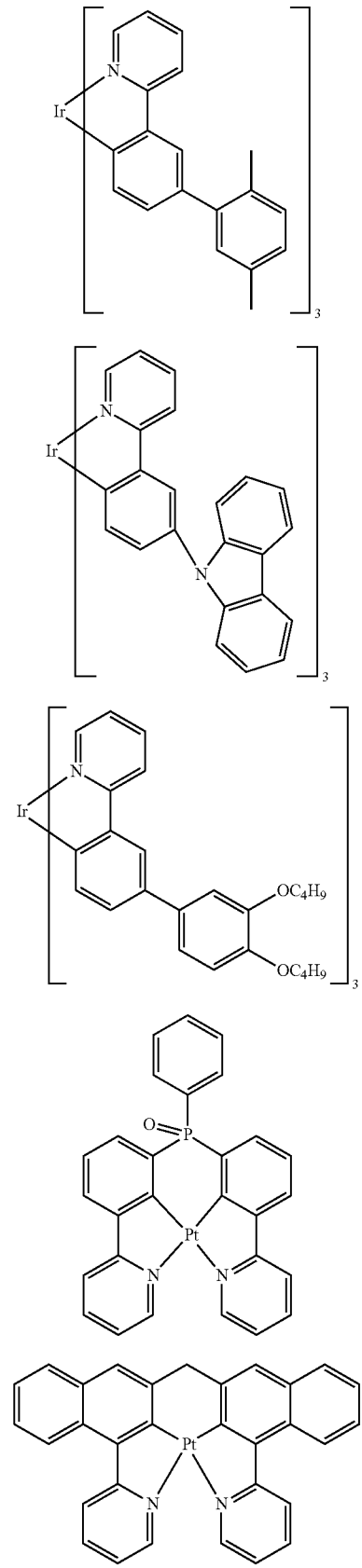

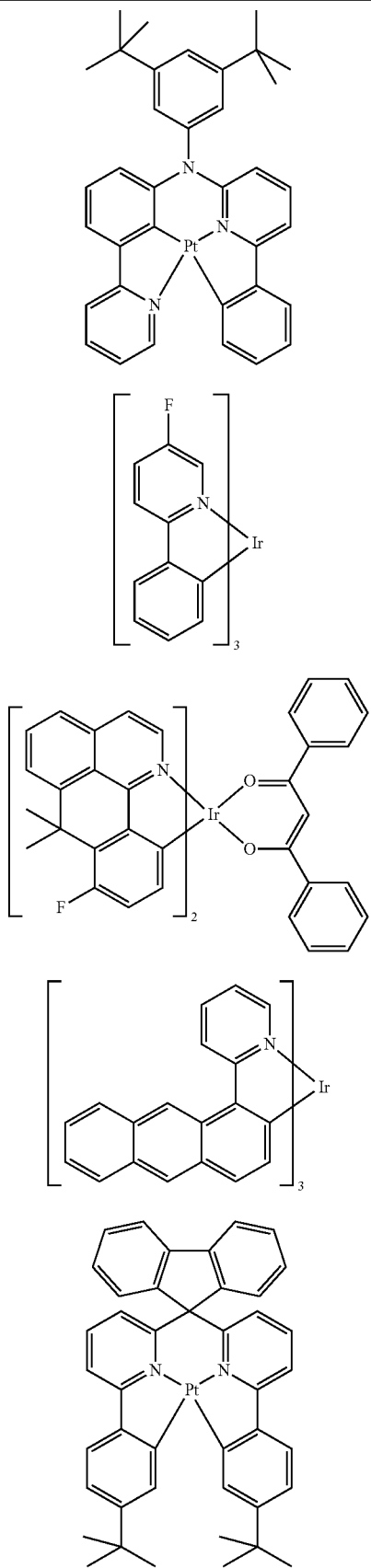
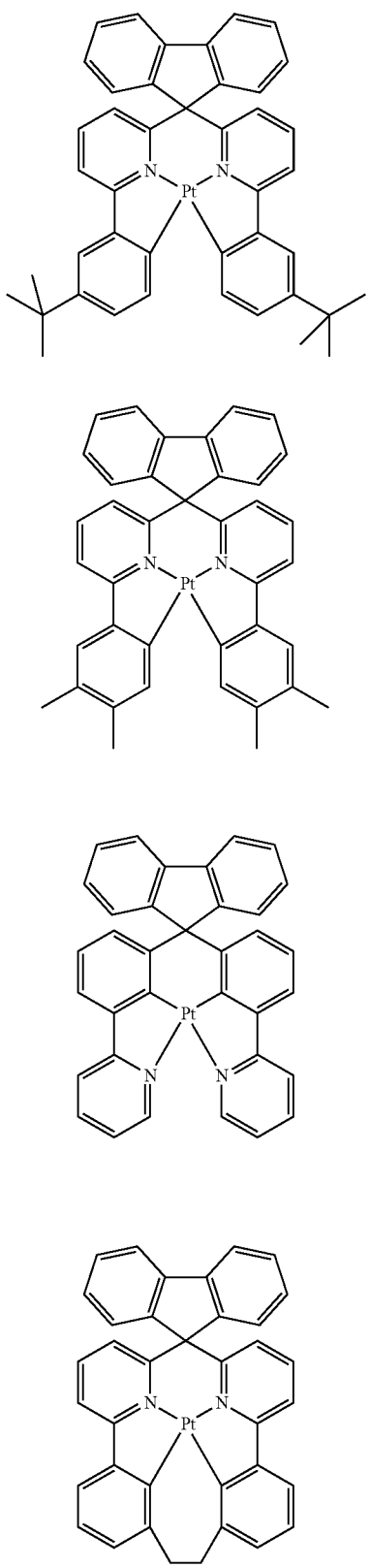

57
-continued
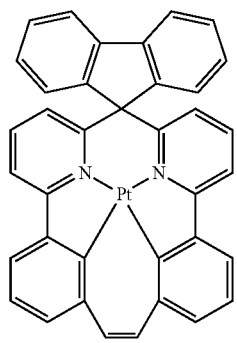
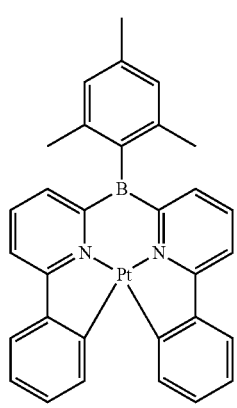
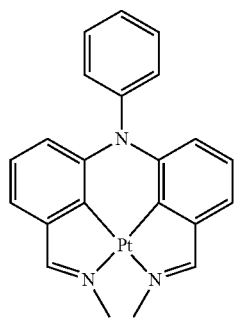
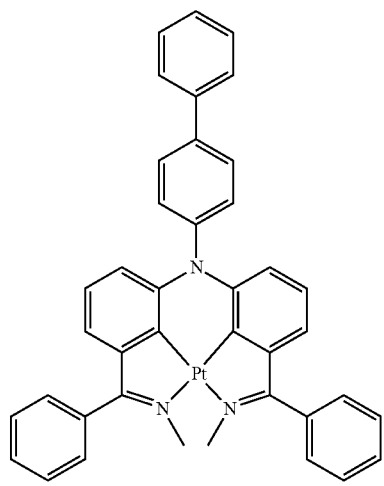
58
-continued
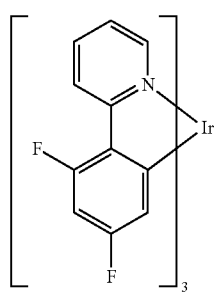
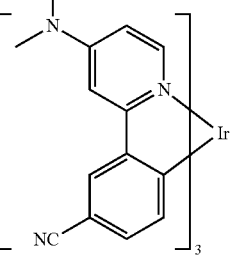
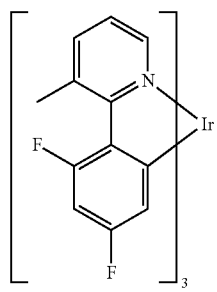
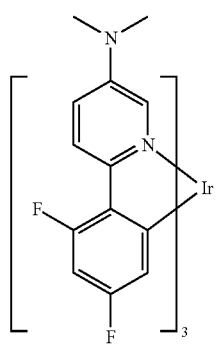

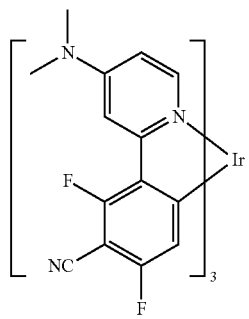
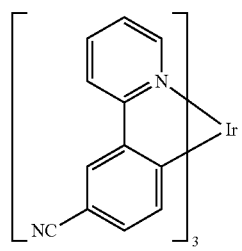
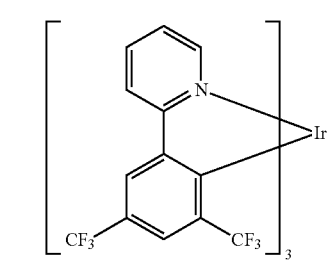
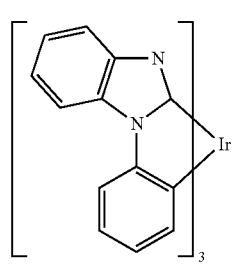
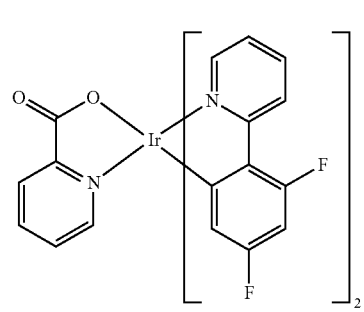
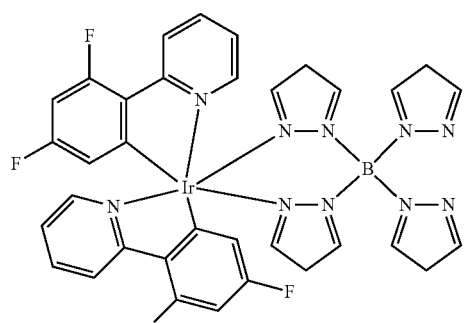

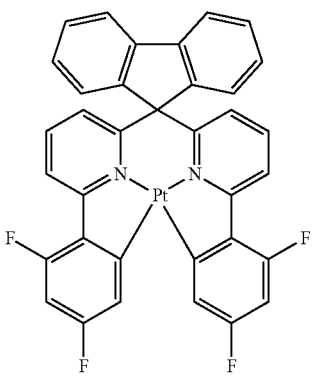

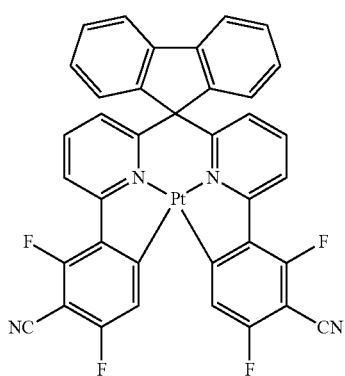

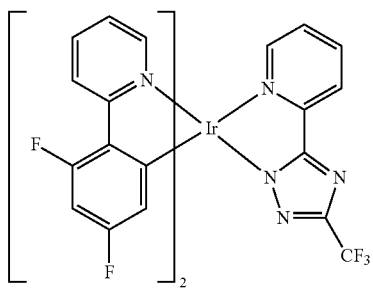

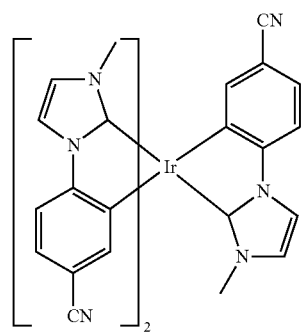

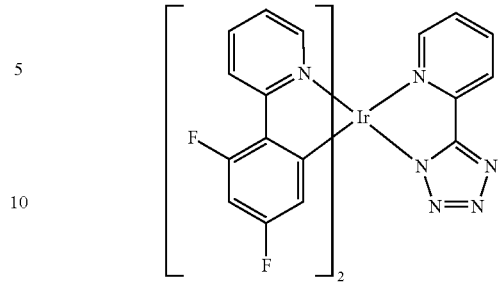

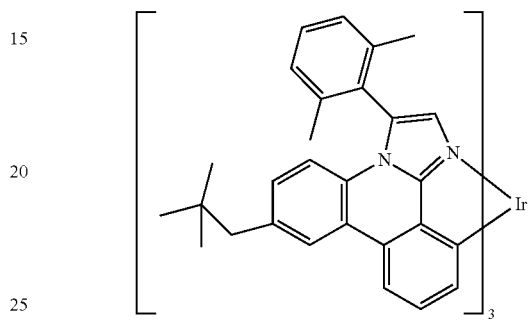

Preferred fluorescent dopants are selected from the class of the arylamines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorenediamines, for example in accordance with WO 06/122630, benzoindenofluorenamines or benzoindenofluorenediamines, for example in accordance with WO 08/006,449, and dibenzoindenofluorenamines or dibenzoindenofluorenediamines, for example in accordance with WO 07/140,847. Examples of fluorescent dopants from the class of the styrylamines are substituted or unsubstituted tristilbenamines or the fluorescent dopants described in WO 06/000388, WO 06/058737, WO 06/000389, WO 07/065,549 and WO 07/115,610. Preference is furthermore given to the condensed hydrocarbons disclosed in WO 2010/012328.

The compounds of the formula (I) are furthermore preferably used as fluorescent dopants.

Suitable fluorescent dopants are furthermore the structures depicted in the following table, and the derivatives of these structures disclosed in JP 06/001973, WO 04/047499, WO 06/098080, WO 07/065,678, US 2005/0260442 and WO 04/092111.

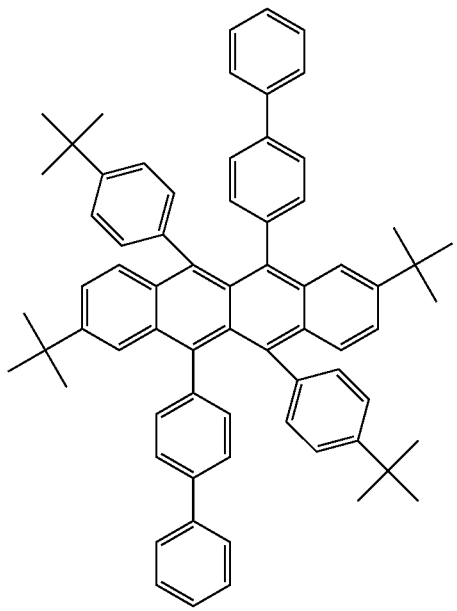 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]
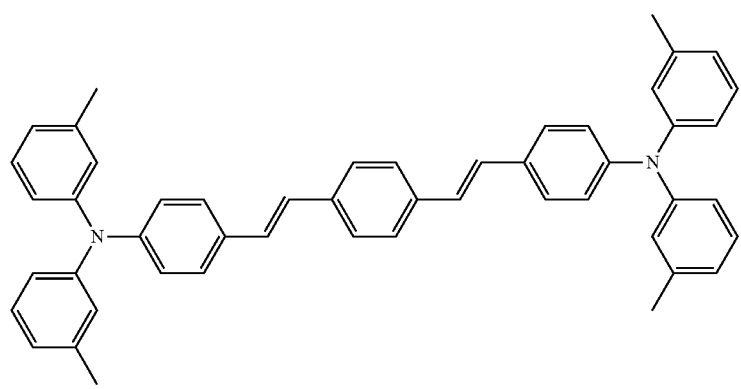 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]
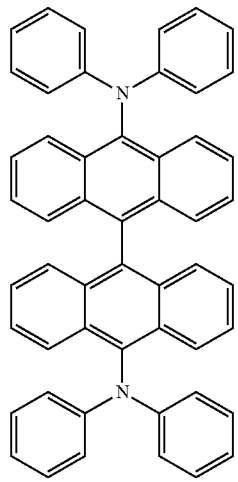 [SMILES: c1ccc(N(c2ccccc2)c2c3ccccc3c(-c3c4ccccc4c(N(c4ccccc4)c4ccccc4)c4ccccc34)c3ccccc23)cc1]

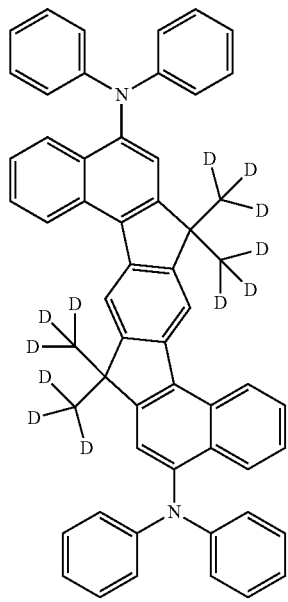 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]
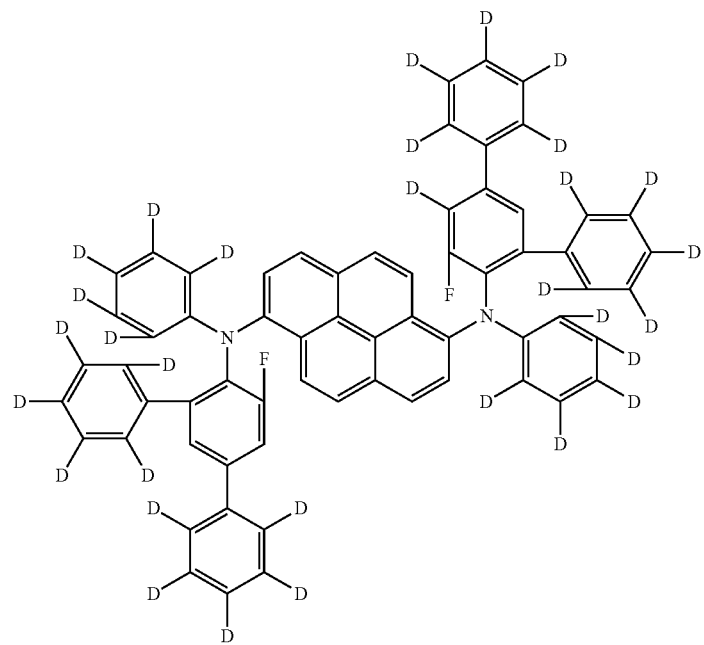 [SMILES: [2H]c1c([2H])c([2H])c(-c2cc(F)c(N(c3c([2H])c([2H])c([2H])c([2H])c3[2H])c3ccc4ccc5c(N(c6c([2H])c([2H])c([2H])c([2H])c6[2H])c6c(-c7c([2H])c([2H])c([2H])c([2H])c7[2H])cc(-c7c([2H])c([2H])c([2H])c([2H])c7[2H])c([2H])c6F)ccc6ccc3c4c65)c(-c3c([2H])c([2H])c([2H])c([2H])c3[2H])c2)c([2H])c1[2H]]
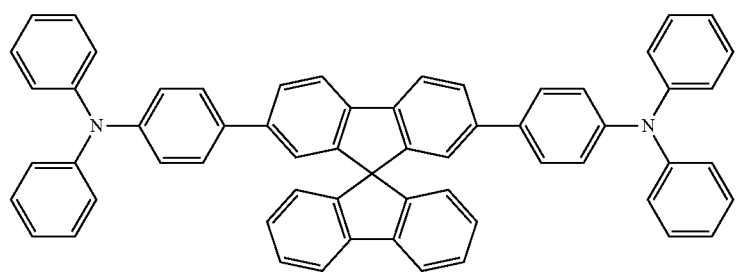 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]

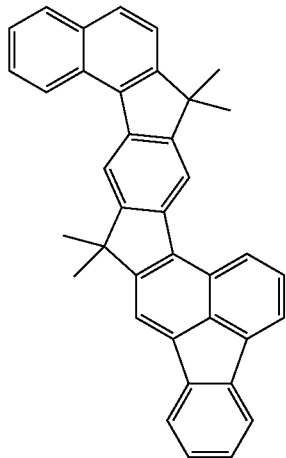 [SMILES: CC1(C)c2cc3c(cc2-c2c1ccc1ccccc21)C(C)(C)c1cc2c4c(cccc4c1-3)-c1ccccc1-2]
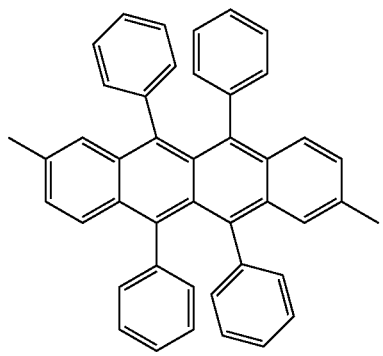
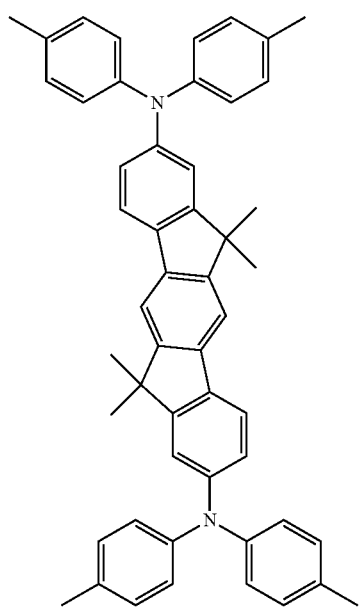

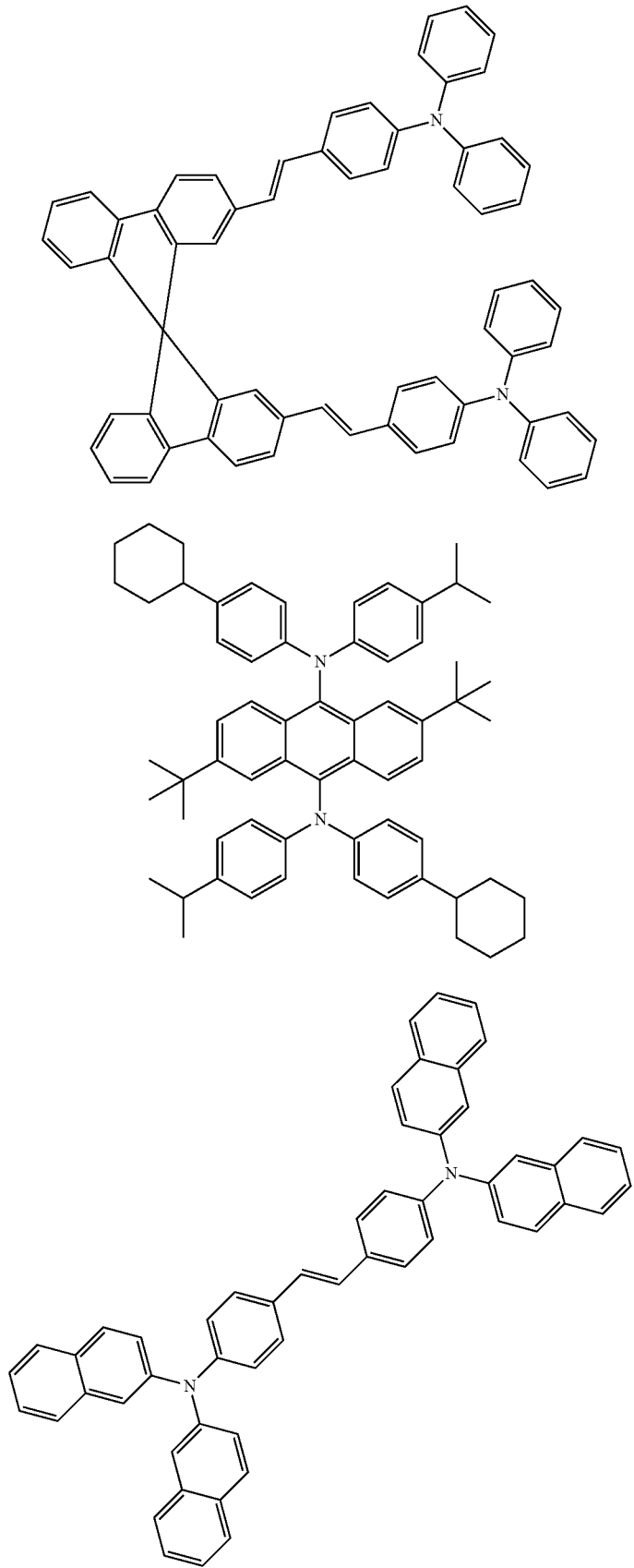

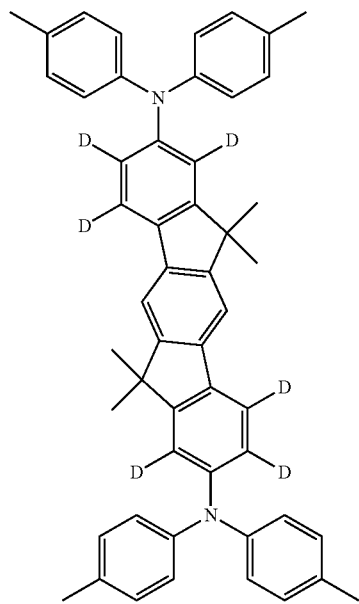
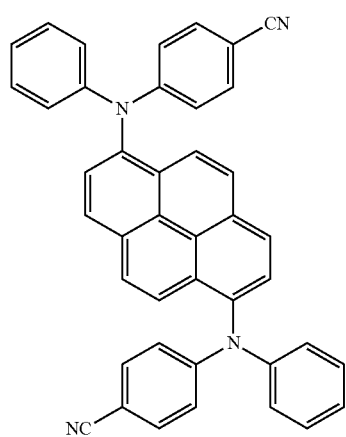 [SMILES: N#Cc1ccc(N(c2ccccc2)c2ccc3ccc4c(N(c5ccccc5)c5ccc(C#N)cc5)ccc5ccc2c3c54)cc1]

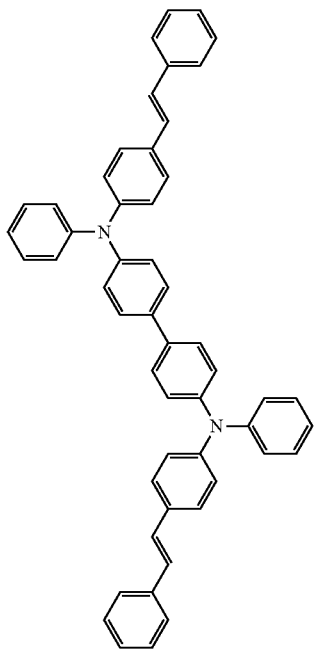 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
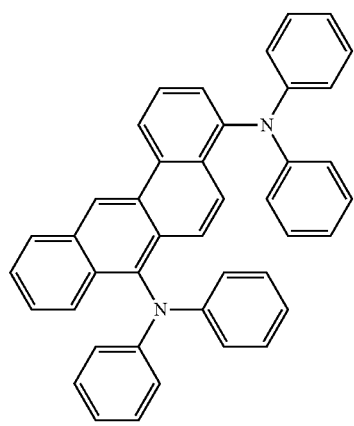 [SMILES: c1ccc(N(c2ccccc2)c2cccc3c2ccc2c(N(c4ccccc4)c4ccccc4)c4ccccc4cc23)cc1]
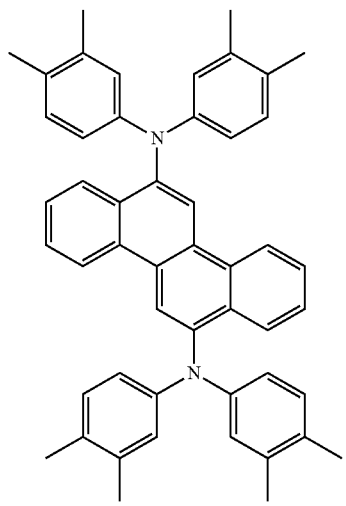

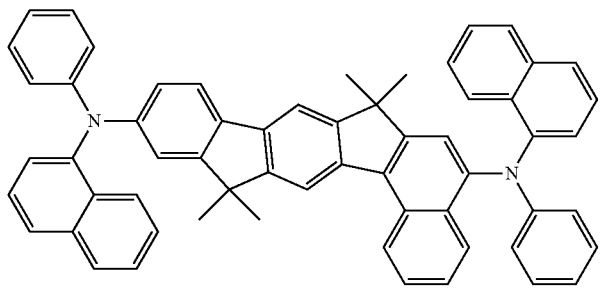 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
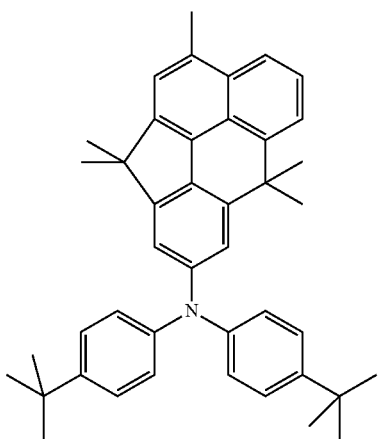 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]
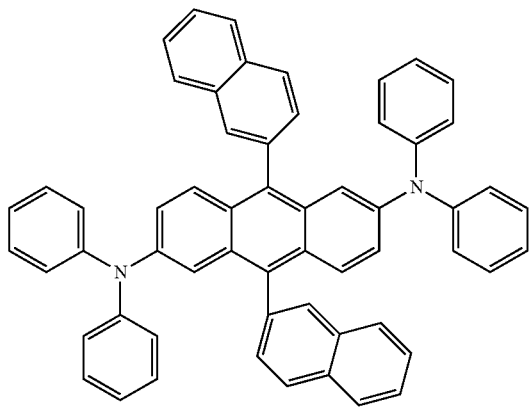 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
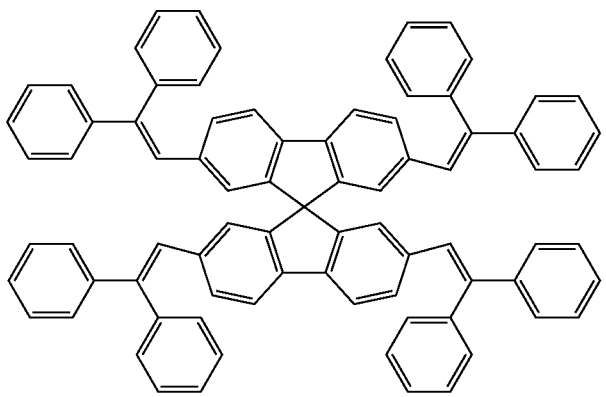 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]

-continued
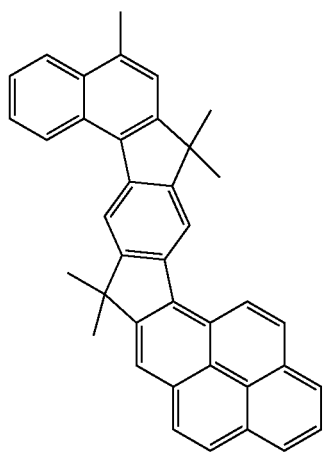 [SMILES: Cc1cc2c(c3ccccc13)-c1cc3c(cc1C2(C)C)-c1c(cc2ccc4cccc5ccc1c2c45)C3(C)C]
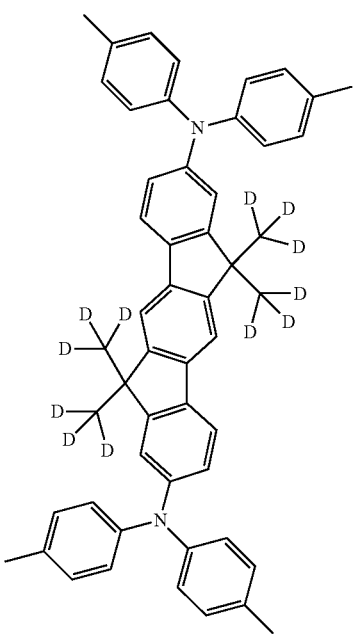
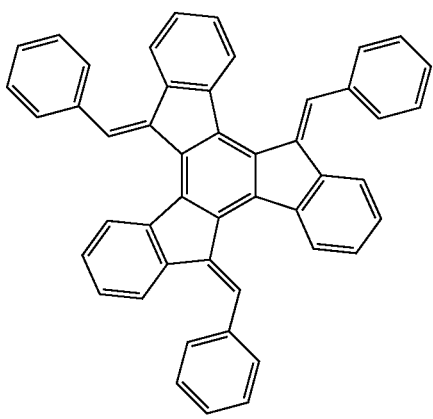 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]

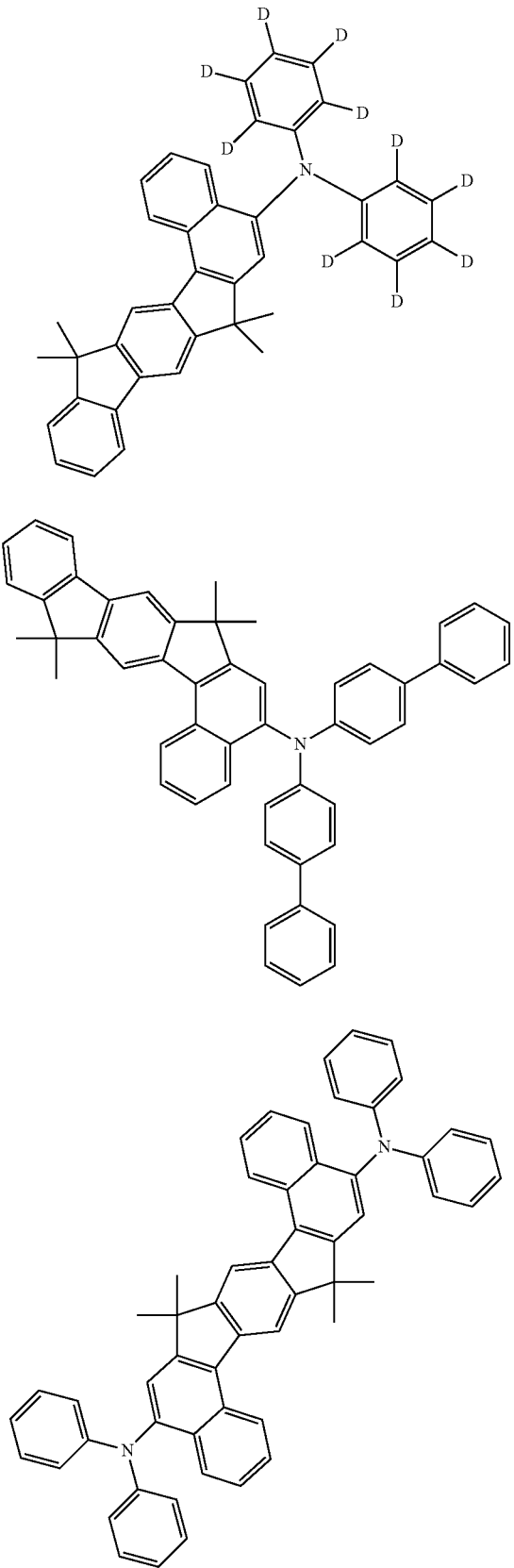

-continued
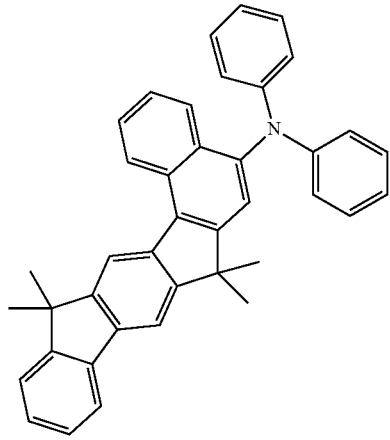 [SMILES: CC1(C)c2ccccc2-c2cc3c(cc21)-c1c(cc(N(c2ccccc2)c2ccccc2)c2ccccc12)C3(C)C]
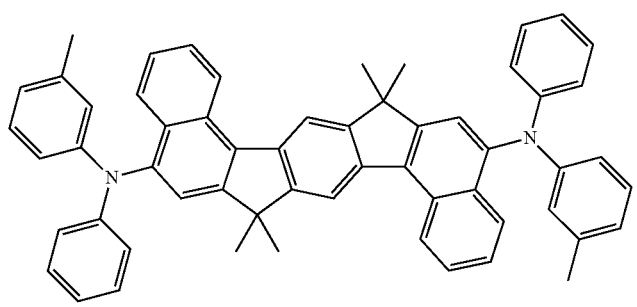 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
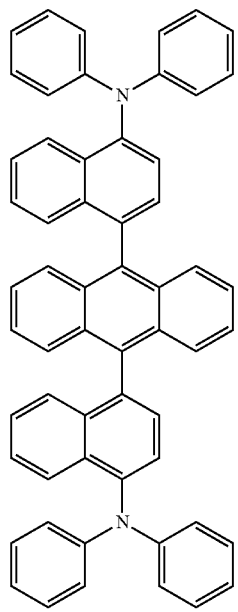 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]

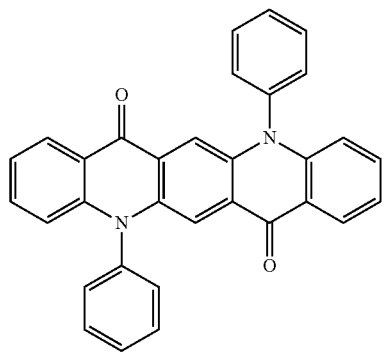 [SMILES: O=c1c2ccccc2n(-c2ccccc2)c2cc3c(=O)c4ccccc4n(-c4ccccc4)c3cc12]
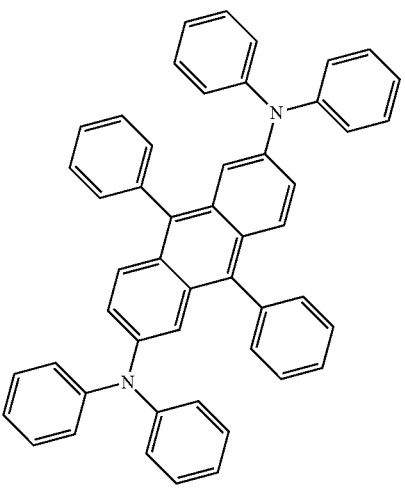 [SMILES: c1ccc(-c2c3ccc(N(c4ccccc4)c4ccccc4)cc3c(-c3ccccc3)c3ccc(N(c4ccccc4)c4ccccc4)cc23)cc1]
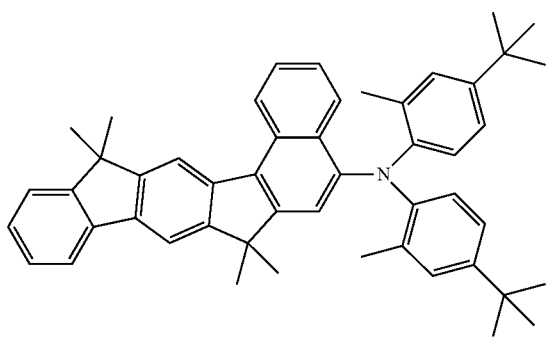 [SMILES: Cc1cc(C(C)(C)C)ccc1N(c1ccc(C(C)(C)C)cc1C)c1cc2c(c3ccccc13)-c1cc3c(cc1C2(C)C)-c1ccccc1C3(C)C]
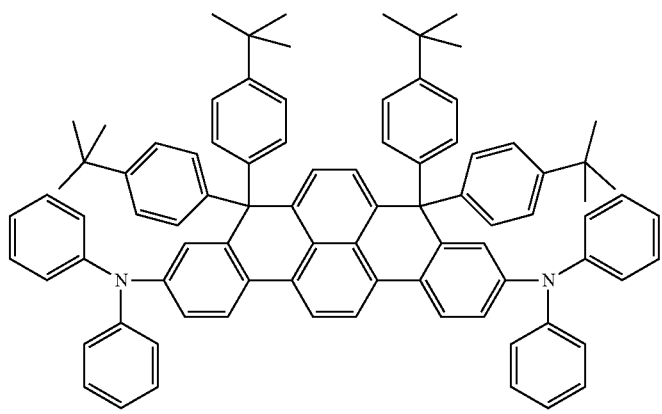 [SMILES: CC(C)(C)c1ccc(C2(c3ccc(C(C)(C)C)cc3)c3cc(N(c4ccccc4)c4ccccc4)ccc3-c3ccc4c5c(ccc2c35)C(c2ccc(C(C)(C)C)cc2)(c2ccc(C(C)(C)C)cc2)c2cc(N(c3ccccc3)c3ccccc3)ccc2-4)cc1]

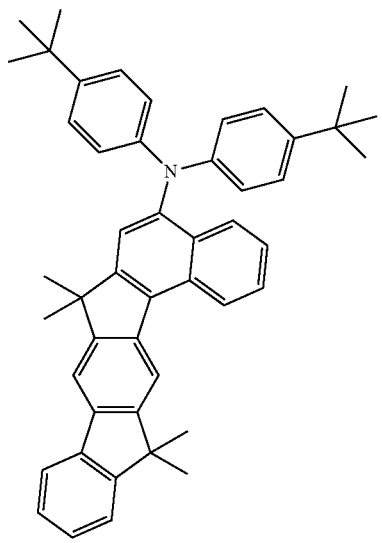 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
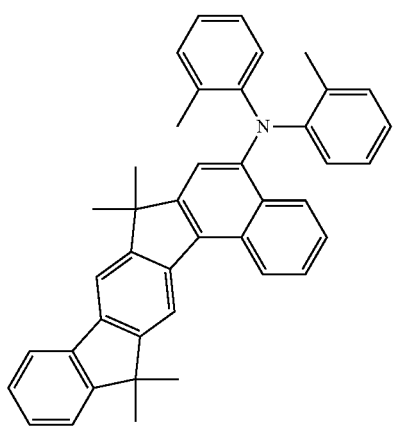 [SMILES: Cc1ccccc1N(c1ccccc1C)c1cc2c(c3ccccc13)-c1cc3c(cc1C2(C)C)-c1ccccc1C3(C)C]
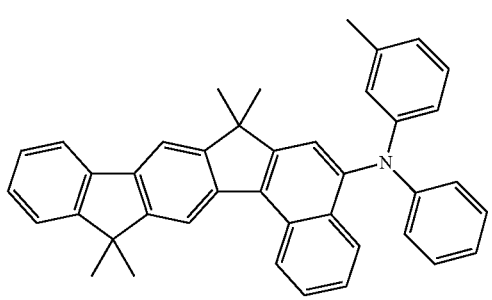 [SMILES: Cc1cccc(N(c2ccccc2)c2cc3c(c4ccccc24)-c2cc4c(cc2C3(C)C)-c2ccccc2C4(C)C)c1]
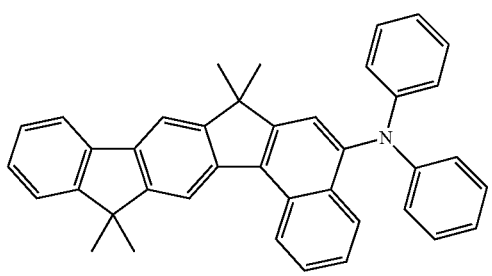 [SMILES: CC1(C)c2ccccc2-c2cc3c(cc21)-c1c(cc(N(c2ccccc2)c2ccccc2)c2ccccc12)C3(C)C]

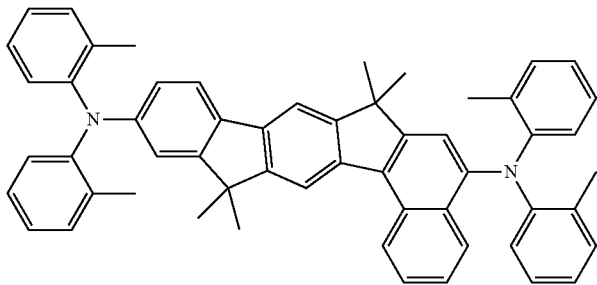 [SMILES: Cc1ccccc1N(c1ccc2c(c1)C(C)(C)c1cc3c(cc1-2)C(C)(C)c1cc(N(c2ccccc2C)c2ccccc2C)c2ccccc2c1-3)c1ccccc1C]
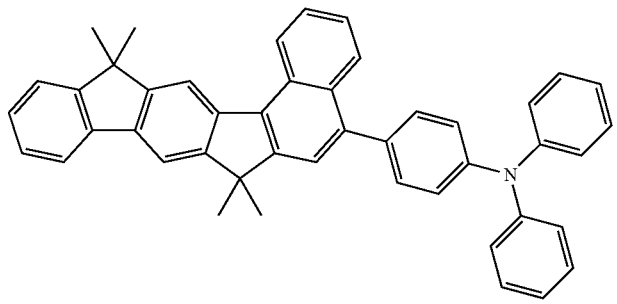 [SMILES: CC1(C)c2ccccc2-c2cc3c(cc21)-c1c(cc(-c2ccc(N(c4ccccc4)c4ccccc4)cc2)c2ccccc12)C3(C)C]
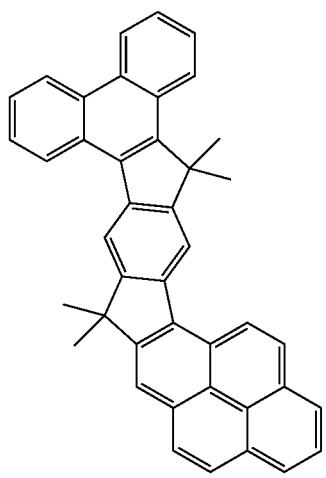 [SMILES: CC1(C)c2cc3c(cc2-c2c1cc1ccc4cccc5ccc2c1c45)C(C)(C)c1c-3c2ccccc2c2ccccc12]
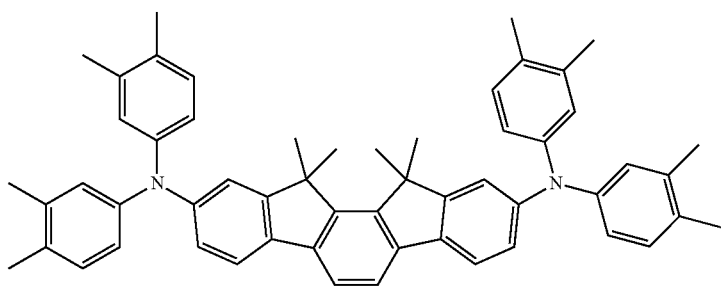
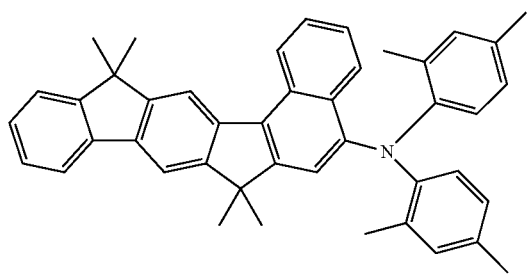 [SMILES: Cc1ccc(N(c2ccc(C)cc2C)c2cc3c(c4ccccc24)-c2cc4c(cc2C3(C)C)-c2ccccc2C4(C)C)c(C)c1]

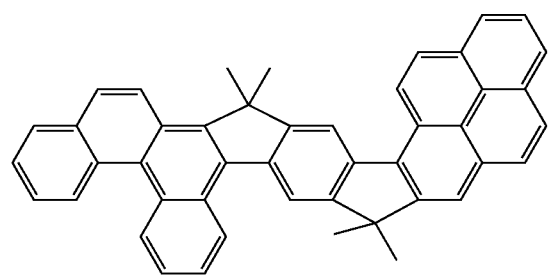 [SMILES: CC1(C)c2cc3c(cc2-c2c1cc1ccc4cccc5ccc2c1c45)C(C)(C)c1c-3c2ccccc2c2c1ccc1ccccc12]
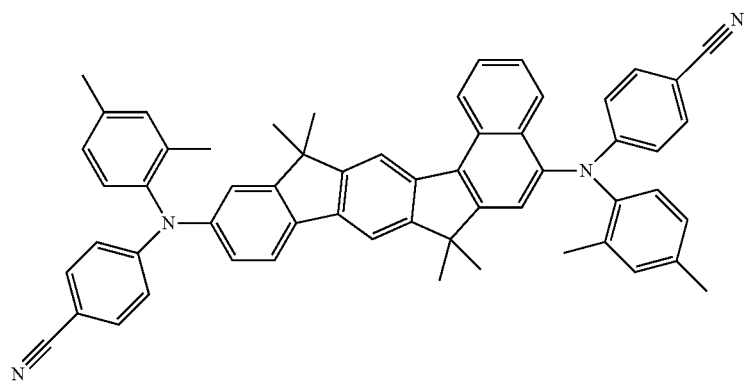 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
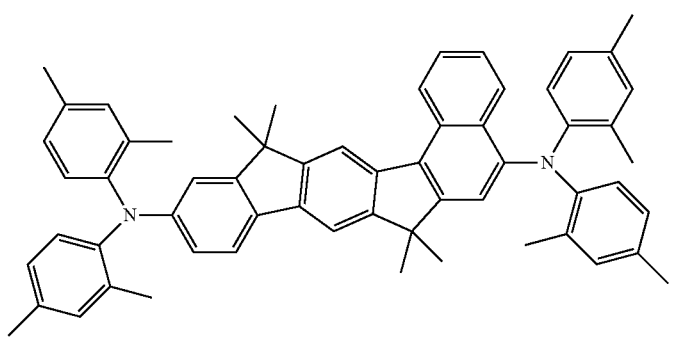
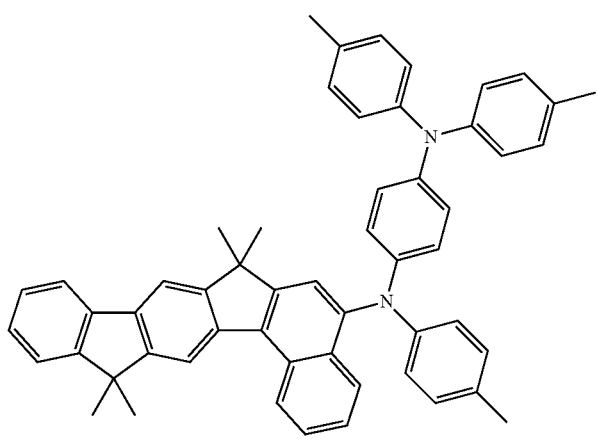 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

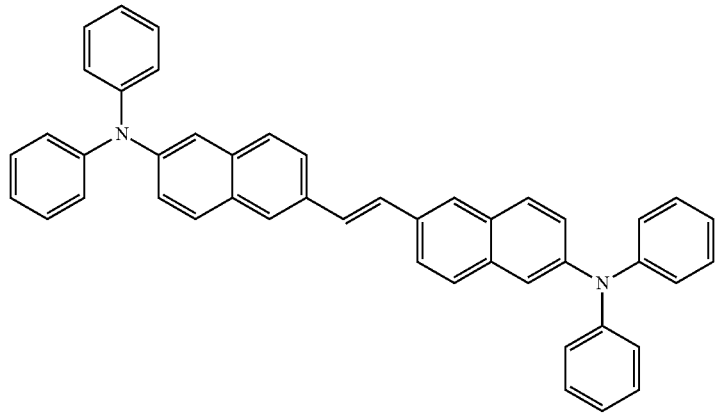 [SMILES: C(=C\c1ccc2cc(N(c3ccccc3)c3ccccc3)ccc2c1)/c1ccc2cc(N(c3ccccc3)c3ccccc3)ccc2c1]

Suitable matrix materials, preferably for fluorescent dopants, are materials from various classes of substance. Preferred matrix materials are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Suitable matrix materials are furthermore preferably the compounds according to the invention. Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. For the purposes of this invention, an oligoarylene is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006,449, U.S. Pat. No. 5,935,721, US 2005/0181232, JP 2000/273056, EP 681019, US 2004/0247937 and US 2005/0211958.

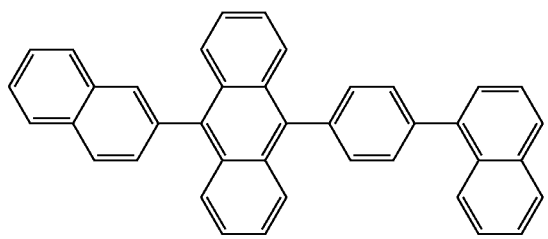 [SMILES: c1ccc2cc(-c3c4ccccc4c(-c4ccc(-c5cccc6ccccc56)cc4)c4ccccc34)ccc2c1]

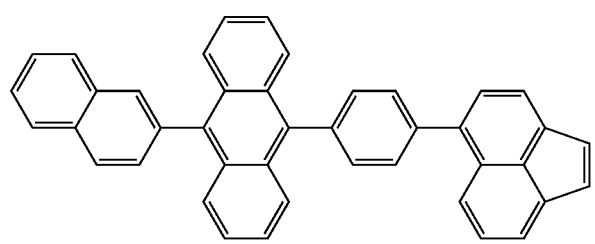 [SMILES: C1=Cc2ccc(-c3ccc(-c4c5ccccc5c(-c5ccc6ccccc6c5)c5ccccc45)cc3)c3cccc1c23]

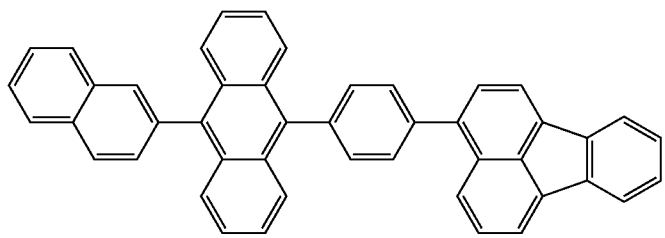 [SMILES: c1ccc2c(c1)-c1cccc3c(-c4ccc(-c5c6ccccc6c(-c6ccc7ccccc7c6)c6ccccc56)cc4)ccc-2c13]
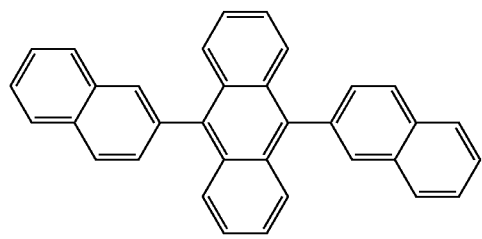 [SMILES: c1ccc2cc(-c3c4ccccc4c(-c4ccc5ccccc5c4)c4ccccc34)ccc2c1]
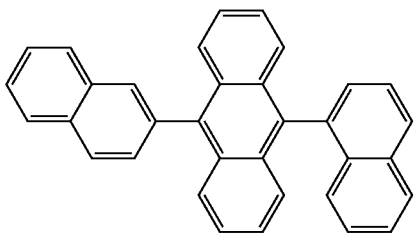 [SMILES: c1ccc2cc(-c3c4ccccc4c(-c4cccc5ccccc45)c4ccccc34)ccc2c1]
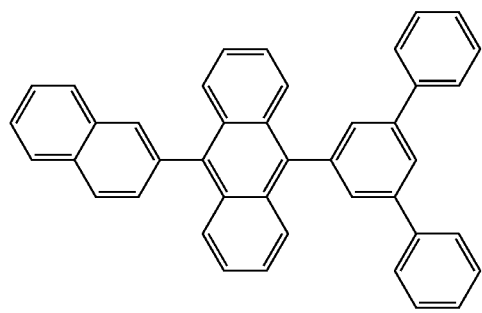 [SMILES: c1ccc(-c2cc(-c3ccccc3)cc(-c3c4ccccc4c(-c4ccc5ccccc5c4)c4ccccc34)c2)cc1]
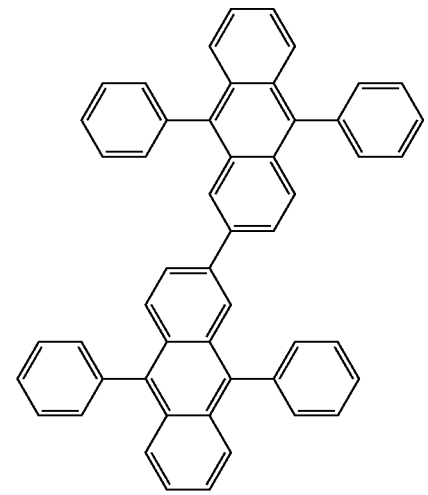 [SMILES: c1ccc(-c2c3ccccc3c(-c3ccccc3)c3cc(-c4ccc5c(-c6ccccc6)c6ccccc6c(-c6ccccc6)c5c4)ccc23)cc1]

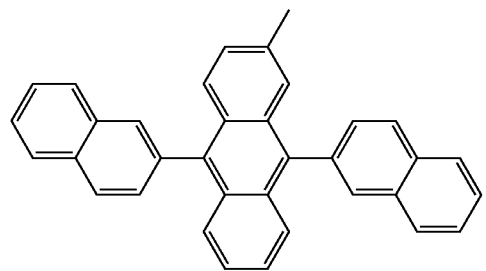 [SMILES: Cc1ccc2c(-c3ccc4ccccc4c3)c3ccccc3c(-c3ccc4ccccc4c3)c2c1]
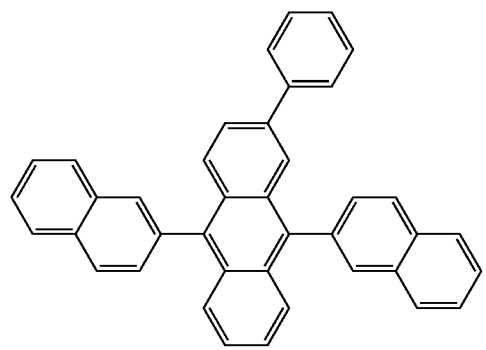 [SMILES: c1ccc(-c2ccc3c(-c4ccc5ccccc5c4)c4ccccc4c(-c4ccc5ccccc5c4)c3c2)cc1]
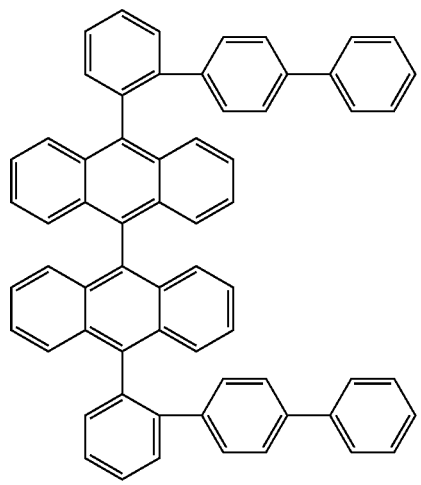 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
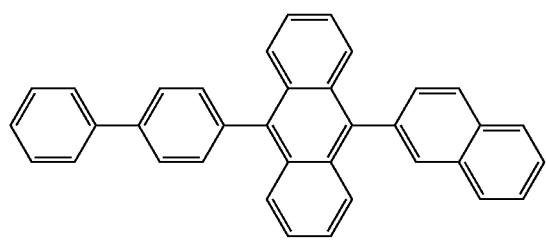 [SMILES: c1ccc(-c2ccc(-c3c4ccccc4c(-c4ccc5ccccc5c4)c4ccccc34)cc2)cc1]

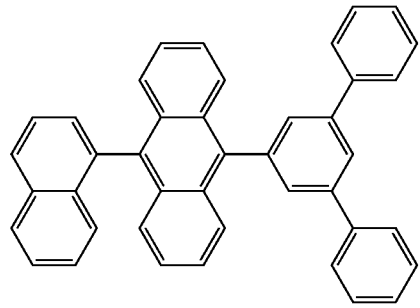 [SMILES: c1ccc(-c2cc(-c3ccccc3)cc(-c3c4ccccc4c(-c4cccc5ccccc45)c4ccccc34)c2)cc1]

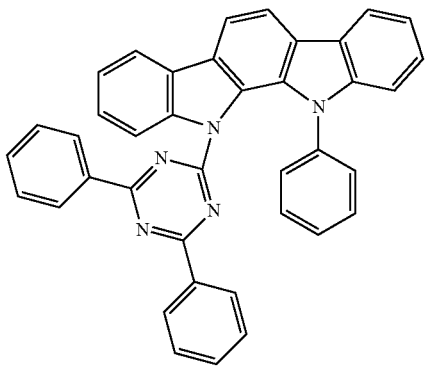 [SMILES: c1ccc(-c2nc(-c3ccccc3)nc(-n3c4ccccc4c4ccc5c6ccccc6n(-c6ccccc6)c5c43)n2)cc1]
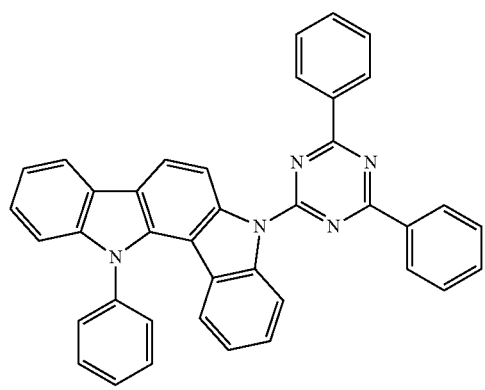 [SMILES: c1ccc(-c2nc(-c3ccccc3)nc(-n3c4ccccc4c4c3ccc3c5ccccc5n(-c5ccccc5)c34)n2)cc1]
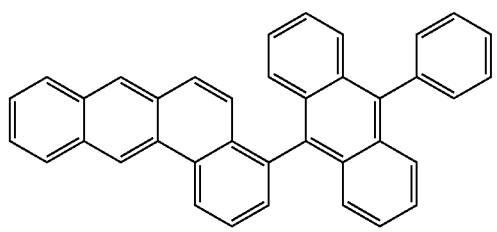 [SMILES: c1ccc(-c2c3ccccc3c(-c3cccc4c3ccc3cc5ccccc5cc34)c3ccccc23)cc1]
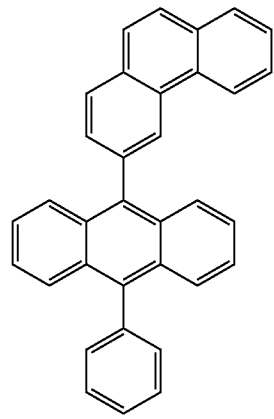 [SMILES: c1ccc(-c2c3ccccc3c(-c3ccc4ccc5ccccc5c4c3)c3ccccc23)cc1]

-continued
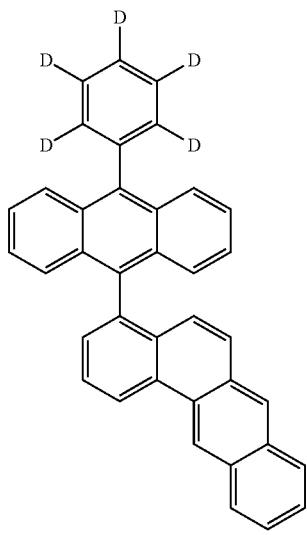 [SMILES: [2H]c1c([2H])c([2H])c(-c2c3ccccc3c(-c3cccc4c3ccc3cc5ccccc5cc34)c3ccccc23)c([2H])c1[2H]]
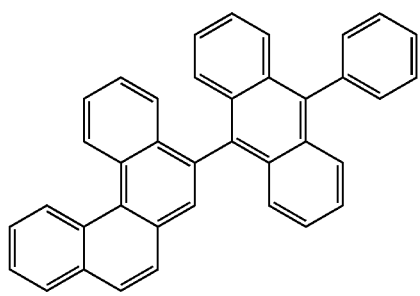 [SMILES: c1ccc(-c2c3ccccc3c(-c3cc4ccc5ccccc5c4c4ccccc34)c3ccccc23)cc1]
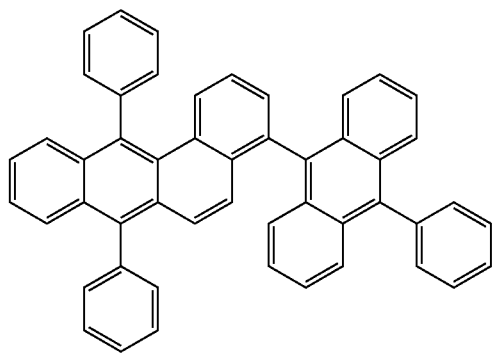 [SMILES: c1ccc(-c2c3ccccc3c(-c3cccc4c3ccc3c(-c5ccccc5)c5ccccc5c(-c5ccccc5)c34)c3ccccc23)cc1]
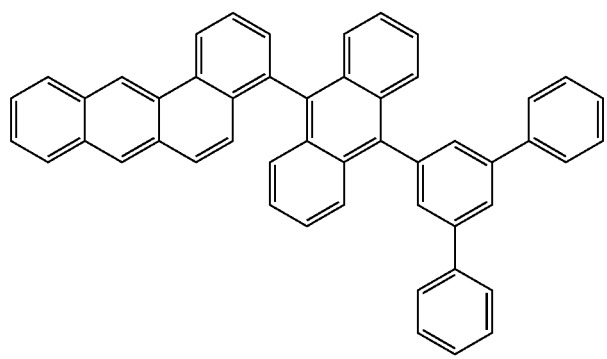 [SMILES: c1ccc(-c2cc(-c3ccccc3)cc(-c3c4ccccc4c(-c4cccc5c4ccc4cc6ccccc6cc45)c4ccccc34)c2)cc1]

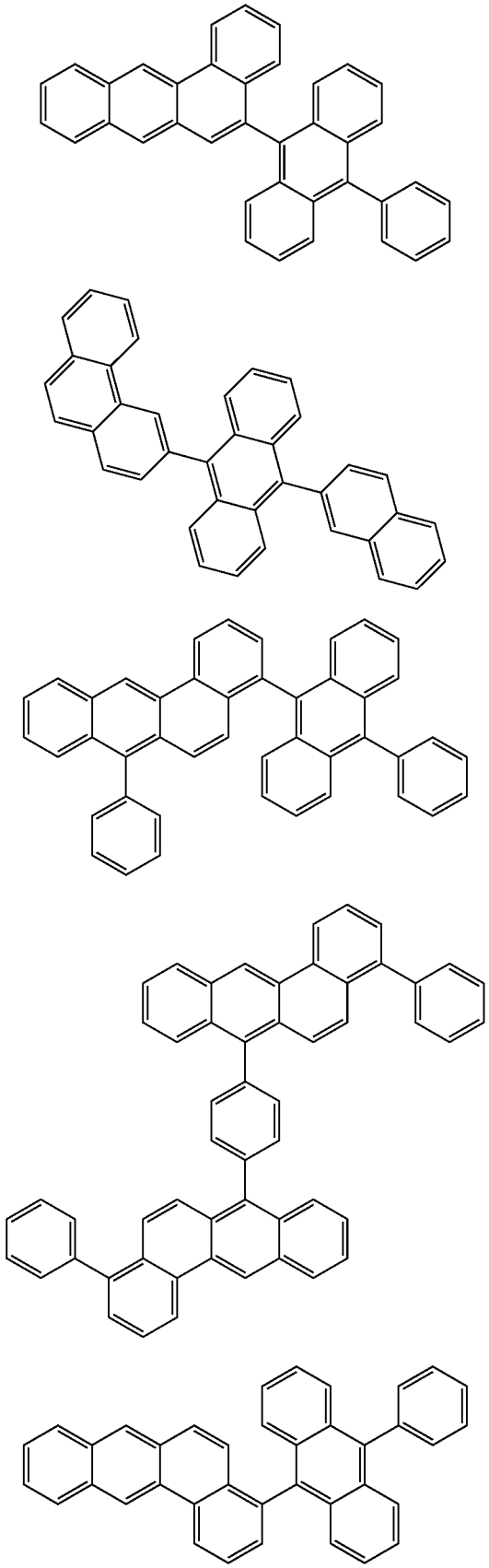

-continued
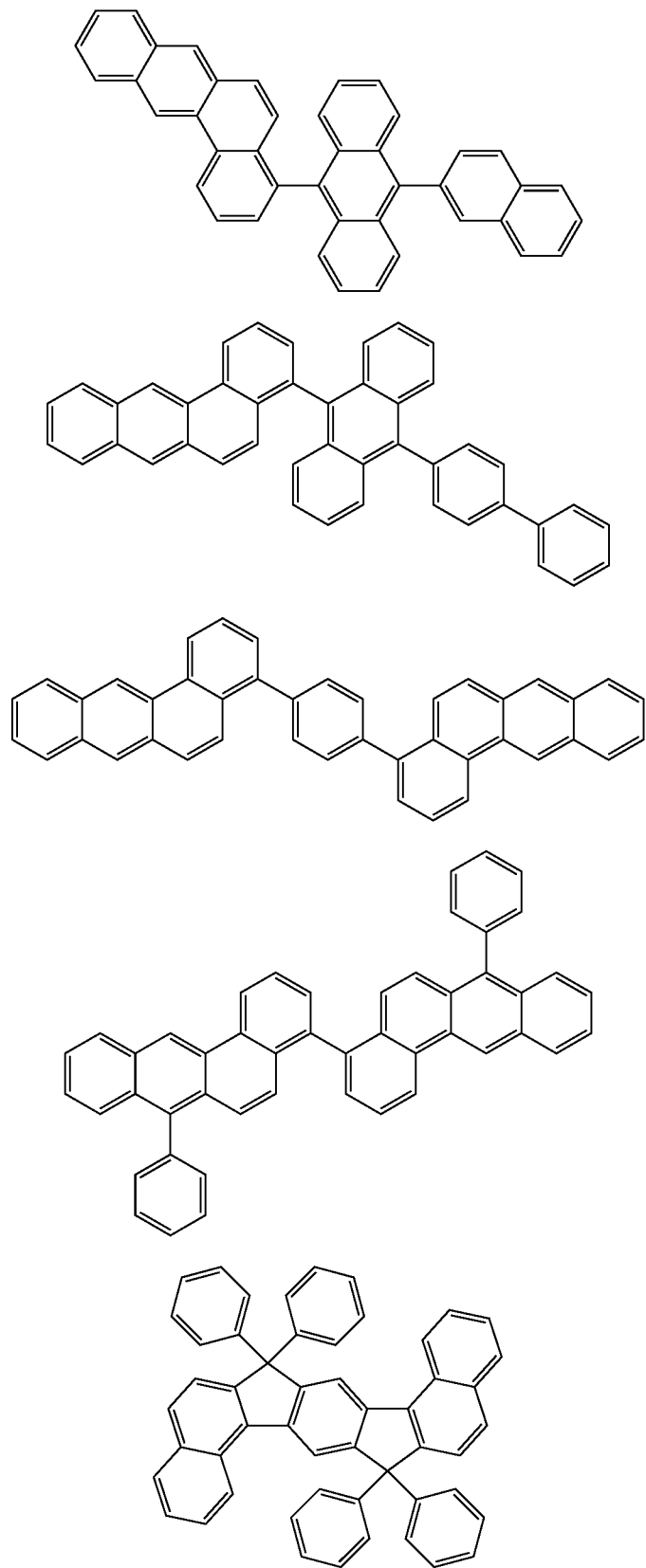

-continued
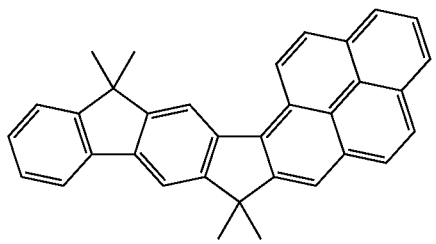 [SMILES: CC1(C)c2ccccc2-c2cc3c(cc21)-c1c(cc2ccc4cccc5ccc1c2c45)C3(C)C]
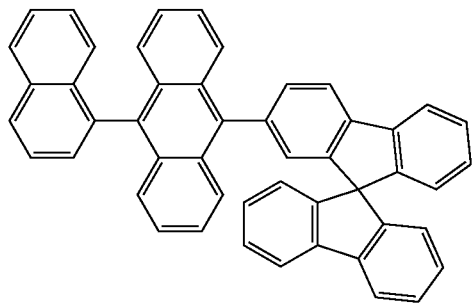 [SMILES: c1ccc2c(c1)-c1ccccc1C21c2ccccc2-c2ccc(-c3c4ccccc4c(-c4cccc5ccccc45)c4ccccc34)cc21]
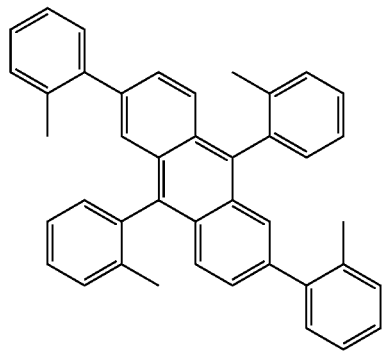 [SMILES: Cc1ccccc1-c1ccc2c(-c3ccccc3C)c3cc(-c4ccccc4C)ccc3c(-c3ccccc3C)c2c1]
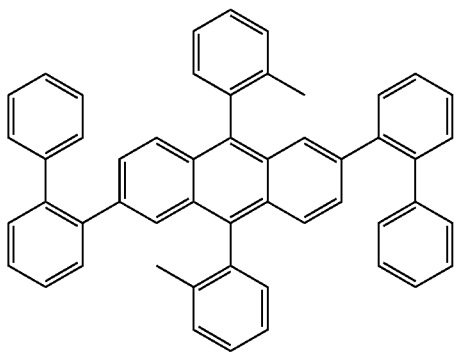 [SMILES: Cc1ccccc1-c1c2ccc(-c3ccccc3-c3ccccc3)cc2c(-c2ccccc2C)c2ccc(-c3ccccc3-c3ccccc3)cc12]
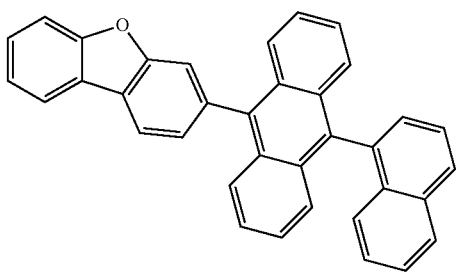 [SMILES: c1ccc2c(-c3c4ccccc4c(-c4ccc5c(c4)oc4ccccc45)c4ccccc34)cccc2c1]

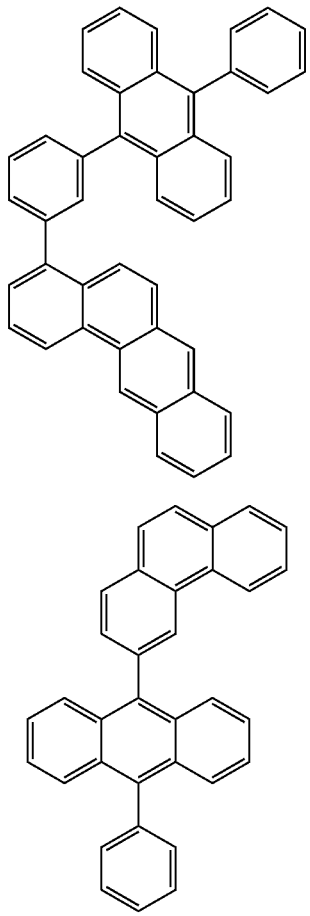

Besides the compounds of the formula (I), suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are then generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cell) or the coupling-out of light (OLED, O-laser). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar.

However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carriergas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

It is furthermore preferred to produce an organic electroluminescent device according to the invention by applying one or more layers from solution and one or more layers by a sublimation process.

The organic electroluminescent devices comprising one or more compounds of the formula (I) can be employed in accordance with the invention in displays, as light sources in lighting applications and as light sources in medical and/or cosmetic applications (for example light therapy).

On use of the compounds of the formula (I) in organic electroluminescent devices, one or more of the advantages indicated below can be achieved:

The compounds of the formula (I) are very highly suitable for use as hole-transport materials and for use as matrix materials for phosphorescent dopants. On use of the compounds according to the invention in these functions, good power efficiencies, low operating voltages and good lifetimes of the organic electroluminescent devices are obtained.

It has been found that the compounds according to formula (I) show a high thermal stability. The formation of decomposition products is reduced compared with similar compounds known in the state of the art.

It has been found that an improvement in the performance data of the organic electroluminescent device compared with the arylamine compounds known from the prior art which contain a carbazole unit and a fluorene unit can be achieved with the compounds according to the invention.

The invention is explained in greater detail by the following working examples without a restriction in the subject-matter of the invention being derived therefrom.

USE EXAMPLES

The following syntheses were carried out under a protective-gas atmosphere, unless indicated otherwise. The starting materials were purchased from ALDRICH or ABCR.

A) Synthesis Example 1

Synthesis of biphenyl-4-yl-(9,9-dimethyl-9H-fluoren-2-yl)-[2-methyl-4-(9-phenyl-9H-carbazol-3-yl)phenyl]amine

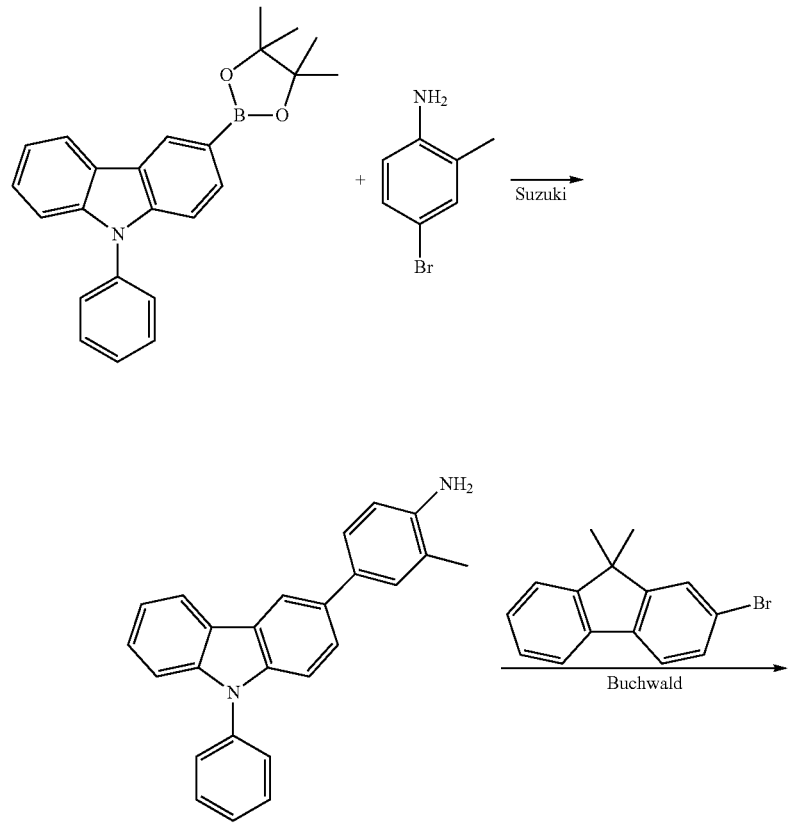

-continued

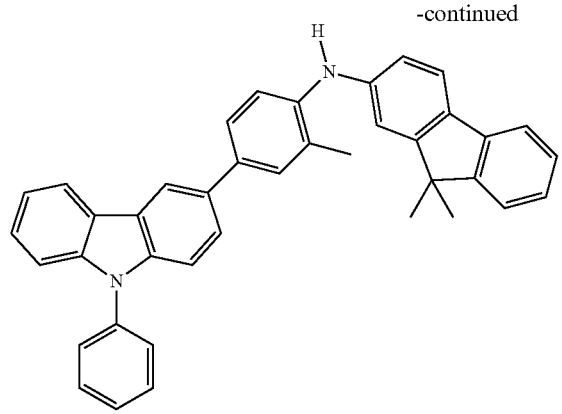
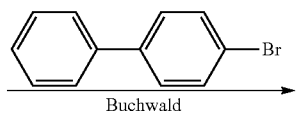

Buchwald

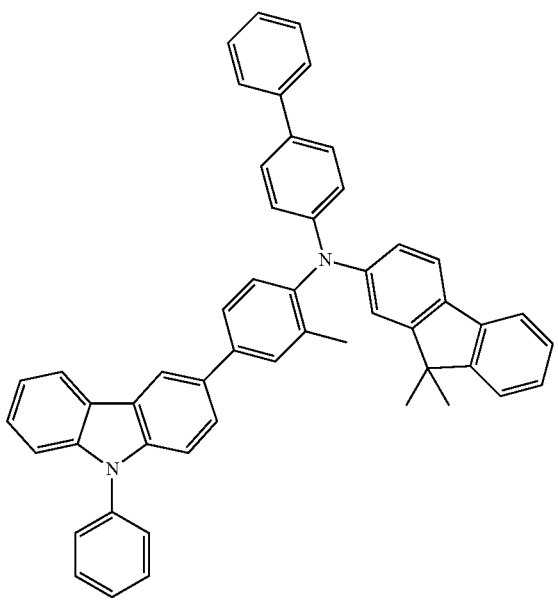

a) 2-Methyl-4-(9-phenyl-9H-carbazol-3-yl)phenylamine

Firstly degassed 9-phenyl-3-(4,4,5,5-tetramethyl-1,3,2-dioxaborolan-2-yl)-9H-carbazole (77.0 g, 209 mmol), then degassed 4-bromo-2-methyl-phenylamine (42.7 g, 229 mmol) and subsequently tetrakistriphenyl-phosphinepalladium (12.0 g, 10 mmol) are added to a mixture of toluene (1.5 l), dioxane (600 ml) and 2 M potassium carbonate solution (1.04 l). The reaction mixture is stirred at 90° C. for 20 h, cooled to room temperature for work-up and diluted with toluene and water. The organic phase is separated off, washed with water, dried and evaporated. After filtration of the residue through silica gel (heptane/toluene/dichloromethane), 2-methyl-4-(9-phenyl-9H-carbazol-3-yl)phenylamine is isolated in the form of a yellow oil (28.0 g, 39% of theory).

b) (9,9-Dimethyl-9H-fluoren-2-yl)-[2-methyl-4-(9-phenyl-9H-carbazol-3-yl)phenyl]amine 1,1'-Bis(diphenylphosphino)ferrocene (408 mg, 0.7 mmol), palladium acetate (165 mg, 0.7 mmol) and sodium tert-butoxide (6.1 g, 64 mmol) are added to a solution of 2-methyl-4-(9-phenyl-9H-carbazol-3-yl)phenylamine (24.6 g, 49 mmol) and 2-bromo-9,9-dimethyl-9H-fluorene (13.4 g, 49 mmol) in degassed toluene (100 ml), and the mixture is heated under reflux for 2 h. The reaction mixture is cooled to room temperature, diluted with toluene and filtered firstly through Celite and subsequently through silica gel. A further filtration column (ethyl acetate/heptane) gives a pale-yellow solid, which is extracted with heptane in a Soxhlet extractor and recrystallised a number of times from heptane, giving (9,9-dimethyl-9H-fluoren-2-yl)-[2-methyl-4-(9-phenyl-9H-carbazol-3-yl)phenyl]amine in the form of a pale-yellow solid (12.4 g, 47% of theory).

c) Biphenyl-4-yl-(9,9-dimethyl-9H-fluoren-2-yl)-[2-methyl-4-(9-phenyl-9H-carbazol-3-yl)phenyl]amine 1,1'-Bis(diphenylphosphino)ferrocene (191 mg, 0.3 mmol), palladium acetate (77 mg, 0.3 mmol) and sodium tert-butoxide (2.9 g, 30 mmol) are added to a solution of (9,9-dimethyl-9H-fluoren-2-yl)-[2-methyl-4-(9-phenyl-9H-carbazol-3-yl)phenyl]amine (12.4 g, 23 mmol) and 4-bromobiphenyl (5.4 g, 23 mmol) in degassed toluene (50 ml), and the mixture is heated under reflux for 20 h. The reaction mixture is cooled to room temperature, diluted with toluene and filtered firstly through Celite and subsequently through aluminium oxide. The crude product is subsequently recrystallised a number of times from heptane and purified by sublimation twice in vacuo ($p=3\times10^{-4}$ mbar, T=301° C.). The product biphenyl-4-yl-(9,9-dmethyl-9H-fluoren-2-yl)-[2-methyl-4-(9-phenyl-9H-carbazol-3-yl)phenyl]amine is isolated in the form of a pale-yellow solid (3.3 g, 21% of theory, purity >99.9% according to HPLC).

B) Device Examples

Use of the Material According to the Invention HTM1 as a Hole Transporting Material in an OLED OLEDs are produced by a general process in accordance with WO 2004/058911, which is adapted to the circumstances described here (layer-thickness variation, materials used).

The following examples V1, V2 and E1 (Tables 1 and 2) give both comparative OLED data and data obtained with the material according to the invention HTM1.

Glass plates coated with structured ITO (indium tin oxide) in a thickness of 150 nm are coated with 20 nm of PEDOT (spin-coated from water; purchased from H. C. Starck, Goslar, Germany; poly(3,4-ethylenedioxy-2,5-thiophene)) for improved processing. These coated glass plates are the substrates to which the OLEDs are applied. The layer sequence of the OLEDs is substrate/hole-injection layer (HIL)/hole-transport layer (HTL)/optional interlayer (IL)/electron blocking layer (EBL)/emission layer (EML)/electron-transport layer (ETM)/optional electron injection layer (EIL)/cathode. The cathode is formed by a 100 nm thick aluminium layer.

The detailed structure of the OLEDs is shown in Table 1. The compounds used for the OLED are shown in Table 3.

All materials are applied by thermal vapor deposition in a vacuum chamber. The emitting layer comprises at least one host material (matrix) and at least one dopant material (emitter material) which is added by co-evaporation. An entry H1:SEB1 (95%/5%) in this case means that a mixture of materials H1 in 95 volume percent and SEB1 in 5 volume percent is present in the layer. Besides the emitting layer, also other layers, e.g. the electron transport layer, may comprise a mixture of two or more materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminance, calculated from current/voltage/luminance characteristic lines (IUL characteristic lines), and the lifetime are determined. The spectra are measured at a luminance density of 1000 cd/m$^2$. From this, the color coordinates (CIE 1931 x,y) are calculated. U @ 1000 cd/m$^2$ in Table 2 means the voltage necessary for a luminance density of 1000 cd/m$^2$. Eff @ 1000 cd/m$^2$ means the external current efficiency at a luminance density of 1000 cd/m$^2$. LT65 @ 6000 cd/m$^2$ is the lifetime at 6000 cd/m$^2$ until the luminance density has dropped to 65% of its initial value, e.g. to 3900 cd/m$^2$. The data obtained for the different OLEDs is shown in Table 2.

The materials according to the invention are particularly suitable for use in a HTL or an EBL, either als a single compound or in mixture with one or more other compounds.

E1 shows data obtained with the material according to the invention HTM1 used as a hole transport material. In the comparative examples V1 and V2, the compounds known in the state of the art NPB (V1) and HTMV1 (V2) are used.

The comparison shows that the inventive compound leads to a higher efficiency and lifetime of the OLED than the NPB.

Compared with HTMV1, the lifetime improves whereas the efficiency remains nearly constant.

TABLE 1

| | OLED structures | | | | | | |
|---|---|---|---|---|---|---|---|
| Bsp. | IL Thickness/ nm | HTL Thickness/ nm | IL Thickness/ nm | EBL Thickness/ nm | EML Thickness/ nm | ETL Thickness/ nm | EIL Thickness/ nm |
| V1 | HIL1 5 nm | HIL2 140 nm | HIL1 5 nm | NPB 20 nm | H1(95%):SEB1(5%) 20 nm | ETM1(50%):LiQ(50%) 30 nm | LiQ 1 nm |
| V2 | HIL1 5 nm | HIL2 140 nm | HIL1 5 nm | HTMV1 20 nm | H1(95%):SEB1(5%) 20 nm | ETM1(50%):LiQ(50%) 30 nm | LiQ 1 nm |
| E1 | HIL1 5 nm | HIL2 140 nm | HIL1 5 nm | HTM1 20 nm | H1(95%):SEB1(5%) 20 nm | ETM1(50%):LiQ(50%) 30 nm | LiQ 1 nm |

TABLE 2

| | OLED data | | | | |
|---|---|---|---|---|---|
| | U @ 1000 cd/m2 | Eff @ 1000 cd/m2 | LT65 @ 6000 cd/m$^2$ | CIE | |
| Bsp. | V | cd/A | h | x | y |
| V1 | 4.2 | 9.6 | 110 | 0.14 | 0.16 |
| V2 | 4.1 | 10.7 | 165 | 0.14 | 0.16 |
| E1 | 3.8 | 10.5 | 195 | 0.14 | 0.16 |

TABLE 3
Structures of the compounds used
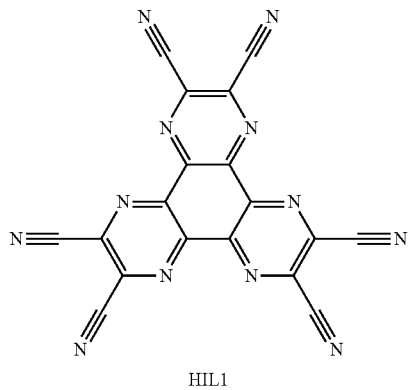 [SMILES: N#Cc1nc2c3nc(C#N)c(C#N)nc3c3nc(C#N)c(C#N)nc3c2nc1C#N]
HIL1
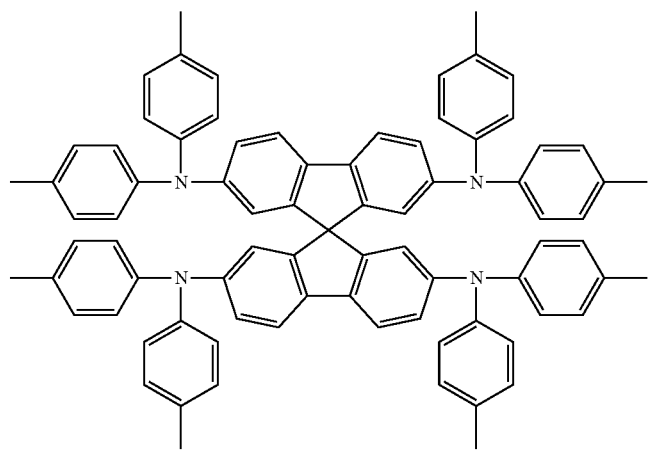
HTL
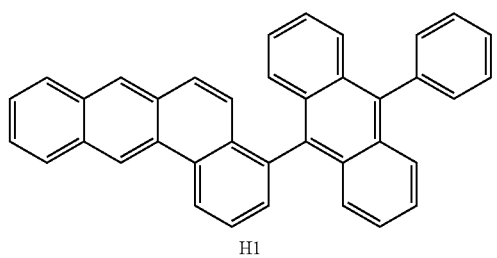
H1
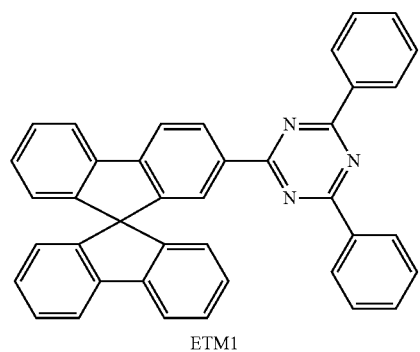 [SMILES: c1ccc(-c2nc(-c3ccccc3)nc(-c3ccc4c(c3)C3(c5ccccc5-c5ccccc53)c3ccccc3-4)n2)cc1]
ETM1

TABLE 3-continued
Structures of the compounds used
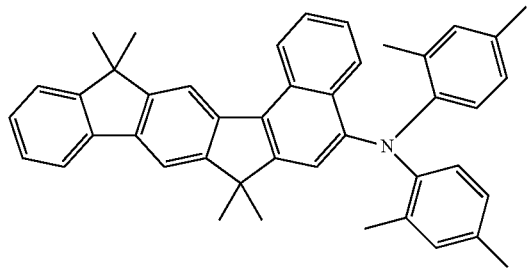
SEB1
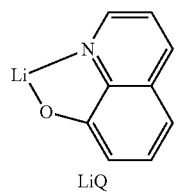
LiQ
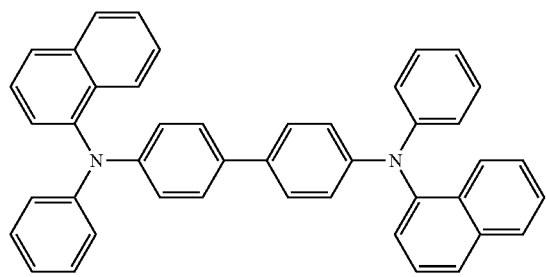
NPB
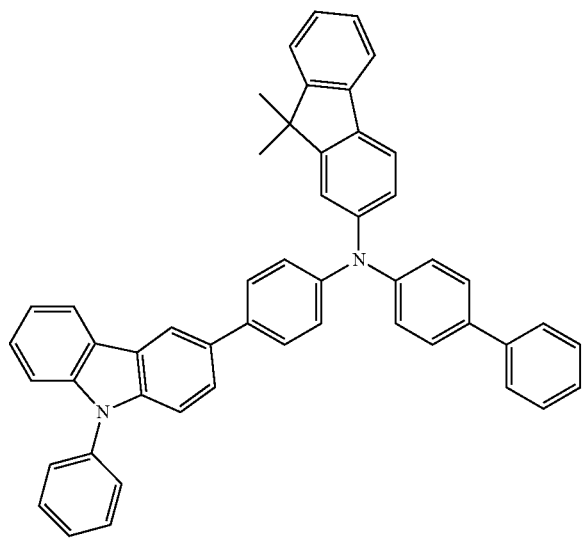
HTMV1

TABLE 3-continued

Structures of the compounds used

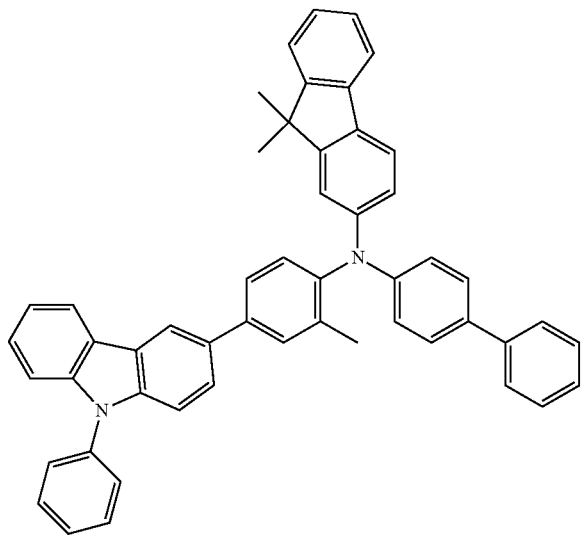

HTM1

The invention claimed is:

1. A compound of formula (I)

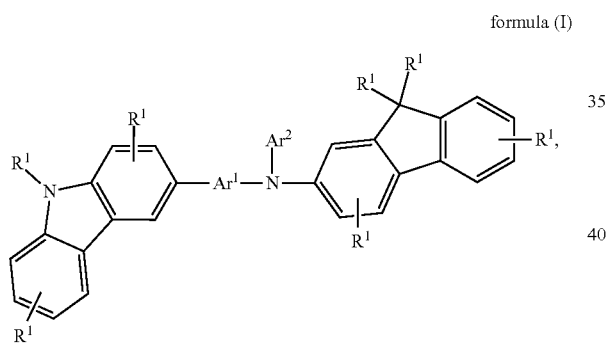

formula (I)

wherein:

Ar$^1$ is

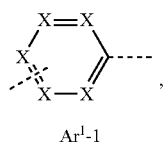

Ar$^1$-1 which is substituted by at least one radical R$^4$ at a position ortho to the nitrogen, and which Ar$^1$-1 is optionally further substituted by one or more radicals R$^4$ or R$^1$, and X is, identically or differently on each occurrence, CR$^4$ or CR$^1$, wherein at least one group X per formula must be CR$^4$, wherein the dashed line on the left denotes the bond from the group Ar$^1$ to the carbazole group and the dashed line on the right denotes the bond from the group Ar$^1$ to the nitrogen atom;

Ar$^2$ is an aromatic in system having 6 to 12 aromatic ring atoms, optionally substituted by one or more radicals R$^1$;

R$^4$ is, identically or differently on each occurrence, a straight-chain alkyl group having 1 to 8 C atoms, or a branched alkyl group having 3 to 8 C atoms, each of which is optionally substituted by one or more radicals R$^3$;

R$^1$ is, identically or differently on each occurrence, H, D, a straight-chain alkyl group having 1 to 20 C atoms or a branched or cyclic alkyl group having 3 to 20 C atoms, each of which is optionally substituted by one or more radicals R$^3$, or an aromatic or heteroaromatic ring system having 5 to 20 aromatic ring atoms, optionally substituted by one or more radicals R$^3$;

R$^3$ is, identically or differently on each occurrence, H, D, F or an aliphatic, aromatic and/or heteroaromatic organic radical haying 1 to 20 C atoms, in which, in addition, one or more H atoms are optionally replaced by D or F; two or more substituents R$^3$ optionally define an aliphatic or aromatic ring;

and where a group R$^1$ is optionally bonded to any of the free positions of the aromatic rings in formula (I).

2. The compound of claim 1, wherein the radical R$^4$ is bonded to the group Ar$^1$ in both positions ortho to the nitrogen.

3. The compound of claim 1, wherein the group Ar$^1$ is one of the following formulae Ar$^1$-21 or Ar$^1$-22

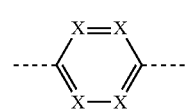

Ar$^1$-21

-continued

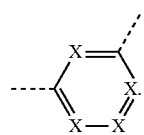
Ar¹-22

4. The compound of claim 1, wherein the compound conforms to the following formula (I-1) or formula (I-2)

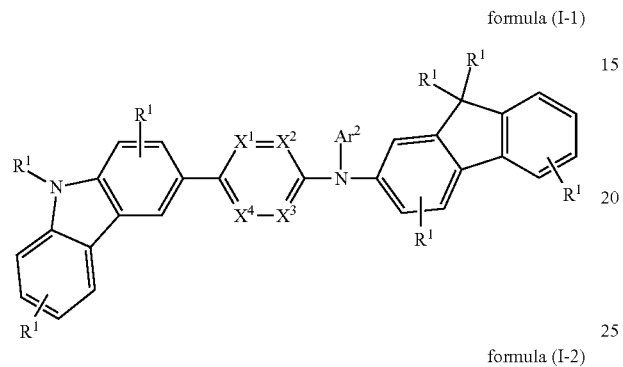
formula (I-1)

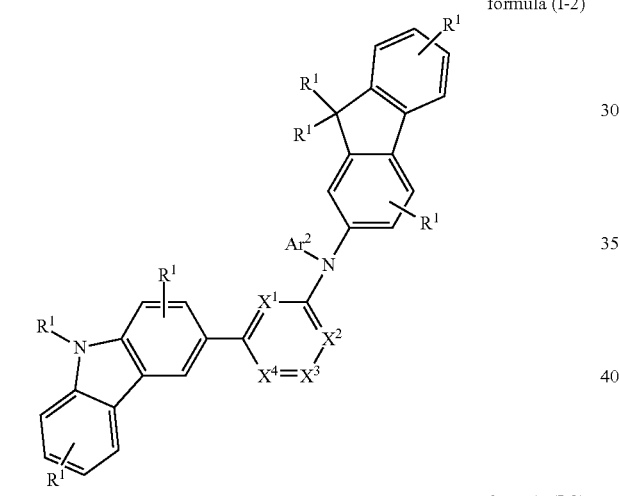
formula (I-2)

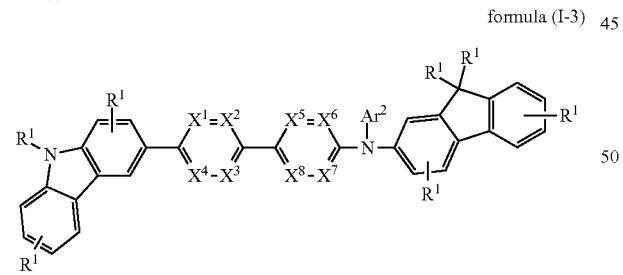
formula (I-3)

wherein a group R¹ is optionally bonded to any of the free positions of the aromatic rings in formula (I-1) or formula (I-2), and X¹ to X⁴ are selected from $CR^A$ and CH, wherein at least one of the groups X² or X³ in formula (I-1) is $CR^A$, or at least one of the groups X¹ or X² in formula (I-2) is $CR^A$.

5. A process for the preparation of the compound of claim 1, said process comprising reacting the group Ar¹ with a carbazole derivative and with a fluorene derivative by one or more organometallic coupling reactions.

6. An oligomer, polymer, or dendrimer, comprising one or more compounds of formula (1)

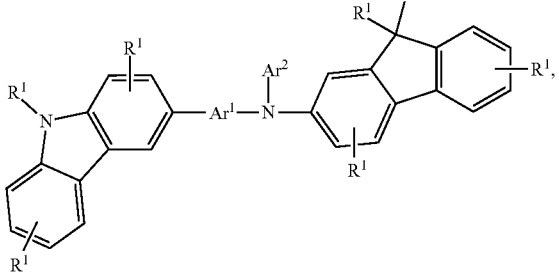
formula (I)

wherein:
Ar¹ is an aromatic ring system having 6 to 30 aromatic ring atoms or a heteroaromatic ring system having 5 to 30 aromatic ring atoms, which is substituted by at least one radical $R^A$ and which is optionally further substituted by one or more radicals $R^1$;

Ar² is an aromatic ring system having 6 to 30 aromatic ring atoms or a heteroaromatic ring system having 5 to 30 aromatic ring atoms, optionally substituted by one or more radicals $R^1$;

$R^A$ is, identically or differently on each occurrence, F, Cl, CN, $Si(R^3)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, all of which are optionally substituted by one or more radicals $R^3$ and where one or more adjacent or non-adjacent $CH_2$ groups in the above-mentioned groups are optionally replaced by $-R^3C=CR^3-$, $-C\equiv C-$, $-Si(R^3)_2-$, $C=O$, $C=NR^3$, $-COO-$, $-CONR^3-$, $-NR^3-$, $P(=O)(R^3)$, $-O-$, $-S-$, SO or $SO_2$ and where one or more H atoms in the above-mentioned groups are optionally replaced by D, F, Cl, Br, I, CN or $NO_2$;

$R^1$ is, identically or differently on each occurrence, H, F, Cl, Br, I, $B(OR^3)_2$, CHO, $C(O)R^3$, $CR^3=C(R^3)_2$, CN, $COOR^3$, $CON(R^3)_2$, $Si(R^3)_3$, $N(R^3)_2$, $NO_2$, $P(=O)(R^3)_2$, $OSO_2R^3$, OH, $S(=O)R^3$, $S(=O)_2R^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, all of which are optionally substituted by one or more radicals $R^3$ and wherein one or more adjacent or non-adjacent $CH_2$ groups in the above-mentioned groups are optionally replaced by $-R^3C=CR^3-$, $-C\equiv C-$, $-Si(R^3)_2$, $Ge(R^3)_2$, $Sn(R^3)_2$, $C=O$, $C=S$, $C=Se$, $C=NR^3$, $-COO-$, $-CONR^3-$, $NR^3$, $P(=O)(R^3)$, $-O-$, $-S-$, SO or $SO_2$ and where one or more H atoms in the above-mentioned groups are optionally replaced by D, F, Cl, Br, I, CN or $NO_2$, or an aromatic or heteroaromatic ring system having 5 to 60 aromatic ring atoms, optionally substituted by one or more radicals $R^3$, or an aryloxy or heteroaryloxy group having 5 to 60 aromatic ring atoms, optionally substituted by one or more radicals R³, or a combination of these systems, wherein two or more radicals R¹ optionally define an aliphatic or aromatic ring;

R³ is, identically or differently on each occurrence, H, D, F or an aliphatic, aromatic and/or heteroaromatic organic radical having 1 to 20 C atoms, in which, in addition, one or more H atoms are optionally replaced by D or F; two or more substituents R³ optionally define an aliphatic or aromatic ring;

and where a group R¹ is optionally bonded to any of the free positions of the aromatic rings in formula (I), wherein the bond(s) to said oligomer, polymer, or dendrimer, is optionally localised at any desired positions substituted by R¹ in said formula (I).

7. A formulation comprising at least one compound of claim 1 and at least one solvent.

8. A formulation comprising at least one oligomer, polymer, or dendrimer, of claim 6 and at least one solvent.

9. The compound of claim 1, wherein the compound is present in an electronic device.

10. The compound of claim 1, wherein the compound is present in an organic electroluminescent device (OLED).

11. The oligomer, polymer, or dendritmer, of claim 6, wherein said oligomer, polymer, or dendrimer, is present in an electronic device.

12. The oligomer, polymer, or dendrimer, of claim 6, wherein said oligomer, polymer, or dendrimer, is present in an organic electroluminescent device (OLED).

13. An electronic device comprising at least one compound of claim 1, wherein the electronic device is selected from an organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC), organic laser diode (O-laser) and organic electroluminescent device (OLED).

14. An electronic device comprising at least one oligomer, polymer, or dendrimer, of claim 6, wherein the electronic device is selected from an organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC), organic laser diode (O-laser) and organic electroluminescent device (OLED).

15. The electronic device of claim 13, wherein the electronic device is an organic electroluminescent device, and wherein said at least one compound is employed as hole-transport material in a hole-transport layer or hole-injection layer and/or is employed as matrix material in an emitting layer.

16. The electronic device of claim 14, wherein the electronic device is an organic electroluminescent device, and wherein said at least one oligomer, polymer, or dendrimer, is employed as hole-transport material in a hole-transport layer or hole-injection layer and/or is employed as matrix material in an emitting layer.

17. A compound of formula (I)

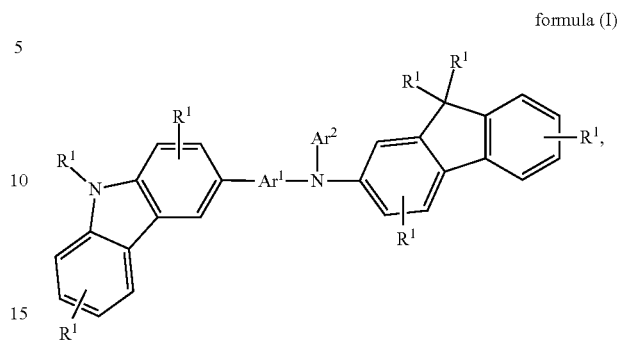

formula (I)

wherein:
Ar¹ is one of formula Ar¹-21 or formula Ar¹-22

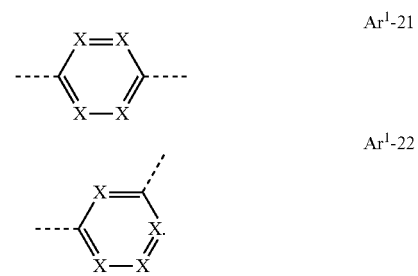

which is substituted by at least one radical R⁴ at a position ortho to the nitrogen, and which Ar¹-21 or Ar¹-22 is optionally further substituted by one or more radicals R⁴ or R¹, and X is, identically or differently on each occurrence, CR⁴ or CR¹, wherein at least one group X per formula must be CR⁴, wherein the dashed line on the left denotes the bond from the group Ar¹ to the carbazole group and the dashed line on the right denotes the bond from the group Ar¹ to the nitrogen atom, Ar² is an aromatic ring system having 6 to 12 aromatic ring atoms, optionally substituted by one or more radicals R¹;

R⁴ is, identically or differently on each occurrence, a straight-chain alkyl group having 1 to 8 C atoms, which is optionally substituted by one or more radicals R³, or a branched alkyl having 3 to 8 C atoms, which is optionally substituted by one or more radicals R³;

R¹ is, identically or differently on each occurrence, H, D, a straight-chain alkyl group having 1 to 20 C atoms or a branched or cyclic alkyl group having 3 to 20 C atoms, each of which is optionally substituted by one or more radicals R³, or an aromatic or heteroaromatic ring system having 5 to 20 aromatic ring atoms, optionally substituted by one or more radicals R³;

R³ is, identically or differently on each occurrence, H, D, F or an aliphatic, aromatic and/or heteroaromatic organic radical having 1 to 20 C atoms, in which, in addition, one or more H atoms are optionally replaced by D or F; two or more substituents R³ optionally define an aliphatic or aromatic ring;

and where a group R¹ is optionally bonded to any of the free positions of the aromatic rings in formula (I).

18. An electronic device comprising at least one compound of claim 17, wherein the electronic device is selected from an organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC), organic laser diode (O-laser) and organic electroluminescent device (OLED).

19. The compound of claim 17, wherein $R^1$ is selected from the group consisting of benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, dihydrophenanthrene, dihydropyrene, tetrahydropyrene, cis- or trans-indenofluorene, furan, benzofuran, isobenzofuran, dibenzofuran, thiophene, benzothiopliene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxa-zole, 1,2-thiazole, 1,3-thiazole, benzothiazole, pyridazine, benzopyridazine, pyrimidine, benzopyrimidine, quinoxaline, 1,5diazaanthracene, 2,7-diazapyrene, pyrene, 2,5-diazapyrene, 1,6-diazapyrene, 1,8-diazapyrene, 4,5-diazapyrene, 4,5,9,10-tetraazaperyiene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,5-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5tetrazine, purine, pteridine, indolizine and benzothiadizoie, wherein $R^1$ is optionally substituted by one or more radicals R3, and $Ar^2$ is selected from the group consisting of benzene, naphthalene, biphenyl, biphenylene terphenyl, and terphenylene.

20. A compound of formula

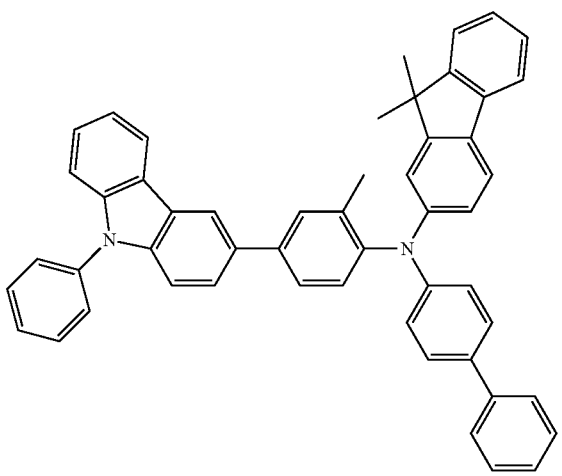

21. A compound of formula

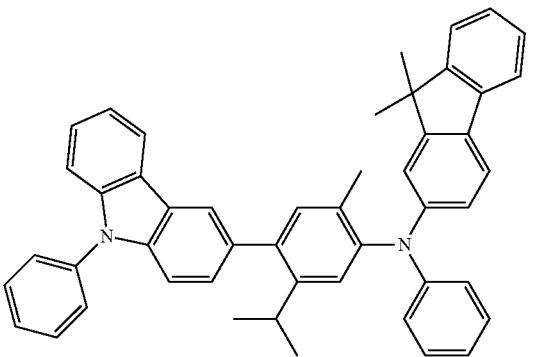

22. A compound of formula

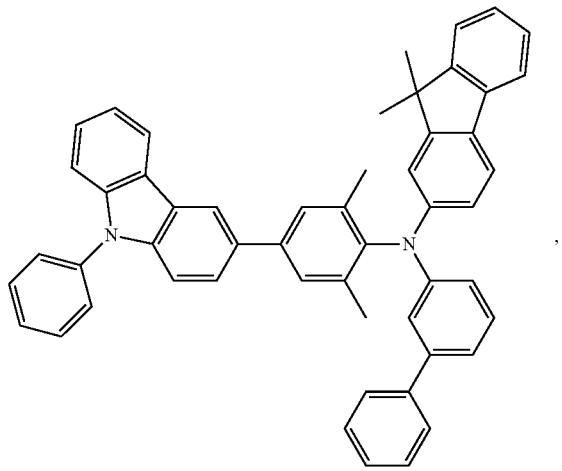 [SMILES: Cc1cc(-c2ccc3c(c2)c2ccccc2n3-c2ccccc2)cc(C)c1N(c1cccc(-c2ccccc2)c1)c1ccc2c(c1)C(C)(C)c1ccccc1-2]

23. A compound of formula

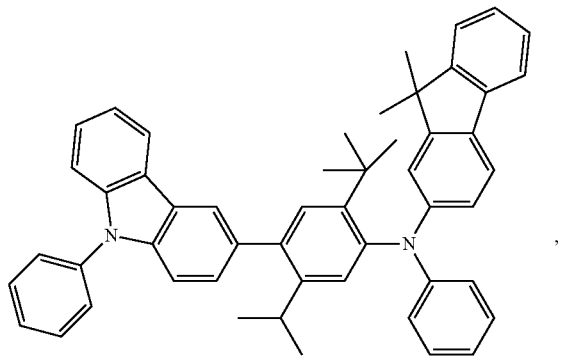 [SMILES: CC(C)c1cc(N(c2ccccc2)c2ccc3c(c2)C(C)(C)c2ccccc2-3)c(C(C)(C)C)cc1-c1ccc2c(c1)c1ccccc1n2-c1ccccc1]

24. A compound of formula
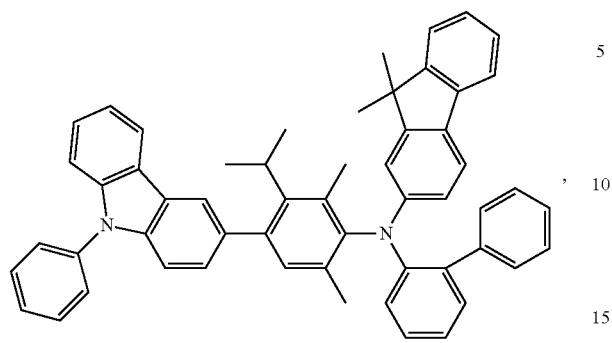
.